(12) United States Patent
Tams

(10) Patent No.: US 11,896,024 B2
(45) Date of Patent: *Feb. 13, 2024

(54) METHOD OF GLYCATION OF A POLYPEPTIDE

(71) Applicant: Novozymes A/S, Bagsvaerd (DK)

(72) Inventor: Jeppe Wegener Tams, Gentofte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/687,786

(22) Filed: Mar. 7, 2022

(65) Prior Publication Data

US 2022/0232843 A1 Jul. 28, 2022

Related U.S. Application Data

(62) Division of application No. 16/609,276, filed as application No. PCT/EP2018/062539 on May 15, 2018, now Pat. No. 11,304,425.

(30) Foreign Application Priority Data

May 15, 2017 (EP) .................................... 17171174
Mar. 16, 2018 (EP) .................................... 18162193

(51) Int. Cl.
    *A23C 9/12* (2006.01)
    *A23C 9/13* (2006.01)
    *A23C 9/15* (2006.01)
    *C12P 19/18* (2006.01)
    *C12P 19/04* (2006.01)

(52) U.S. Cl.
    CPC .......... *A23C 9/1206* (2013.01); *A23C 9/1307* (2013.01); *A23C 9/1512* (2013.01); *C12P 19/04* (2013.01); *C12P 19/18* (2013.01); *C12Y 302/01023* (2013.01); *C12Y 302/01108* (2013.01)

(58) Field of Classification Search
    None
    See application file for complete search history.

(56) References Cited

U.S. PATENT DOCUMENTS

| | | | | |
|---|---|---|---|---|
| 8,734,791 B2 * | 5/2014 | Lazar | ................ | C07K 16/2896 424/153.1 |
| 2009/0297660 A1 | 12/2009 | Silver | | |
| 2012/0040051 A1 | 2/2012 | Chen | | |
| 2016/0108440 A1 | 4/2016 | Pedersen | | |
| 2016/0168608 A1 | 6/2016 | Kwon et al. | | |
| 2016/0278421 A1 | 9/2016 | Berrocal et al. | | |
| 2017/0164631 A1 | 6/2017 | Ray et al. | | |
| 2022/0232843 A1* | 7/2022 | Tams | ..................... | C12P 19/04 |

FOREIGN PATENT DOCUMENTS

| | | |
|---|---|---|
| CN | 101103743 A | 1/2008 |
| CN | 101831389 A | 9/2010 |
| CN | 104812908 A | 7/2015 |
| CN | 106455600 A | 2/2017 |
| DE | 2431297 A1 | 8/1976 |
| EP | 0458358 A1 | 11/1991 |
| EP | 2982760 A1 | 2/2016 |
| JP | 11-018763 A | 1/1999 |
| KR | 1020150116114 A | 10/2015 |
| WO | 01/90317 A2 | 11/2001 |
| WO | 2008/037839 A1 | 4/2008 |
| WO | 2009/071539 A1 | 6/2009 |
| WO | 2010/098561 A2 | 9/2010 |
| WO | 2011/093907 A1 | 8/2011 |
| WO | 2012/160080 A1 | 11/2012 |
| WO | 2013/182686 A1 | 12/2013 |
| WO | 2015/086746 A1 | 6/2015 |
| WO | 2015/132349 A1 | 9/2015 |
| WO | 2016/071500 A1 | 5/2016 |
| WO | 2016071500 A1 | 5/2016 |

OTHER PUBLICATIONS

Ledesma-Osuna et al. (Acta Biochimica Polonica, vol. 55 No. 3, 2008, pp. 491-497).*
Anonymous, Skim milk powder standard, ADPI (2017).
Boos et al., Carbohydrate Research, vol. 7, No. 4, pp. 381-394 (1968).
Brake et al., Proc. Natl. Acad. Sci. USA, vol. 75, No. 10, pp. 4824-4827 (1978).
Chen et al., Process Biochemistry, vol. 38, pp. 801-808 (2002).
Forster-Fromme et al., International Dairy Journal, vol. 21, No. 12, pp. 940-948 (2011).
Fowler et al., Journal of Biological Chemistry, vol. 258, No. 23, pp. 14354-14358 (1983).
Ganea, Revue Roumaine de Biochimie, vol. 25, No. 2, pp. 101-106 (1988).
Hirata et al., Journal of Bacteriology, vol. 166, No. 3, pp. 722-727 (1986).
Jorgensen et al., Appl. Microbiol. Biotechnol., vol. 57, pp. 647-652 (2001).
Mozaffar et al., Journal of Food Science, vol. 50, pp. 1602-1606 (1985).
Otieno, Comprehensive Reviews in Food Science and Food Safety, vol. 9, pp. 471-482 (2010).
Rojas et al., J. Mol. Biol., vol. 343, No. 5, pp. 1281-1292 (2004).
Song et al., Bioscience, Biotechnology, and Biochemistry, vol. 77, No. 1, pp. 73-79 (2013).
Vera et al., Carbohydrate Research, vol. 346, No. 6, pp. 745-752 (2011).

* cited by examiner

*Primary Examiner* — Hope A Robinson
(74) *Attorney, Agent, or Firm* — Yoshimi D. Barron

(57) ABSTRACT

The present invention relates to compositions, particularly liquid compositions, comprising enzymes, methods of making the compositions, and uses of the same for making, e.g., dairy products.

12 Claims, No Drawings
Specification includes a Sequence Listing.

SEQUENCE LISTING

<160> NUMBER OF SEQ ID NOS: 15

<210> SEQ ID NO 1
<211> LENGTH: 1304
<212> TYPE: PRT
<213> ORGANISM: Artificial sequence
<220> FEATURE:
<223> OTHER INFORMATION: Synthetic construct

<400> SEQUENCE: 1

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asn Val Thr Met
        195                 200                 205

Asn Leu Thr Thr Lys Val Ala Asn Asp Thr Lys Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

```
Gly Val Asn Ser Ile Arg Thr Thr His Asn Pro Ala Ala Lys Ala Leu
            355                 360                 365

Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
                420                 425                 430

Asp Arg Asn Ala Pro Ser Val Ile Met Trp Ser Leu Gly Asn Glu Met
                435                 440                 445

Met Glu Gly Ile Ser Gly Ser Val Ser Gly Phe Pro Ala Thr Ser Ala
                450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
                500                 505                 510

Asp Gly Ala Asn Tyr Asp Lys Ile Arg Thr Thr His Pro Ser Trp Ala
                515                 520                 525

Ile Tyr Gly Ser Glu Thr Ala Ser Ala Ile Asn Ser Arg Gly Ile Tyr
                530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
                595                 600                 605

Gly Ala Val Gly Ser Trp Pro Ser Pro Lys Asn Ser Tyr Phe Gly Ile
                610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
                675                 680                 685

Thr Glu Lys Arg Leu Ile Gly Glu Lys Ser Phe Thr Lys Thr Thr
                690                 695                 700

Ala Ala Gly Tyr Thr Tyr Gln Val Tyr Glu Gly Ala Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
                740                 745                 750

Glu Gly Ser Thr Glu Gly Asn Ala Ser Val Thr Thr Thr Gly Lys Ala
                755                 760                 765
```

```
Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
                835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
                900                 905                 910

Val Arg Tyr Ser Asp Gly Thr Ser Asp Arg Gln Asn Val Thr Trp Asp
                915                 920                 925

Ala Val Ser Asp Asp Gln Ile Ala Lys Ala Gly Ser Phe Ser Val Ala
930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
                980                 985                 990

Val Thr Ser Ala Asn Phe Ala Val Asp Trp Thr Lys Pro Ala Asp Thr
                995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050

Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
    1115                1120                1125

Ala Val Arg Phe Pro Asp Ala Gly Lys Thr Lys Ile Gln Ile Ser
    1130                1135                1140

Ala Asp Gly Lys Asn Trp Thr Asp Leu Ala Ala Thr Glu Thr Ile
    1145                1150                1155

Ala Ala Gln Glu Ser Ser Glu Arg Val Lys Pro Tyr Thr Tyr Asp
    1160                1165                1170
```

```
Phe Ala Pro Val Gly Ala Thr Phe Val Lys Val Thr Val Thr Asn
    1175                1180                1185

Ala Asp Thr Thr Thr Pro Ser Gly Val Val Cys Ala Gly Leu Thr
    1190                1195                1200

Glu Ile Glu Leu Lys Thr Ala Thr Ser Lys Phe Val Thr Asn Thr
    1205                1210                1215

Ser Ala Ala Leu Ser Ser Leu Thr Val Asn Gly Thr Lys Val Ser
    1220                1225                1230

Asp Ser Val Leu Ala Ala Gly Ser Tyr Asn Thr Pro Ala Ile Ile
    1235                1240                1245

Ala Asp Val Lys Ala Glu Gly Glu Gly Asn Ala Ser Val Thr Val
    1250                1255                1260

Leu Pro Ala His Asp Asn Val Ile Arg Val Ile Thr Glu Ser Glu
    1265                1270                1275

Asp His Val Thr Arg Lys Thr Phe Thr Ile Asn Leu Gly Thr Glu
    1280                1285                1290

Gln Glu Phe Pro Ala Asp Ser Asp Glu Arg Asp
    1295                1300
```

<210> SEQ ID NO 2
<211> LENGTH: 1931
<212> TYPE: PRT
<213> ORGANISM: Artificial sequence
<220> FEATURE:
<223> OTHER INFORMATION: Synthetic construct

<400> SEQUENCE: 2

```
Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ala Val Glu Asp Ala
                20                  25                  30

Thr Arg Ser Asp Ser Thr Thr Gln Met Ser Ser Thr Pro Glu Val Ala
            35                  40                  45

Tyr Ser Ser Ala Val Asp Ser Lys Gln Asn Arg Thr Ser Asp Phe Asp
        50                  55                  60

Ala Asn Trp Lys Phe Met Leu Ser Asp Ser Val Gln Ala Gln Asp Pro
65                  70                  75                  80

Ala Phe Asp Asp Ser Ala Trp Gln Gln Val Asp Leu Pro His Asp Tyr
                85                  90                  95

Ser Ile Thr Gln Lys Tyr Ser Gln Ser Asn Glu Ala Glu Ser Ala Tyr
            100                 105                 110

Leu Pro Gly Gly Thr Gly Trp Tyr Arg Lys Ser Phe Thr Ile Asp Arg
        115                 120                 125

Asp Leu Ala Gly Lys Arg Ile Ala Ile Asn Phe Asp Gly Val Tyr Met
    130                 135                 140

Asn Ala Thr Val Trp Phe Asn Gly Val Lys Leu Gly Thr His Pro Tyr
145                 150                 155                 160

Gly Tyr Ser Pro Phe Ser Phe Asp Leu Thr Gly Asn Ala Lys Phe Gly
                165                 170                 175

Gly Glu Asn Thr Ile Val Val Lys Val Glu Asn Arg Leu Pro Ser Ser
            180                 185                 190

Arg Trp Tyr Ser Gly Ser Gly Ile Tyr Arg Asp Val Thr Leu Thr Val
        195                 200                 205

Thr Asp Gly Val His Val Gly Asn Asn Gly Val Ala Ile Lys Thr Pro
    210                 215                 220
```

-continued

```
Ser Leu Ala Thr Gln Asn Gly Gly Asp Val Thr Met Asn Leu Thr Thr
225                 230                 235                 240

Lys Val Ala Asn Asp Thr Glu Ala Ala Ala Asn Ile Thr Leu Lys Gln
            245                 250                 255

Thr Val Phe Pro Lys Gly Gly Lys Thr Asp Ala Ala Ile Gly Thr Val
        260                 265                 270

Thr Thr Ala Ser Lys Ser Ile Ala Ala Gly Ala Ser Ala Asp Val Thr
    275                 280                 285

Ser Thr Ile Thr Ala Ala Ser Pro Lys Leu Trp Ser Ile Lys Asn Pro
290                 295                 300

Asn Leu Tyr Thr Val Arg Thr Glu Val Leu Asn Gly Lys Val Leu
305                 310                 315                 320

Asp Thr Tyr Asp Thr Glu Tyr Gly Phe Arg Trp Thr Gly Phe Asp Ala
            325                 330                 335

Thr Ser Gly Phe Ser Leu Asn Gly Glu Lys Val Lys Leu Lys Gly Val
        340                 345                 350

Ser Met His His Asp Gln Gly Ser Leu Gly Ala Val Ala Asn Arg Arg
    355                 360                 365

Ala Ile Glu Arg Gln Val Glu Ile Leu Gln Lys Met Gly Val Asn Ser
370                 375                 380

Ile Arg Thr Thr His Asn Pro Ala Ala Lys Ala Leu Ile Asp Val Cys
385                 390                 395                 400

Asn Glu Lys Gly Val Leu Val Glu Glu Val Phe Asp Met Trp Asn
            405                 410                 415

Arg Ser Lys Asn Gly Asn Thr Glu Asp Tyr Gly Lys Trp Phe Gly Gln
        420                 425                 430

Ala Ile Ala Gly Asp Asn Ala Val Leu Gly Gly Asp Lys Asp Glu Thr
    435                 440                 445

Trp Ala Lys Phe Asp Leu Thr Ser Thr Ile Asn Arg Asp Arg Asn Ala
    450                 455                 460

Pro Ser Val Ile Met Trp Ser Leu Gly Asn Glu Met Met Glu Gly Ile
465                 470                 475                 480

Ser Gly Ser Val Ser Gly Phe Pro Ala Thr Ser Ala Lys Leu Val Ala
            485                 490                 495

Trp Thr Lys Ala Ala Asp Ser Thr Arg Pro Met Thr Tyr Gly Asp Asn
        500                 505                 510

Lys Ile Lys Ala Asn Trp Asn Glu Ser Asn Thr Met Gly Asp Asn Leu
    515                 520                 525

Thr Ala Asn Gly Gly Val Val Gly Thr Asn Tyr Ser Asp Gly Ala Asn
    530                 535                 540

Tyr Asp Lys Ile Arg Thr Thr His Pro Ser Trp Ala Ile Tyr Gly Ser
545                 550                 555                 560

Glu Thr Ala Ser Ala Ile Asn Ser Arg Gly Ile Tyr Asn Arg Thr Thr
            565                 570                 575

Gly Gly Ala Gln Ser Ser Asp Lys Gln Leu Thr Ser Tyr Asp Asn Ser
        580                 585                 590

Ala Val Gly Trp Gly Ala Val Ala Ser Ser Ala Trp Tyr Asp Val Val
    595                 600                 605

Gln Arg Asp Phe Val Ala Gly Thr Tyr Val Trp Thr Gly Phe Asp Tyr
    610                 615                 620

Leu Gly Glu Pro Thr Pro Trp Asn Gly Thr Gly Ser Gly Ala Val Gly
625                 630                 635                 640
```

```
Ser Trp Pro Ser Pro Lys Asn Ser Tyr Phe Gly Ile Val Asp Thr Ala
                645                 650                 655

Gly Phe Pro Lys Asp Thr Tyr Tyr Phe Tyr Gln Ser Gln Trp Asn Asp
            660                 665                 670

Asp Val His Thr Leu His Ile Leu Pro Ala Trp Asn Glu Asn Val Val
        675                 680                 685

Ala Lys Gly Ser Gly Asn Asn Val Pro Val Val Tyr Thr Asp Ala
    690                 695                 700

Ala Lys Val Lys Leu Tyr Phe Thr Pro Lys Gly Ser Thr Glu Lys Arg
705                 710                 715                 720

Leu Ile Gly Glu Lys Ser Phe Thr Lys Lys Thr Thr Ala Ala Gly Tyr
                725                 730                 735

Thr Tyr Gln Val Tyr Glu Gly Ser Asp Lys Asp Ser Thr Ala His Lys
            740                 745                 750

Asn Met Tyr Leu Thr Trp Asn Val Pro Trp Ala Glu Gly Thr Ile Ser
        755                 760                 765

Ala Glu Ala Tyr Asp Glu Asn Asn Arg Leu Ile Pro Glu Gly Ser Thr
    770                 775                 780

Glu Gly Asn Ala Ser Val Thr Thr Thr Gly Lys Ala Ala Lys Leu Lys
785                 790                 795                 800

Ala Asp Ala Asp Arg Lys Thr Ile Thr Ala Asp Gly Lys Asp Leu Ser
                805                 810                 815

Tyr Ile Glu Val Asp Val Thr Asp Ala Asn Gly His Ile Val Pro Asp
            820                 825                 830

Ala Ala Asn Arg Val Thr Phe Asp Val Lys Gly Ala Gly Lys Leu Val
        835                 840                 845

Gly Val Asp Asn Gly Ser Ser Pro Asp His Asp Ser Tyr Gln Ala Asp
    850                 855                 860

Asn Arg Lys Ala Phe Ser Gly Lys Val Leu Ala Ile Val Gln Ser Thr
865                 870                 875                 880

Lys Glu Ala Gly Glu Ile Thr Val Thr Ala Lys Ala Asp Gly Leu Gln
                885                 890                 895

Ser Ser Thr Val Lys Ile Ala Thr Thr Ala Val Pro Gly Thr Ser Thr
            900                 905                 910

Glu Lys Thr Val Arg Ser Phe Tyr Tyr Ser Arg Asn Tyr Tyr Val Lys
        915                 920                 925

Thr Gly Asn Lys Pro Ile Leu Pro Ser Asp Val Glu Val Arg Tyr Ser
    930                 935                 940

Asp Gly Thr Ser Asp Arg Gln Asn Val Thr Trp Asp Ala Val Ser Asp
945                 950                 955                 960

Asp Gln Ile Ala Lys Ala Gly Ser Phe Ser Val Ala Gly Thr Val Ala
                965                 970                 975

Gly Gln Lys Ile Ser Val Arg Val Thr Met Ile Asp Glu Ile Gly Ala
            980                 985                 990

Leu Leu Asn Tyr Ser Ala Ser Thr Pro Val Gly Thr Pro Ala Val Leu
        995                 1000                1005

Pro Gly Ser Arg Pro Ala Val Leu Pro Asp Gly Thr Val Thr Ser
    1010                1015                1020

Ala Asn Phe Ala Val His Trp Thr Lys Pro Ala Asp Thr Val Tyr
    1025                1030                1035

Asn Thr Ala Gly Thr Val Lys Val Pro Gly Thr Ala Thr Val Phe
    1040                1045                1050
```

```
Gly Lys Glu Phe Lys Val Thr Ala Thr Ile Arg Val Gln Arg Ser
1055                1060                1065
Gln Val Thr Ile Gly Ser Ser Val Ser Gly Asn Ala Leu Arg Leu
1070                1075                1080
Thr Gln Asn Ile Pro Ala Asp Lys Gln Ser Asp Thr Leu Asp Ala
1085                1090                1095
Ile Lys Asp Gly Ser Thr Thr Val Asp Ala Asn Thr Gly Gly Gly
1100                1105                1110
Ala Asn Pro Ser Ala Trp Thr Asn Trp Ala Tyr Ser Lys Ala Gly
1115                1120                1125
His Asn Thr Ala Glu Ile Thr Phe Glu Tyr Ala Thr Glu Gln Gln
1130                1135                1140
Leu Gly Gln Ile Val Met Tyr Phe Phe Arg Asp Ser Asn Ala Val
1145                1150                1155
Arg Phe Pro Asp Ala Gly Lys Thr Lys Ile Gln Ile Ser Ala Asp
1160                1165                1170
Gly Lys Asn Trp Thr Asp Leu Ala Ala Thr Glu Thr Ile Ala Ala
1175                1180                1185
Gln Glu Ser Ser Asp Arg Val Lys Pro Tyr Thr Tyr Asp Phe Ala
1190                1195                1200
Pro Val Gly Ala Thr Phe Val Lys Val Thr Val Thr Asn Ala Asp
1205                1210                1215
Thr Thr Thr Pro Ser Gly Val Val Cys Ala Gly Leu Thr Glu Ile
1220                1225                1230
Glu Leu Lys Thr Ala Thr Ser Lys Phe Val Thr Asn Thr Ser Ala
1235                1240                1245
Ala Leu Ser Ser Leu Thr Val Asn Gly Thr Lys Val Ser Asp Ser
1250                1255                1260
Val Leu Ala Ala Gly Ser Tyr Asn Thr Pro Ala Ile Ile Ala Asp
1265                1270                1275
Val Lys Ala Glu Gly Glu Gly Asn Ala Ser Val Thr Val Leu Pro
1280                1285                1290
Ala His Asp Asn Val Ile Arg Val Ile Thr Glu Ser Glu Asp His
1295                1300                1305
Val Thr Arg Lys Thr Phe Thr Ile Asn Leu Gly Thr Glu Gln Glu
1310                1315                1320
Phe Pro Ala Asp Ser Asp Glu Arg Asp Tyr Pro Ala Ala Asp Met
1325                1330                1335
Thr Val Thr Val Gly Ser Glu Gln Thr Ser Gly Thr Ala Thr Glu
1340                1345                1350
Gly Pro Lys Lys Phe Ala Val Asp Gly Asn Thr Ser Thr Tyr Trp
1355                1360                1365
His Ser Asn Trp Thr Pro Thr Thr Val Asn Asp Leu Trp Ile Ala
1370                1375                1380
Phe Glu Leu Gln Lys Pro Thr Lys Leu Asp Ala Leu Arg Tyr Leu
1385                1390                1395
Pro Arg Pro Ala Gly Ser Lys Asn Gly Ser Val Thr Glu Tyr Lys
1400                1405                1410
Val Gln Val Ser Asp Asp Gly Thr Asn Trp Thr Asp Ala Gly Ser
1415                1420                1425
Gly Thr Trp Thr Thr Asp Tyr Gly Trp Lys Leu Ala Glu Phe Asn
1430                1435                1440
```

```
Gln Pro Val Thr Thr Lys His Val Arg Leu Lys Ala Val His Thr
1445                1450                1455

Tyr Ala Asp Ser Gly Asn Asp Lys Phe Met Ser Ala Ser Glu Ile
1460                1465                1470

Arg Leu Arg Lys Ala Val Asp Thr Thr Asp Ile Ser Gly Ala Thr
1475                1480                1485

Val Thr Val Pro Ala Lys Leu Thr Val Asp Arg Val Asp Ala Asp
1490                1495                1500

His Pro Ala Thr Phe Ala Thr Lys Asp Val Thr Val Thr Leu Gly
1505                1510                1515

Asp Ala Thr Leu Arg Tyr Gly Val Asp Tyr Leu Leu Asp Tyr Ala
1520                1525                1530

Gly Asn Thr Ala Val Gly Lys Ala Thr Val Thr Val Arg Gly Ile
1535                1540                1545

Asp Lys Tyr Ser Gly Thr Val Ala Lys Thr Phe Thr Ile Glu Leu
1550                1555                1560

Lys Asn Ala Pro Ala Pro Glu Pro Thr Leu Thr Ser Val Ser Val
1565                1570                1575

Lys Thr Lys Pro Ser Lys Leu Thr Tyr Val Val Gly Asp Ala Phe
1580                1585                1590

Asp Pro Ala Gly Leu Val Leu Gln Leu Asn Tyr Asp Asp Asp Ser
1595                1600                1605

Thr Gly Thr Val Thr Trp Asn Thr Gln Thr Ala Gly Asp Phe Thr
1610                1615                1620

Phe Lys Pro Ala Leu Asp Ala Lys Leu Lys Val Thr Asp Lys Thr
1625                1630                1635

Val Thr Val Thr Tyr Gln Gly Lys Ser Ala Val Ile Asp Ile Thr
1640                1645                1650

Val Ser Gln Pro Ala Pro Thr Val Ser Lys Thr Asp Leu Asp Lys
1655                1660                1665

Ala Ile Lys Ala Ile Glu Ala Lys Asn Pro Asp Ser Ser Lys Tyr
1670                1675                1680

Thr Ala Asp Ser Trp Lys Thr Phe Ala Asp Ala Met Ala His Ala
1685                1690                1695

Lys Ala Val Ile Ala Asp Asp Ser Ala Thr Gln Gln Asp Val Asp
1700                1705                1710

Asn Ala Leu Lys Ala Leu Thr Asp Ala Tyr Ala Gly Leu Thr Glu
1715                1720                1725

Lys Thr Pro Glu Pro Ala Pro Val Ser Lys Ser Glu Leu Asp Lys
1730                1735                1740

Lys Ile Lys Ala Ile Glu Ala Glu Lys Leu Asp Gly Ser Lys Tyr
1745                1750                1755

Thr Ala Glu Ser Trp Lys Ala Phe Glu Thr Ala Leu Ala His Ala
1760                1765                1770

Lys Ala Val Ile Ala Ser Asp Ser Ala Thr Gln Gln Asn Val Asp
1775                1780                1785

Ala Ala Leu Gly Ala Leu Thr Ser Ala Arg Asp Gly Leu Thr Glu
1790                1795                1800

Lys Gly Glu Val Lys Pro Asp Pro Lys Pro Glu Pro Gly Thr Val
1805                1810                1815

Asp Lys Ala Ala Leu Asp Lys Ala Val Lys Lys Val Glu Ala Glu
1820                1825                1830
```

Lys Leu Asp Gly Ser Lys Tyr Thr Ala Asp Ser Trp Lys Ala Phe
    1835                1840                1845

Glu Thr Ala Leu Ala His Ala Lys Ala Val Ile Gly Asn Ala Asn
    1850                1855                1860

Ser Thr Gln Phe Asp Ile Asp Asn Ala Leu Ser Met Leu Asn Asp
    1865                1870                1875

Ala Arg Ala Ala Leu Lys Glu Lys Pro Gly Arg Ile Ile Ala Ile
    1880                1885                1890

Ile Asp Gly Ser Ala Leu Ser Lys Thr Gly Ala Ser Val Ala Ile
    1895                1900                1905

Ile Ala Ser Val Ala Ala Ala Met Leu Ala Val Gly Ala Gly Val
    1910                1915                1920

Met Ala Leu Arg Arg Lys Arg Ser
    1925                1930

<210> SEQ ID NO 3
<211> LENGTH: 1341
<212> TYPE: PRT
<213> ORGANISM: Artificial sequence
<220> FEATURE:
<223> OTHER INFORMATION: Synthetic construct

<400> SEQUENCE: 3

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Ile Glu Asp Ala Thr
            20                  25                  30

Arg Ser Asp Ser Thr Thr Gln Met Ser Ser Thr Pro Glu Val Ala Tyr
        35                  40                  45

Ser Ser Ala Val Asp Ser Lys Gln Asn Arg Thr Ser Asp Phe Asp Ala
    50                  55                  60

Asn Trp Lys Phe Met Leu Ser Asp Ser Val Gln Ala Gln Asp Pro Ala
65                  70                  75                  80

Phe Asp Asp Ser Ala Trp Gln Gln Val Asp Leu Pro His Asp Tyr Ser
                85                  90                  95

Ile Thr Gln Lys Tyr Ser Gln Ser Asn Glu Ala Glu Ser Ala Tyr Leu
            100                 105                 110

Pro Gly Gly Thr Gly Trp Tyr Arg Lys Ser Phe Thr Ile Asp Arg Asp
        115                 120                 125

Leu Ala Gly Lys Arg Ile Ala Ile Asn Phe Asp Gly Val Tyr Met Asn
    130                 135                 140

Ala Thr Val Trp Phe Asn Gly Val Lys Leu Gly Thr His Pro Tyr Gly
145                 150                 155                 160

Tyr Ser Pro Phe Ser Phe Asp Leu Thr Gly Asn Ala Lys Phe Gly Gly
                165                 170                 175

Glu Asn Thr Ile Val Val Lys Val Glu Asn Arg Leu Pro Ser Ser Arg
            180                 185                 190

Trp Tyr Ser Gly Ser Gly Ile Tyr Arg Asp Val Thr Leu Thr Val Thr
        195                 200                 205

Asp Gly Val His Val Gly Asn Asn Gly Val Ala Ile Lys Thr Pro Ser
    210                 215                 220

Leu Ala Thr Gln Asn Gly Gly Asp Val Thr Met Asn Leu Thr Thr Lys
225                 230                 235                 240

Val Ala Asn Asp Thr Glu Ala Ala Ala Asn Ile Thr Leu Lys Gln Thr
                245                 250                 255

```
Val Phe Pro Lys Gly Gly Lys Thr Asp Ala Ile Gly Thr Val Thr
            260                 265                 270

Thr Ala Ser Lys Ser Ile Ala Ala Gly Ala Ser Ala Asp Val Thr Ser
            275                 280                 285

Thr Ile Thr Ala Ala Ser Pro Lys Leu Trp Ser Ile Lys Asn Pro Asn
    290                 295                 300

Leu Tyr Thr Val Arg Thr Glu Val Leu Asn Gly Gly Lys Val Leu Asp
305                 310                 315                 320

Thr Tyr Asp Thr Glu Tyr Gly Phe Arg Trp Thr Gly Phe Asp Ala Thr
                325                 330                 335

Ser Gly Phe Ser Leu Asn Gly Glu Lys Val Lys Leu Lys Gly Val Ser
            340                 345                 350

Met His His Asp Gln Gly Ser Leu Gly Ala Val Ala Asn Arg Arg Ala
        355                 360                 365

Ile Glu Arg Gln Val Glu Ile Leu Gln Lys Met Gly Val Asn Ser Ile
    370                 375                 380

Arg Thr Thr His Asn Pro Ala Ala Lys Ala Leu Ile Asp Val Cys Asn
385                 390                 395                 400

Glu Lys Gly Val Leu Val Val Glu Glu Val Phe Asp Met Trp Asn Arg
                405                 410                 415

Ser Lys Asn Gly Asn Thr Glu Asp Tyr Gly Lys Trp Phe Gln Ala
            420                 425                 430

Ile Ala Gly Asp Asn Ala Val Leu Gly Gly Asp Lys Asp Glu Thr Trp
        435                 440                 445

Ala Lys Phe Asp Leu Thr Thr Ile Asn Arg Asp Arg Asn Ala Pro
450                 455                 460

Ser Val Ile Met Trp Ser Leu Gly Asn Glu Met Met Glu Gly Ile Ser
465                 470                 475                 480

Gly Ser Val Ser Gly Phe Ser Ala Thr Ser Ala Lys Leu Val Ala Trp
            485                 490                 495

Thr Lys Ala Ala Asp Ser Thr Arg Pro Met Thr Tyr Gly Asp Asn Lys
            500                 505                 510

Ile Lys Ala Asn Trp Asn Glu Ser Asn Thr Met Gly Asp Asn Leu Thr
        515                 520                 525

Ala Asn Gly Gly Val Val Gly Thr Asn Tyr Ser Asp Gly Ala Asn Tyr
530                 535                 540

Asp Lys Ile Arg Thr Thr His Pro Ser Trp Ala Ile Tyr Gly Ser Glu
545                 550                 555                 560

Thr Ala Ser Ala Ile Asn Ser Arg Gly Ile Tyr Asn Arg Thr Thr Gly
                565                 570                 575

Gly Ala Gln Ser Ser Asp Lys Gln Leu Thr Ser Tyr Asp Asn Ser Ala
            580                 585                 590

Val Gly Trp Gly Ala Val Ala Ser Ser Ala Trp Tyr Asp Val Val Gln
        595                 600                 605

Arg Asp Phe Val Ala Gly Thr Tyr Val Trp Thr Gly Phe Asp Tyr Leu
    610                 615                 620

Gly Glu Pro Thr Pro Trp Asn Gly Thr Gly Ser Gly Ala Val Gly Ser
625                 630                 635                 640

Trp Pro Ser Pro Lys Asn Ser Tyr Phe Gly Ile Val Asp Thr Ala Gly
                645                 650                 655

Phe Pro Lys Asp Thr Tyr Tyr Phe Tyr Gln Ser Gln Trp Asn Asp Asp
            660                 665                 670
```

```
-continued

Val His Thr Leu His Ile Leu Pro Ala Trp Asn Glu Asn Val Val Ala
        675                 680                 685

Lys Gly Ser Gly Asn Asn Val Pro Val Val Tyr Thr Asp Ala Ala
690                 695                 700

Lys Val Lys Leu Tyr Phe Thr Pro Lys Gly Ser Thr Glu Gln Arg Leu
705                 710                 715                 720

Ile Gly Glu Lys Ser Phe Thr Lys Lys Thr Ala Ala Gly Tyr Thr
                725                 730                 735

Tyr Gln Val Tyr Glu Gly Ser Asp Lys Asp Ser Thr Ala His Lys Asn
                740                 745                 750

Met Tyr Leu Thr Trp Asn Val Pro Trp Ala Glu Gly Thr Ile Ser Ala
        755                 760                 765

Glu Ala Tyr Asp Glu Asn Asn Arg Leu Ile Pro Glu Gly Ser Thr Glu
770                 775                 780

Gly Asn Ala Ser Val Thr Thr Gly Lys Ala Ala Lys Leu Lys Ala
785                 790                 795                 800

Asp Ala Asp Arg Lys Thr Ile Thr Ala Asp Gly Lys Asp Leu Ser Tyr
                805                 810                 815

Ile Glu Val Asp Val Thr Asp Ala Asn Gly His Ile Val Pro Asp Ala
                820                 825                 830

Ala Asn Arg Val Thr Phe Asp Val Lys Gly Ala Gly Lys Leu Val Gly
        835                 840                 845

Val Asp Asn Gly Ser Ser Pro Asp His Asp Ser Tyr Gln Ala Asp Asn
        850                 855                 860

Arg Lys Ala Phe Ser Gly Lys Val Leu Ala Ile Val Gln Ser Thr Lys
865                 870                 875                 880

Glu Ala Gly Glu Ile Thr Val Thr Ala Lys Ala Asp Gly Leu Gln Ser
                885                 890                 895

Ser Thr Val Lys Ile Ala Thr Thr Ala Val Pro Gly Thr Ser Thr Glu
                900                 905                 910

Lys Thr Val Arg Ser Phe Tyr Tyr Ser Arg Asn Tyr Tyr Val Lys Thr
        915                 920                 925

Gly Asn Lys Pro Ile Leu Pro Ser Asp Val Glu Val Arg Tyr Ser Asp
        930                 935                 940

Gly Thr Ser Asp Arg Gln Asn Val Thr Trp Asp Ala Val Ser Asp Asp
945                 950                 955                 960

Gln Ile Ala Lys Ala Gly Ser Phe Ser Val Ala Gly Thr Val Ala Gly
                965                 970                 975

Gln Lys Ile Ser Val Arg Val Thr Met Ile Asp Glu Ile Gly Ala Leu
                980                 985                 990

Leu Asn Tyr Ser Ala Ser Thr Pro  Val Gly Thr Pro Ala  Val Leu Pro
        995                 1000                1005

Gly Ser  Arg Pro Ala Val Leu  Pro Asp Gly Thr Val  Thr Ser Ala
     1010                1015                1020

Asn Phe  Ala Val His Trp Thr  Lys Pro Ala Asp Thr  Val Tyr Asn
     1025                1030                1035

Thr Ala  Gly Thr Val Lys Val  Pro Gly Thr Ala Thr  Val Phe Gly
     1040                1045                1050

Lys Glu  Phe Lys Val Thr Ala  Thr Ile Arg Val Gln  Arg Ser Gln
     1055                1060                1065

Val Thr  Ile Gly Ser Ser Val  Ser Gly Asn Ala Leu  Arg Leu Thr
     1070                1075                1080
```

```
Gln Asn Ile Pro Ala Asp Lys Gln Ser Asp Thr Leu Asp Ala Ile
        1085                1090                1095

Lys Asp Gly Ser Thr Thr Val Asp Ala Asn Thr Gly Gly Gly Ala
    1100                1105                1110

Asn Pro Ser Ala Trp Thr Asn Trp Ala Tyr Ser Lys Ala Gly His
    1115                1120                1125

Asn Thr Ala Glu Ile Thr Phe Glu Tyr Ala Thr Glu Gln Gln Leu
    1130                1135                1140

Gly Gln Ile Val Met Tyr Phe Arg Asp Ser Asn Ala Val Arg
    1145                1150                1155

Phe Pro Asp Ala Gly Lys Thr Lys Ile Gln Ile Ser Ala Asp Gly
    1160                1165                1170

Lys Asn Trp Thr Asp Leu Ala Ala Thr Glu Thr Ile Ala Ala Gln
    1175                1180                1185

Glu Ser Ser Asp Arg Val Lys Pro Tyr Thr Tyr Asp Phe Ala Pro
    1190                1195                1200

Val Gly Ala Thr Phe Val Arg Val Thr Val Thr Asn Ala Asp Thr
    1205                1210                1215

Thr Thr Pro Ser Gly Val Val Cys Ala Gly Leu Thr Glu Ile Glu
    1220                1225                1230

Leu Lys Thr Ala Thr Ser Lys Phe Val Ala Asn Thr Ser Ala Ala
    1235                1240                1245

Leu Ser Ser Leu Thr Val Asn Gly Thr Lys Val Ser Asp Ser Val
    1250                1255                1260

Leu Ala Ala Gly Ser Tyr Asn Thr Pro Ala Ile Ile Ala Asp Val
    1265                1270                1275

Lys Ala Glu Gly Glu Gly Asn Ala Ser Val Thr Val Leu Pro Ala
    1280                1285                1290

His Asp Asn Val Ile Arg Val Ile Thr Glu Ser Glu Asp His Val
    1295                1300                1305

Thr Arg Lys Thr Phe Thr Ile Asn Leu Gly Thr Glu Gln Glu Phe
    1310                1315                1320

Pro Ala Asp Ser Asp Glu Arg Asp Gln His Gln His Gln His Gln
    1325                1330                1335

His Gln Gln
    1340

<210> SEQ ID NO 4
<211> LENGTH: 1752
<212> TYPE: PRT
<213> ORGANISM: Artificial sequence
<220> FEATURE:
<223> OTHER INFORMATION: Synthetic construct

<400> SEQUENCE: 4

Met Ala Val Arg Arg Leu Gly Gly Arg Ile Val Ala Phe Ala Ala Thr
1               5                   10                  15

Val Ala Leu Ser Ile Pro Leu Gly Leu Leu Thr Asn Ser Ala Trp Ala
                20                  25                  30

Val Glu Asp Ala Thr Arg Ser Asp Ser Thr Thr Gln Met Ser Ser Thr
            35                  40                  45

Pro Glu Val Val Tyr Ser Ser Ala Val Asp Ser Lys Gln Asn Arg Thr
        50                  55                  60

Ser Asp Phe Asp Ala Asn Trp Lys Phe Met Leu Ser Asp Ser Val Gln
65                  70                  75                  80
```

Ala Gln Asp Pro Ala Phe Asp Ser Ala Trp Gln Val Asp Leu
             85                  90                  95

Pro His Asp Tyr Ser Ile Thr Gln Lys Tyr Ser Gln Ser Asn Glu Ala
                100                 105                 110

Glu Ser Ala Tyr Leu Pro Gly Gly Thr Gly Trp Tyr Arg Lys Ser Phe
            115                 120                 125

Thr Ile Asp Arg Asp Leu Ala Gly Lys Arg Ile Ala Ile Asn Phe Asp
130                 135                 140

Gly Val Tyr Met Asn Ala Thr Val Trp Phe Asn Gly Val Lys Leu Gly
145                 150                 155                 160

Thr His Pro Tyr Gly Tyr Ser Pro Phe Ser Phe Asp Leu Thr Gly Asn
                165                 170                 175

Ala Lys Phe Gly Gly Glu Asn Thr Ile Val Val Lys Val Glu Asn Arg
            180                 185                 190

Leu Pro Ser Ser Arg Trp Tyr Ser Gly Ser Gly Ile Tyr Arg Asp Val
        195                 200                 205

Thr Leu Thr Val Thr Asp Gly Val His Val Gly Asn Asn Gly Val Ala
210                 215                 220

Ile Lys Thr Pro Ser Leu Ala Thr Gln Asn Gly Gly Asp Val Thr Met
225                 230                 235                 240

Asn Leu Thr Thr Lys Val Ala Asn Asp Thr Glu Ala Ala Ala Asn Ile
                245                 250                 255

Thr Leu Lys Gln Thr Val Phe Pro Lys Gly Gly Lys Thr Asp Ala Ala
            260                 265                 270

Ile Gly Thr Val Thr Ala Ser Lys Ser Ile Ala Ala Gly Ala Ser
        275                 280                 285

Ala Asp Val Thr Ser Thr Ile Thr Ala Ala Ser Pro Lys Leu Trp Ser
            290                 295                 300

Ile Lys Asn Pro Asn Leu Tyr Thr Val Arg Thr Glu Val Leu Asn Gly
305                 310                 315                 320

Gly Lys Val Leu Asp Thr Tyr Asp Thr Glu Tyr Gly Phe Arg Trp Thr
                325                 330                 335

Gly Phe Asp Ala Thr Ser Gly Phe Ser Leu Asn Gly Glu Lys Val Lys
            340                 345                 350

Leu Lys Gly Val Ser Met His His Asp Gln Gly Ser Leu Gly Ala Val
        355                 360                 365

Ala Asn Arg Arg Ala Ile Glu Arg Gln Val Glu Ile Leu Gln Lys Met
370                 375                 380

Gly Val Asn Ser Ile Arg Thr Thr His Asn Pro Ala Ala Lys Ala Leu
385                 390                 395                 400

Ile Asp Val Cys Asn Glu Lys Gly Val Leu Val Val Glu Glu Val Phe
                405                 410                 415

Asp Met Trp Asn Arg Ser Lys Asn Gly Asn Thr Glu Asp Tyr Gly Lys
            420                 425                 430

Trp Phe Gly Gln Ala Ile Ala Gly Asp Asn Ala Val Leu Gly Gly Asp
        435                 440                 445

Lys Asp Glu Thr Trp Ala Lys Phe Asp Leu Thr Ser Thr Ile Asn Arg
450                 455                 460

Asp Arg Asn Ala Pro Ser Val Ile Met Trp Ser Leu Gly Asn Glu Met
465                 470                 475                 480

Met Glu Gly Ile Ser Gly Ser Val Ser Gly Phe Pro Ala Thr Ser Ala
                485                 490                 495

-continued

```
Lys Leu Val Ala Trp Thr Lys Ala Ala Asp Ser Thr Arg Pro Met Thr
                500                 505                 510
Tyr Gly Asp Asn Lys Ile Lys Ala Asn Trp Asn Glu Ser Asn Thr Met
            515                 520                 525
Gly Asp Asn Leu Thr Ala Asn Gly Val Val Gly Thr Asn Tyr Ser
        530                 535                 540
Asp Gly Ala Asn Tyr Asp Lys Ile Arg Thr Thr His Pro Ser Trp Ala
545                 550                 555                 560
Ile Tyr Gly Ser Glu Thr Ala Ser Ala Ile Asn Ser Arg Gly Ile Tyr
                565                 570                 575
Asn Arg Thr Thr Gly Gly Ala Gln Ser Ser Asp Lys Gln Leu Thr Ser
            580                 585                 590
Tyr Asp Asn Ser Ala Val Gly Trp Gly Ala Val Ala Ser Ser Ala Trp
        595                 600                 605
Tyr Asp Val Val Gln Arg Asp Phe Val Ala Gly Thr Tyr Val Trp Thr
    610                 615                 620
Gly Phe Asp Tyr Leu Gly Glu Pro Thr Pro Trp Asn Gly Thr Gly Ser
625                 630                 635                 640
Gly Ala Val Gly Ser Trp Pro Ser Pro Lys Asn Ser Tyr Phe Gly Ile
                645                 650                 655
Val Asp Thr Ala Gly Phe Pro Lys Asp Thr Tyr Tyr Phe Tyr Gln Ser
            660                 665                 670
Gln Trp Asn Asp Asp Val His Thr Leu His Ile Leu Pro Ala Trp Asn
        675                 680                 685
Glu Asn Val Val Ala Lys Gly Ser Gly Asn Asn Val Pro Val Val Val
    690                 695                 700
Tyr Thr Asp Ala Ala Lys Val Lys Leu Tyr Phe Thr Pro Lys Gly Ser
705                 710                 715                 720
Thr Glu Lys Arg Leu Ile Gly Glu Lys Ser Phe Thr Lys Lys Thr Thr
                725                 730                 735
Ala Ala Gly Tyr Thr Tyr Gln Val Tyr Glu Gly Ser Asp Lys Asp Ser
            740                 745                 750
Thr Ala His Lys Asn Met Tyr Leu Thr Trp Asn Val Pro Trp Ala Glu
        755                 760                 765
Gly Thr Ile Ser Ala Glu Ala Tyr Asp Glu Asn Asn Arg Leu Ile Pro
    770                 775                 780
Glu Gly Ser Thr Glu Gly Asn Ala Ser Val Thr Thr Gly Lys Ala
785                 790                 795                 800
Ala Lys Leu Lys Ala Asp Ala Asp Arg Lys Thr Ile Thr Ala Asp Gly
                805                 810                 815
Lys Asp Leu Ser Tyr Ile Glu Val Asp Val Thr Asp Ala Asn Gly His
            820                 825                 830
Ile Val Pro Asp Ala Ala Asn Arg Val Thr Phe Asp Val Lys Gly Ala
        835                 840                 845
Gly Lys Leu Val Gly Val Asp Asn Gly Ser Ser Pro Asp His Asp Ser
    850                 855                 860
Tyr Gln Ala Asp Asn Arg Lys Ala Phe Ser Gly Lys Val Leu Ala Ile
865                 870                 875                 880
Val Gln Ser Thr Lys Glu Ala Gly Glu Ile Thr Val Thr Ala Lys Ala
                885                 890                 895
Asp Gly Leu Gln Ser Ser Thr Val Lys Ile Ala Thr Thr Ala Val Pro
            900                 905                 910
```

-continued

Gly Thr Ser Thr Glu Lys Thr Val Arg Ser Phe Tyr Tyr Ser Arg Asn
            915                 920                 925

Tyr Tyr Val Lys Thr Gly Asn Lys Pro Ile Leu Pro Ser Asp Val Glu
        930                 935                 940

Val Arg Tyr Ser Asp Gly Thr Ser Asp Arg Gln Asn Val Thr Trp Asp
945                 950                 955                 960

Ala Val Ser Asp Asp Gln Ile Ala Lys Ala Gly Ser Phe Ser Val Ala
                965                 970                 975

Gly Thr Val Ala Gly Gln Lys Ile Ser Val Arg Val Thr Met Ile Asp
            980                 985                 990

Glu Ile Gly Ala Leu Leu Asn Tyr Ser Ala Ser Thr Pro Val Gly Thr
        995                 1000                1005

Pro Ala Val Leu Pro Gly Ser Arg Pro Ala Val Leu Pro Asp Gly
    1010                1015                1020

Thr Val Thr Ser Ala Asn Phe Ala Val His Trp Thr Lys Pro Ala
    1025                1030                1035

Asp Thr Val Tyr Asn Thr Ala Gly Thr Val Lys Val Pro Gly Thr
    1040                1045                1050

Ala Thr Val Phe Gly Lys Glu Phe Lys Val Thr Ala Thr Ile Arg
    1055                1060                1065

Val Gln Arg Ser Gln Val Thr Ile Gly Ser Ser Val Ser Gly Asn
    1070                1075                1080

Ala Leu Arg Leu Thr Gln Asn Ile Pro Ala Asp Lys Gln Ser Asp
    1085                1090                1095

Thr Leu Asp Ala Ile Lys Asp Gly Ser Thr Thr Val Asp Ala Asn
    1100                1105                1110

Thr Gly Gly Gly Ala Asn Pro Ser Ala Trp Thr Asn Trp Ala Tyr
    1115                1120                1125

Ser Lys Ala Gly His Asn Thr Ala Glu Ile Thr Phe Glu Tyr Ala
    1130                1135                1140

Thr Glu Gln Gln Leu Gly Gln Ile Val Met Tyr Phe Phe Arg Asp
    1145                1150                1155

Ser Asn Ala Val Arg Phe Pro Asp Ala Gly Lys Thr Lys Ile Gln
    1160                1165                1170

Ile Ser Ala Asp Gly Lys Asn Trp Thr Asp Leu Ala Ala Thr Glu
    1175                1180                1185

Thr Ile Ala Ala Gln Glu Ser Ser Asp Arg Val Lys Pro Tyr Thr
    1190                1195                1200

Tyr Asp Phe Ala Pro Val Gly Ala Thr Phe Val Lys Val Thr Val
    1205                1210                1215

Thr Asn Ala Asp Thr Thr Pro Ser Gly Val Val Cys Ala Gly
    1220                1225                1230

Leu Thr Glu Ile Glu Leu Lys Thr Ala Thr Ser Lys Phe Val Thr
    1235                1240                1245

Asn Thr Ser Ala Ala Leu Ser Ser Leu Thr Val Asn Gly Thr Lys
    1250                1255                1260

Val Ser Asp Ser Val Leu Ala Ala Gly Ser Tyr Asn Thr Pro Ala
    1265                1270                1275

Ile Ile Ala Asp Val Lys Ala Glu Gly Glu Gly Asn Ala Ser Val
    1280                1285                1290

Thr Val Leu Pro Ala His Asp Asn Val Ile Arg Val Ile Thr Glu
    1295                1300                1305

```
Ser Glu Asp His Val Thr Arg Lys Thr Phe Thr Ile Asn Leu Gly
    1310                1315                1320

Thr Glu Gln Glu Phe Pro Ala Asp Ser Asp Glu Arg Asp Tyr Pro
    1325                1330                1335

Ala Ala Asp Met Thr Val Thr Val Gly Ser Glu Gln Thr Ser Gly
    1340                1345                1350

Thr Ala Thr Glu Gly Pro Lys Lys Phe Ala Val Asp Gly Asn Thr
    1355                1360                1365

Ser Thr Tyr Trp His Ser Asn Trp Thr Pro Thr Thr Val Asn Asp
    1370                1375                1380

Leu Trp Ile Ala Phe Glu Leu Gln Lys Pro Thr Lys Leu Asp Ala
    1385                1390                1395

Leu Arg Tyr Leu Pro Arg Pro Ala Gly Ser Lys Asn Gly Ser Val
    1400                1405                1410

Thr Glu Tyr Lys Val Gln Val Ser Asp Asp Gly Thr Asn Trp Thr
    1415                1420                1425

Asp Ala Gly Ser Gly Thr Trp Thr Thr Asp Tyr Gly Trp Lys Leu
    1430                1435                1440

Ala Glu Phe Asn Gln Pro Val Thr Thr Lys His Val Arg Leu Lys
    1445                1450                1455

Ala Val His Thr Tyr Ala Asp Ser Gly Asn Asp Lys Phe Met Ser
    1460                1465                1470

Ala Ser Glu Ile Arg Leu Arg Lys Ala Val Asp Thr Thr Asp Ile
    1475                1480                1485

Ser Gly Ala Thr Val Thr Val Pro Ala Lys Leu Thr Val Asp Arg
    1490                1495                1500

Val Asp Ala Asp His Pro Ala Thr Phe Ala Thr Lys Asp Val Thr
    1505                1510                1515

Val Thr Leu Gly Asp Ala Thr Leu Arg Tyr Gly Val Asp Tyr Leu
    1520                1525                1530

Leu Asp Tyr Ala Gly Asn Thr Ala Val Gly Lys Ala Thr Val Thr
    1535                1540                1545

Val Arg Gly Ile Asp Lys Tyr Ser Gly Thr Val Ala Lys Thr Phe
    1550                1555                1560

Thr Ile Glu Leu Lys Asn Ala Pro Ala Pro Glu Pro Thr Leu Thr
    1565                1570                1575

Ser Val Ser Val Lys Thr Lys Pro Ser Lys Leu Thr Tyr Val Val
    1580                1585                1590

Gly Asp Ala Phe Asp Pro Ala Gly Leu Val Leu Gln His Asp Arg
    1595                1600                1605

Gln Ala Asp Arg Pro Pro Gln Pro Leu Val Gly Glu Gln Ala Asp
    1610                1615                1620

Glu Arg Gly Leu Thr Cys Gly Thr Arg Cys Asp Arg Val Glu Gln
    1625                1630                1635

Leu Arg Lys His Glu Asn Arg Glu Ala His Arg Thr Gly Leu Asp
    1640                1645                1650

His Leu Glu Phe Val Gly Ala Ala Asp Gly Ala Val Gly Glu Gln
    1655                1660                1665

Ala Thr Phe Lys Val His Val His Ala Asp Gln Gly Asp Gly Arg
    1670                1675                1680

His Asp Asp Ala Asp Glu Arg Asp Ile Asp Pro His Val Pro Val
    1685                1690                1695
```

Asp His Ala Val Gly Glu Leu Ala Arg Ala Ala Cys His His Val
    1700                1705                1710

Ile Gly Leu Arg Val Asp Thr His Arg Leu Lys Ala Ser Gly Phe
    1715                1720                1725

Gln Ile Pro Ala Asp Asp Met Ala Glu Ile Asp Arg Ile Thr Gly
    1730                1735                1740

Phe His Arg Phe Glu Arg His Val Gly
    1745                1750

<210> SEQ ID NO 5
<211> LENGTH: 1935
<212> TYPE: PRT
<213> ORGANISM: Artificial sequence
<220> FEATURE:
<223> OTHER INFORMATION: Synthetic construct

<400> SEQUENCE: 5

Met Ala Val Arg Arg Leu Gly Gly Arg Ile Val Ala Phe Ala Ala Thr
1               5                   10                  15

Val Ala Leu Ser Ile Pro Leu Gly Leu Leu Thr Asn Ser Ala Trp Ala
                20                  25                  30

Val Glu Asp Ala Thr Arg Ser Asp Ser Thr Thr Gln Met Ser Ser Thr
            35                  40                  45

Pro Glu Val Val Tyr Ser Ser Ala Val Asp Ser Lys Gln Asn Arg Thr
        50                  55                  60

Ser Asp Phe Asp Ala Asn Trp Lys Phe Met Leu Ser Asp Ser Val Gln
65                  70                  75                  80

Ala Gln Asp Pro Ala Phe Asp Ser Ala Trp Gln Val Asp Leu
                85                  90                  95

Pro His Asp Tyr Ser Ile Thr Gln Lys Tyr Ser Gln Ser Asn Glu Ala
                100                 105                 110

Glu Ser Ala Tyr Leu Pro Gly Gly Thr Gly Trp Tyr Arg Lys Ser Phe
            115                 120                 125

Thr Ile Asp Arg Asp Leu Ala Gly Lys Arg Ile Ala Ile Asn Phe Asp
        130                 135                 140

Gly Val Tyr Met Asn Ala Thr Val Trp Phe Asn Gly Val Lys Leu Gly
145                 150                 155                 160

Thr His Pro Tyr Gly Tyr Ser Pro Phe Ser Phe Asp Leu Thr Gly Asn
                165                 170                 175

Ala Lys Phe Gly Gly Glu Asn Thr Ile Val Val Lys Val Glu Asn Arg
            180                 185                 190

Leu Pro Ser Ser Arg Trp Tyr Ser Gly Ser Gly Ile Tyr Arg Asp Val
        195                 200                 205

Thr Leu Thr Val Thr Asp Gly Val His Val Gly Asn Asn Gly Val Ala
        210                 215                 220

Ile Lys Thr Pro Ser Leu Ala Thr Gln Asn Gly Gly Asn Val Thr Met
225                 230                 235                 240

Asn Leu Thr Thr Lys Val Ala Asn Asp Thr Lys Ala Ala Ala Asn Ile
                245                 250                 255

Thr Leu Lys Gln Thr Val Phe Pro Lys Gly Gly Lys Thr Asp Ala Ala
            260                 265                 270

Ile Gly Thr Val Thr Thr Ala Ser Lys Ser Ile Ala Ala Gly Ala Ser
        275                 280                 285

Ala Asp Val Thr Ser Thr Ile Thr Ala Ala Ser Pro Lys Leu Trp Ser
        290                 295                 300

```
Ile Lys Asn Pro Asn Leu Tyr Thr Val Arg Thr Glu Val Leu Asn Gly
305                 310                 315                 320

Gly Lys Val Leu Asp Thr Tyr Asp Thr Glu Tyr Gly Phe Arg Trp Thr
                325                 330                 335

Gly Phe Asp Ala Thr Ser Gly Phe Ser Leu Asn Gly Glu Lys Val Lys
            340                 345                 350

Leu Lys Gly Val Ser Met His His Asp Gln Gly Ser Leu Gly Ala Val
        355                 360                 365

Ala Asn Arg Arg Ala Ile Glu Arg Gln Val Glu Ile Leu Gln Lys Met
370                 375                 380

Gly Val Asn Ser Ile Arg Thr Thr His Asn Pro Ala Ala Lys Ala Leu
385                 390                 395                 400

Ile Asp Val Cys Asn Glu Lys Gly Val Leu Val Val Glu Glu Val Phe
                405                 410                 415

Asp Met Trp Asn Arg Ser Lys Asn Gly Asn Thr Glu Asp Tyr Gly Lys
            420                 425                 430

Trp Phe Gly Gln Ala Ile Ala Gly Asp Asn Ala Val Leu Gly Gly Asp
        435                 440                 445

Lys Asp Glu Thr Trp Ala Lys Phe Asp Leu Thr Ser Thr Ile Asn Arg
450                 455                 460

Asp Arg Asn Ala Pro Ser Val Ile Met Trp Ser Leu Gly Asn Glu Met
465                 470                 475                 480

Met Glu Gly Ile Ser Gly Ser Val Ser Gly Phe Pro Ala Thr Ser Ala
                485                 490                 495

Lys Leu Val Ala Trp Thr Lys Ala Ala Asp Ser Thr Arg Pro Met Thr
            500                 505                 510

Tyr Gly Asp Asn Lys Ile Lys Ala Asn Trp Asn Glu Ser Asn Thr Met
        515                 520                 525

Gly Asp Asn Leu Thr Ala Asn Gly Gly Val Val Gly Thr Asn Tyr Ser
530                 535                 540

Asp Gly Ala Asn Tyr Asp Lys Ile Arg Thr Thr His Pro Ser Trp Ala
545                 550                 555                 560

Ile Tyr Gly Ser Glu Thr Ala Ser Ala Ile Asn Ser Arg Gly Ile Tyr
                565                 570                 575

Asn Arg Thr Thr Gly Gly Ala Gln Ser Ser Asp Lys Gln Leu Thr Ser
            580                 585                 590

Tyr Asp Asn Ser Ala Val Gly Trp Gly Ala Val Ala Ser Ser Ala Trp
        595                 600                 605

Tyr Asp Val Val Gln Arg Asp Phe Val Ala Gly Thr Tyr Val Trp Thr
610                 615                 620

Gly Phe Asp Tyr Leu Gly Glu Pro Thr Pro Trp Asn Gly Thr Gly Ser
625                 630                 635                 640

Gly Ala Val Gly Ser Trp Pro Ser Pro Lys Asn Ser Tyr Phe Gly Ile
                645                 650                 655

Val Asp Thr Ala Gly Phe Pro Lys Asp Thr Tyr Tyr Phe Tyr Gln Ser
            660                 665                 670

Gln Trp Asn Asp Asp Val His Thr Leu His Ile Leu Pro Ala Trp Asn
        675                 680                 685

Glu Asn Val Val Ala Lys Gly Ser Gly Asn Asn Val Pro Val Val Val
690                 695                 700

Tyr Thr Asp Ala Ala Lys Val Lys Leu Tyr Phe Thr Pro Lys Gly Ser
705                 710                 715                 720
```

-continued

Thr Glu Lys Arg Leu Ile Gly Glu Lys Ser Phe Thr Lys Thr Thr
         725                 730                 735

Ala Ala Gly Tyr Thr Tyr Gln Val Tyr Glu Gly Ala Asp Lys Asp Ser
         740                 745                 750

Thr Ala His Lys Asn Met Tyr Leu Thr Trp Asn Val Pro Trp Ala Glu
         755                 760                 765

Gly Thr Ile Ser Ala Glu Ala Tyr Asp Glu Asn Asn Arg Leu Ile Pro
         770                 775                 780

Glu Gly Ser Thr Glu Gly Asn Ala Ser Val Thr Thr Gly Lys Ala
785                 790                 795                 800

Ala Lys Leu Lys Ala Asp Ala Asp Arg Lys Thr Ile Thr Ala Asp Gly
                 805                 810                 815

Lys Asp Leu Ser Tyr Ile Glu Val Asp Val Thr Asp Ala Asn Gly His
                 820                 825                 830

Ile Val Pro Asp Ala Ala Asn Arg Val Thr Phe Asp Val Lys Gly Ala
                 835                 840                 845

Gly Lys Leu Val Gly Val Asp Asn Gly Ser Ser Pro Asp His Asp Ser
                 850                 855                 860

Tyr Gln Ala Asp Asn Arg Lys Ala Phe Ser Gly Lys Val Leu Ala Ile
865                 870                 875                 880

Val Gln Ser Thr Lys Glu Ala Gly Glu Ile Thr Val Thr Ala Lys Ala
                 885                 890                 895

Asp Gly Leu Gln Ser Ser Thr Val Lys Ile Ala Thr Thr Ala Val Pro
                 900                 905                 910

Gly Thr Ser Thr Glu Lys Thr Val Arg Ser Phe Tyr Tyr Ser Arg Asn
                 915                 920                 925

Tyr Tyr Val Lys Thr Gly Asn Lys Pro Ile Leu Pro Ser Asp Val Glu
                 930                 935                 940

Val Arg Tyr Ser Asp Gly Thr Ser Asp Arg Gln Asn Val Thr Trp Asp
945                 950                 955                 960

Ala Val Ser Asp Asp Gln Ile Ala Lys Ala Gly Ser Phe Ser Val Ala
                 965                 970                 975

Gly Thr Val Ala Gly Gln Lys Ile Ser Val Arg Val Thr Met Ile Asp
                 980                 985                 990

Glu Ile Gly Ala Leu Leu Asn Tyr Ser Ala Ser Thr Pro Val Gly Thr
                 995                 1000                1005

Pro Ala Val Leu Pro Gly Ser Arg Pro Ala Val Leu Pro Asp Gly
        1010                1015                1020

Thr Val Thr Ser Ala Asn Phe Ala Val Asp Trp Thr Lys Pro Ala
        1025                1030                1035

Asp Thr Val Tyr Asn Thr Ala Gly Thr Val Lys Val Pro Gly Thr
        1040                1045                1050

Ala Thr Val Phe Gly Lys Glu Phe Lys Val Thr Ala Thr Ile Arg
        1055                1060                1065

Val Gln Arg Ser Gln Val Thr Ile Gly Ser Ser Val Ser Gly Asn
        1070                1075                1080

Ala Leu Arg Leu Thr Gln Asn Ile Pro Ala Asp Lys Gln Ser Asp
        1085                1090                1095

Thr Leu Asp Ala Ile Lys Asp Gly Ser Thr Thr Val Asp Ala Asn
        1100                1105                1110

Thr Gly Gly Gly Ala Asn Pro Ser Ala Trp Thr Asn Trp Ala Tyr
        1115                1120                1125

```
Ser Lys Ala Gly His Asn Thr Ala Glu Ile Thr Phe Glu Tyr Ala
    1130            1135                1140

Thr Glu Gln Gln Leu Gly Gln Ile Val Met Tyr Phe Phe Arg Asp
    1145            1150                1155

Ser Asn Ala Val Arg Phe Pro Asp Ala Gly Lys Thr Lys Ile Gln
    1160            1165                1170

Ile Ser Ala Asp Gly Lys Asn Trp Thr Asp Leu Ala Ala Thr Glu
    1175            1180                1185

Thr Ile Ala Ala Gln Glu Ser Ser Asp Arg Val Lys Pro Tyr Thr
    1190            1195                1200

Tyr Asp Phe Ala Pro Val Gly Ala Thr Phe Val Lys Val Thr Val
    1205            1210                1215

Thr Asn Ala Asp Thr Thr Thr Pro Ser Gly Val Val Cys Ala Gly
    1220            1225                1230

Leu Thr Glu Ile Glu Leu Lys Thr Ala Thr Ser Lys Phe Val Thr
    1235            1240                1245

Asn Thr Ser Ala Ala Leu Ser Ser Leu Thr Val Asn Gly Thr Lys
    1250            1255                1260

Val Ser Asp Ser Val Leu Ala Ala Gly Ser Tyr Asn Thr Pro Ala
    1265            1270                1275

Ile Ile Ala Asp Val Lys Ala Glu Gly Glu Gly Asn Ala Ser Val
    1280            1285                1290

Thr Val Leu Pro Ala His Asp Asn Val Ile Arg Val Ile Thr Glu
    1295            1300                1305

Ser Glu Asp His Val Thr Arg Lys Thr Phe Thr Ile Asn Leu Gly
    1310            1315                1320

Thr Glu Gln Glu Phe Pro Ala Asp Ser Asp Glu Arg Asp Tyr Pro
    1325            1330                1335

Ala Ala Asp Met Thr Val Thr Ala Gly Ser Glu Gln Thr Ser Gly
    1340            1345                1350

Thr Ala Thr Glu Gly Pro Lys Lys Phe Ala Val Asp Gly Asn Thr
    1355            1360                1365

Ser Thr Tyr Trp His Ser Asn Trp Thr Pro Thr Thr Val Asn Asp
    1370            1375                1380

Leu Trp Ile Ala Phe Glu Leu Gln Lys Pro Thr Lys Leu Asp Ala
    1385            1390                1395

Leu Arg Tyr Leu Pro Arg Pro Ala Gly Ser Lys Asn Gly Ser Val
    1400            1405                1410

Thr Glu Tyr Lys Val Gln Val Ser Asp Asp Gly Thr Asn Trp Thr
    1415            1420                1425

Asp Ala Gly Ser Gly Thr Trp Thr Thr Asp Tyr Gly Trp Lys Leu
    1430            1435                1440

Ala Glu Phe Asn Gln Pro Val Thr Thr Lys His Val Arg Leu Lys
    1445            1450                1455

Ala Val His Thr Tyr Ala Asp Ser Gly Asn Asp Lys Phe Met Ser
    1460            1465                1470

Ala Ser Glu Ile Arg Leu Arg Lys Ala Val Asp Thr Thr Asp Ile
    1475            1480                1485

Ser Gly Ala Thr Val Thr Val Pro Ala Lys Leu Thr Val Asp Arg
    1490            1495                1500

Val Asp Ala Asp His Pro Ala Thr Phe Ala Thr Lys Asp Val Thr
    1505            1510                1515
```

```
Val Thr Leu Gly Asp Ala Thr Leu Arg Tyr Gly Val Asp Tyr Leu
1520                1525                1530

Leu Asp Tyr Ala Gly Asn Thr Ala Val Gly Lys Ala Thr Val Thr
1535                1540                1545

Val Arg Gly Ile Asp Lys Tyr Ser Gly Thr Val Ala Lys Thr Phe
1550                1555                1560

Thr Ile Glu Leu Lys Asn Ala Pro Ala Pro Glu Pro Thr Leu Thr
1565                1570                1575

Ser Val Ser Val Lys Thr Lys Pro Ser Lys Leu Thr Tyr Val Val
1580                1585                1590

Gly Asp Ala Phe Asp Pro Ala Gly Leu Val Leu Gln Leu Asn Tyr
1595                1600                1605

Asp Asp Asp Ser Thr Gly Thr Val Thr Trp Asn Thr Gln Thr Ala
1610                1615                1620

Gly Asp Phe Thr Phe Lys Pro Ala Leu Asp Ala Lys Leu Lys Val
1625                1630                1635

Thr Asp Lys Thr Val Thr Val Thr Tyr Gln Gly Lys Ser Ala Val
1640                1645                1650

Ile Asp Ile Thr Val Ser Gln Pro Ala Pro Thr Val Ser Lys Thr
1655                1660                1665

Asp Leu Asp Lys Ala Ile Lys Ala Ile Glu Ala Lys Asn Pro Asp
1670                1675                1680

Ser Ser Lys Tyr Thr Ala Asp Ser Trp Lys Thr Phe Ala Asp Ala
1685                1690                1695

Met Ala His Ala Lys Ala Val Ile Ala Asp Asp Ser Ala Thr Gln
1700                1705                1710

Gln Asp Val Asp Lys Ala Leu Lys Ala Leu Thr Asp Ala Tyr Ala
1715                1720                1725

Gly Leu Thr Glu Lys Thr Pro Glu Pro Ala Pro Val Ser Lys Ser
1730                1735                1740

Glu Leu Asp Lys Lys Ile Lys Ala Ile Glu Ala Glu Lys Leu Asp
1745                1750                1755

Gly Ser Lys Tyr Thr Ala Glu Ser Trp Lys Ala Phe Glu Thr Ala
1760                1765                1770

Leu Ala His Ala Lys Ala Val Ile Ala Ser Asp Ser Ala Thr Gln
1775                1780                1785

Gln Asp Val Asp Ala Ala Leu Gly Ala Leu Thr Ser Ala Arg Asp
1790                1795                1800

Gly Leu Thr Glu Lys Gly Glu Val Lys Pro Asp Pro Lys Pro Glu
1805                1810                1815

Pro Gly Thr Val Asp Lys Ala Ala Leu Asp Lys Ala Val Lys Lys
1820                1825                1830

Val Glu Ala Glu Lys Leu Asp Gly Ser Lys Tyr Thr Ala Asp Ser
1835                1840                1845

Trp Lys Ala Phe Glu Thr Ala Leu Ala His Ala Lys Ala Val Ile
1850                1855                1860

Gly Asn Ala Asn Ser Thr Gln Phe Asp Ile Asp Asn Ala Leu Ser
1865                1870                1875

Met Leu Asn Asp Ala Arg Ala Ala Leu Lys Glu Lys Pro Gly Arg
1880                1885                1890

Ile Ile Ala Ile Ile Asp Gly Gly Ala Leu Ser Lys Thr Gly Ala
1895                1900                1905
```

```
Ser Val Ala Ile Ile Ala Ser Val Ala Ala Ala Met Lys Ala Val
    1910                1915                1920

Gly Ala Gly Val Met Ala Leu Arg Pro Pro Lys Trp
    1925                1930                1935
```

<210> SEQ ID NO 6
<211> LENGTH: 887
<212> TYPE: PRT
<213> ORGANISM: Bifidobacterium bifidum

<400> SEQUENCE: 6

```
Val Glu Asp Ala Thr Arg Ser Asp Ser Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335
```

-continued

```
Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
                355                 360                 365

Ile Asp Val Cys Asn Glu Lys Gly Val Leu Val Glu Glu Val Phe
            370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
                420                 425                 430

Asp Arg Asn Ala Pro Ser Val Ile Met Trp Ser Leu Gly Asn Glu Met
                435                 440                 445

Met Glu Gly Ile Ser Gly Ser Val Ser Gly Phe Pro Ala Thr Ser Ala
                450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
                500                 505                 510

Asp Gly Ala Asn Tyr Asp Lys Ile Arg Thr Thr His Pro Ser Trp Ala
                515                 520                 525

Ile Tyr Gly Ser Glu Thr Ala Ser Ala Ile Asn Ser Arg Gly Ile Tyr
                530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
                595                 600                 605

Gly Ala Val Gly Ser Trp Pro Ser Pro Lys Asn Ser Tyr Phe Gly Ile
                610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
                675                 680                 685

Thr Glu Lys Arg Leu Ile Gly Glu Lys Ser Phe Thr Lys Lys Thr Thr
                690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
                740                 745                 750
```

```
Glu Gly Ser Thr Glu Gly Asn Ala Ser Val Thr Thr Gly Lys Ala
            755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr
                885

<210> SEQ ID NO 7
<211> LENGTH: 965
<212> TYPE: PRT
<213> ORGANISM: Bifidobacterium bifidum

<400> SEQUENCE: 7

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
210                 215                 220

Thr Leu Lys Gln Thr Val Phe Pro Lys Gly Gly Lys Thr Asp Ala Ala
225                 230                 235                 240
```

```
Ile Gly Thr Val Thr Thr Ala Ser Lys Ser Ile Ala Ala Gly Ala Ser
            245                 250                 255
Ala Asp Val Thr Ser Thr Ile Thr Ala Ala Ser Pro Lys Leu Trp Ser
            260                 265                 270
Ile Lys Asn Pro Asn Leu Tyr Thr Val Arg Thr Glu Val Leu Asn Gly
            275                 280                 285
Gly Lys Val Leu Asp Thr Tyr Asp Thr Glu Tyr Gly Phe Arg Trp Thr
        290                 295                 300
Gly Phe Asp Ala Thr Ser Gly Phe Ser Leu Asn Gly Glu Lys Val Lys
305                 310                 315                 320
Leu Lys Gly Val Ser Met His His Asp Gln Gly Ser Leu Gly Ala Val
                325                 330                 335
Ala Asn Arg Arg Ala Ile Glu Arg Gln Val Glu Ile Leu Gln Lys Met
            340                 345                 350
Gly Val Asn Ser Ile Arg Thr Thr His Asn Pro Ala Ala Lys Ala Leu
            355                 360                 365
Ile Asp Val Cys Asn Glu Lys Gly Val Leu Val Glu Glu Val Phe
        370                 375                 380
Asp Met Trp Asn Arg Ser Lys Asn Gly Asn Thr Glu Asp Tyr Gly Lys
385                 390                 395                 400
Trp Phe Gly Gln Ala Ile Ala Gly Asp Asn Ala Val Leu Gly Gly Asp
                405                 410                 415
Lys Asp Glu Thr Trp Ala Lys Phe Asp Leu Thr Ser Thr Ile Asn Arg
            420                 425                 430
Asp Arg Asn Ala Pro Ser Val Ile Met Trp Ser Leu Gly Asn Glu Met
            435                 440                 445
Met Glu Gly Ile Ser Gly Ser Val Ser Gly Phe Pro Ala Thr Ser Ala
        450                 455                 460
Lys Leu Val Ala Trp Thr Lys Ala Ala Asp Ser Thr Arg Pro Met Thr
465                 470                 475                 480
Tyr Gly Asp Asn Lys Ile Lys Ala Asn Trp Asn Glu Ser Asn Thr Met
                485                 490                 495
Gly Asp Asn Leu Thr Ala Asn Gly Gly Val Val Gly Thr Asn Tyr Ser
            500                 505                 510
Asp Gly Ala Asn Tyr Asp Lys Ile Arg Thr Thr His Pro Ser Trp Ala
            515                 520                 525
Ile Tyr Gly Ser Glu Thr Ala Ser Ala Ile Asn Ser Arg Gly Ile Tyr
        530                 535                 540
Asn Arg Thr Thr Gly Gly Ala Gln Ser Ser Asp Lys Gln Leu Thr Ser
545                 550                 555                 560
Tyr Asp Asn Ser Ala Val Gly Trp Gly Ala Val Ala Ser Ser Ala Trp
                565                 570                 575
Tyr Asp Val Val Gln Arg Asp Phe Val Ala Gly Thr Tyr Val Trp Thr
            580                 585                 590
Gly Phe Asp Tyr Leu Gly Glu Pro Thr Pro Trp Asn Gly Thr Gly Ser
        595                 600                 605
Gly Ala Val Gly Ser Trp Pro Ser Pro Lys Asn Ser Tyr Phe Gly Ile
        610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
                645                 650                 655
```

Glu Asn Val Val Ala Lys Gly Ser Gly Asn Asn Val Pro Val Val
                660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
        690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
930                 935                 940

Gly Thr Val Ala Gly Gln Lys Ile Ser Val Arg Val Thr Met Ile Asp
945                 950                 955                 960

Glu Ile Gly Ala Leu
            965

<210> SEQ ID NO 8
<211> LENGTH: 1038
<212> TYPE: PRT
<213> ORGANISM: Bifidobacterium bifidum

<400> SEQUENCE: 8

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Ser Ala Trp Gln Gln Val Asp Leu
50                  55                  60

```
Pro His Asp Tyr Ser Ile Thr Gln Lys Tyr Ser Gln Ser Asn Glu Ala
 65                  70                  75                  80

Glu Ser Ala Tyr Leu Pro Gly Gly Thr Gly Trp Tyr Arg Lys Ser Phe
                 85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
    435                 440                 445

Met Glu Gly Ile Ser Gly Ser Val Ser Gly Phe Pro Ala Thr Ser Ala
450                 455                 460

Lys Leu Val Ala Trp Thr Lys Ala Ala Asp Ser Thr Arg Pro Met Thr
465                 470                 475                 480
```

-continued

Tyr Gly Asp Asn Lys Ile Lys Ala Asn Trp Asn Glu Ser Asn Thr Met
                485                 490                 495
Gly Asp Asn Leu Thr Ala Asn Gly Gly Val Val Gly Thr Asn Tyr Ser
            500                 505                 510
Asp Gly Ala Asn Tyr Asp Lys Ile Arg Thr Thr His Pro Ser Trp Ala
            515                 520                 525
Ile Tyr Gly Ser Glu Thr Ala Ser Ala Ile Asn Ser Arg Gly Ile Tyr
            530                 535                 540
Asn Arg Thr Thr Gly Ala Gln Ser Ser Asp Lys Gln Leu Thr Ser
545                 550                 555                 560
Tyr Asp Asn Ser Ala Val Gly Trp Gly Ala Val Ala Ser Ser Ala Trp
                565                 570                 575
Tyr Asp Val Val Gln Arg Asp Phe Val Ala Gly Thr Tyr Val Trp Thr
            580                 585                 590
Gly Phe Asp Tyr Leu Gly Glu Pro Thr Pro Trp Asn Gly Thr Gly Ser
            595                 600                 605
Gly Ala Val Gly Ser Trp Pro Ser Pro Lys Asn Ser Tyr Phe Gly Ile
            610                 615                 620
Val Asp Thr Ala Gly Phe Pro Lys Asp Thr Tyr Tyr Phe Tyr Gln Ser
625                 630                 635                 640
Gln Trp Asn Asp Asp Val His Thr Leu His Ile Leu Pro Ala Trp Asn
                645                 650                 655
Glu Asn Val Val Ala Lys Gly Ser Gly Asn Asn Val Pro Val Val
            660                 665                 670
Tyr Thr Asp Ala Ala Lys Val Lys Leu Tyr Phe Thr Pro Lys Gly Ser
            675                 680                 685
Thr Glu Lys Arg Leu Ile Gly Glu Lys Ser Phe Thr Lys Lys Thr Thr
            690                 695                 700
Ala Ala Gly Tyr Thr Tyr Gln Val Tyr Glu Gly Ser Asp Lys Asp Ser
705                 710                 715                 720
Thr Ala His Lys Asn Met Tyr Leu Thr Trp Asn Val Pro Trp Ala Glu
                725                 730                 735
Gly Thr Ile Ser Ala Glu Ala Tyr Asp Glu Asn Asn Arg Leu Ile Pro
            740                 745                 750
Glu Gly Ser Thr Glu Gly Asn Ala Ser Val Thr Thr Gly Lys Ala
            755                 760                 765
Ala Lys Leu Lys Ala Asp Ala Asp Arg Lys Thr Ile Thr Ala Asp Gly
            770                 775                 780
Lys Asp Leu Ser Tyr Ile Glu Val Asp Val Thr Asp Ala Asn Gly His
785                 790                 795                 800
Ile Val Pro Asp Ala Ala Asn Arg Val Thr Phe Asp Val Lys Gly Ala
                805                 810                 815
Gly Lys Leu Val Gly Val Asp Asn Gly Ser Ser Pro Asp His Asp Ser
            820                 825                 830
Tyr Gln Ala Asp Asn Arg Lys Ala Phe Ser Gly Lys Val Leu Ala Ile
            835                 840                 845
Val Gln Ser Thr Lys Glu Ala Gly Glu Ile Thr Val Thr Ala Lys Ala
            850                 855                 860
Asp Gly Leu Gln Ser Ser Thr Val Lys Ile Ala Thr Ala Val Pro
865                 870                 875                 880
Gly Thr Ser Thr Glu Lys Thr Val Arg Ser Phe Tyr Tyr Ser Arg Asn
            885                 890                 895

```
Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
            915                 920                 925

Ala Val Ser Asp Asp Gln Ile Ala Lys Ala Gly Ser Phe Ser Val Ala
930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
            995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

<210> SEQ ID NO 9
<211> LENGTH: 1142
<212> TYPE: PRT
<213> ORGANISM: Bifidobacterium bifidum

<400> SEQUENCE: 9

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
            20                  25                  30

Ser Asp Phe Asp Ala Asn Trp Lys Phe Met Leu Ser Asp Ser Val Gln
        35                  40                  45

Ala Gln Asp Pro Ala Phe Asp Asp Ser Ala Trp Gln Gln Val Asp Leu
    50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220
```

```
Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
            245                 250                 255

Ala Asp Val Thr Ser Thr Ile Thr Ala Ala Ser Pro Lys Leu Trp Ser
                260                 265                 270

Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
        290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640
```

-continued

```
Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
    690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
    770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
    850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
    930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
        995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050
```

```
Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
    1115                1120                1125

Ala Val Arg Phe Pro Asp Ala Gly Lys Thr Lys Ile Gln Ile
    1130                1135                1140

<210> SEQ ID NO 10
<211> LENGTH: 1211
<212> TYPE: PRT
<213> ORGANISM: Bifidobacterium bifidum

<400> SEQUENCE: 10

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Ser Val Gln
        35                  40                  45

Ala Gln Asp Pro Ala Phe Asp Asp Ser Ala Trp Gln Gln Val Asp Leu
50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
            100                 105                 110

Gly Val Tyr Met Asn Ala Thr Val Trp Phe Asn Gly Val Lys Leu Gly
        115                 120                 125

Thr His Pro Tyr Gly Tyr Ser Pro Phe Ser Phe Asp Leu Thr Gly Asn
    130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
    210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
                245                 250                 255

Ala Asp Val Thr Ser Thr Ile Thr Ala Ala Ser Pro Lys Leu Trp Ser
            260                 265                 270
```

```
Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
    290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
        355                 360                 365

Ile Asp Val Cys Asn Glu Lys Gly Val Leu Val Val Glu Glu Val Phe
    370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
                485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
        515                 520                 525

Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
                565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
    610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
            660                 665                 670

Tyr Thr Asp Ala Ala Lys Val Lys Leu Tyr Phe Thr Pro Lys Gly Ser
        675                 680                 685
```

```
Thr Glu Lys Arg Leu Ile Gly Glu Lys Ser Phe Thr Lys Lys Thr
690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
            725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
        755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
            805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
            835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
            885                 890                 895

Tyr Tyr Val Lys Thr Gly Asn Lys Pro Ile Leu Pro Ser Asp Val Glu
            900                 905                 910

Val Arg Tyr Ser Asp Gly Thr Ser Asp Arg Gln Asn Val Thr Trp Asp
            915                 920                 925

Ala Val Ser Asp Asp Gln Ile Ala Lys Ala Gly Ser Phe Ser Val Ala
930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
            965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
        995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050

Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095
```

```
Ala Gly His Asn Thr Ala Glu Ile Thr Phe Glu Tyr Ala Thr Glu
    1100            1105                1110

Gln Gln Leu Gly Gln Ile Val Met Tyr Phe Phe Arg Asp Ser Asn
    1115            1120                1125

Ala Val Arg Phe Pro Asp Ala Gly Lys Thr Lys Ile Gln Ile Ser
    1130            1135                1140

Ala Asp Gly Lys Asn Trp Thr Asp Leu Ala Ala Thr Glu Thr Ile
    1145            1150                1155

Ala Ala Gln Glu Ser Ser Asp Arg Val Lys Pro Tyr Thr Tyr Asp
    1160            1165                1170

Phe Ala Pro Val Gly Ala Thr Phe Val Lys Val Thr Val Thr Asn
    1175            1180                1185

Ala Asp Thr Thr Thr Pro Ser Gly Val Val Cys Ala Gly Leu Thr
    1190            1195                1200

Glu Ile Glu Leu Lys Thr Ala Thr
    1205            1210

<210> SEQ ID NO 11
<211> LENGTH: 1296
<212> TYPE: PRT
<213> ORGANISM: Bifidobacterium bifidum

<400> SEQUENCE: 11

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110

Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
        130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Gly Ile Tyr Arg Asp Val
                165                 170                 175

Thr Leu Thr Val Thr Asp Gly Val His Val Gly Asn Asn Gly Val Ala
                180                 185                 190

Ile Lys Thr Pro Ser Leu Ala Thr Gln Asn Gly Gly Asp Val Thr Met
            195                 200                 205

Asn Leu Thr Thr Lys Val Ala Asn Asp Thr Glu Ala Ala Ala Asn Ile
        210                 215                 220

Thr Leu Lys Gln Thr Val Phe Pro Lys Gly Gly Lys Thr Asp Ala Ala
225                 230                 235                 240
```

```
Ile Gly Thr Val Thr Thr Ala Ser Lys Ser Ile Ala Ala Gly Ala Ser
            245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
            275                 280                 285

Gly Lys Val Leu Asp Thr Tyr Asp Thr Glu Tyr Gly Phe Arg Trp Thr
            290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
                325                 330                 335

Ala Asn Arg Arg Ala Ile Glu Arg Gln Val Glu Ile Leu Gln Lys Met
            340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Glu Glu Val Phe
370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
            435                 440                 445

Met Glu Gly Ile Ser Gly Ser Val Ser Gly Phe Pro Ala Thr Ser Ala
450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
            485                 490                 495

Gly Asp Asn Leu Thr Ala Asn Gly Gly Val Val Gly Thr Asn Tyr Ser
            500                 505                 510

Asp Gly Ala Asn Tyr Asp Lys Ile Arg Thr Thr His Pro Ser Trp Ala
            515                 520                 525

Ile Tyr Gly Ser Glu Thr Ala Ser Ala Ile Asn Ser Arg Gly Ile Tyr
            530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Ala Val Ala Ser Ser Ala Trp
            565                 570                 575

Tyr Asp Val Val Gln Arg Asp Phe Val Ala Gly Thr Tyr Val Trp Thr
            580                 585                 590

Gly Phe Asp Tyr Leu Gly Glu Pro Thr Pro Trp Asn Gly Thr Gly Ser
            595                 600                 605

Gly Ala Val Gly Ser Trp Pro Ser Pro Lys Asn Ser Tyr Phe Gly Ile
            610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
            645                 650                 655
```

-continued

Glu Asn Val Val Ala Lys Gly Ser Gly Asn Val Pro Val Val
            660                 665                 670

Tyr Thr Asp Ala Ala Lys Val Lys Leu Tyr Phe Thr Pro Lys Gly Ser
            675                 680                 685

Thr Glu Lys Arg Leu Ile Gly Glu Lys Ser Phe Thr Lys Lys Thr Thr
690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
            725                 730                 735

Gly Thr Ile Ser Ala Glu Ala Tyr Asp Glu Asn Asn Arg Leu Ile Pro
            740                 745                 750

Glu Gly Ser Thr Glu Gly Asn Ala Ser Val Thr Thr Gly Lys Ala
            755                 760                 765

Ala Lys Leu Lys Ala Asp Ala Asp Arg Lys Thr Ile Thr Ala Asp Gly
            770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                    805                 810                 815

Gly Lys Leu Val Gly Val Asp Asn Gly Ser Ser Pro Asp His Asp Ser
            820                 825                 830

Tyr Gln Ala Asp Asn Arg Lys Ala Phe Ser Gly Lys Val Leu Ala Ile
            835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Thr Ala Val Pro
865                 870                 875                 880

Gly Thr Ser Thr Glu Lys Thr Val Arg Ser Phe Tyr Tyr Ser Arg Asn
                    885                 890                 895

Tyr Tyr Val Lys Thr Gly Asn Lys Pro Ile Leu Pro Ser Asp Val Glu
                    900                 905                 910

Val Arg Tyr Ser Asp Gly Thr Ser Asp Arg Gln Asn Val Thr Trp Asp
            915                 920                 925

Ala Val Ser Asp Asp Gln Ile Ala Lys Ala Gly Ser Phe Ser Val Ala
930                 935                 940

Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                    965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
            995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050

Arg Leu Thr Gln Asn Ile Pro Ala Asp Lys Gln Ser Asp Thr Leu
    1055                1060                1065

```
Asp Ala Ile Lys Asp Gly Ser Thr Thr Val Asp Ala Asn Thr Gly
    1070            1075                1080

Gly Gly Ala Asn Pro Ser Ala Trp Thr Asn Trp Ala Tyr Ser Lys
    1085            1090                1095

Ala Gly His Asn Thr Ala Glu Ile Thr Phe Glu Tyr Ala Thr Glu
    1100            1105                1110

Gln Gln Leu Gly Gln Ile Val Met Tyr Phe Phe Arg Asp Ser Asn
    1115            1120                1125

Ala Val Arg Phe Pro Asp Ala Gly Lys Thr Lys Ile Gln Ile Ser
    1130            1135                1140

Ala Asp Gly Lys Asn Trp Thr Asp Leu Ala Ala Thr Glu Thr Ile
    1145            1150                1155

Ala Ala Gln Glu Ser Ser Asp Arg Val Lys Pro Tyr Thr Tyr Asp
    1160            1165                1170

Phe Ala Pro Val Gly Ala Thr Phe Val Lys Val Thr Val Thr Asn
    1175            1180                1185

Ala Asp Thr Thr Thr Pro Ser Gly Val Val Cys Ala Gly Leu Thr
    1190            1195                1200

Glu Ile Glu Leu Lys Thr Ala Thr Ser Lys Phe Val Thr Asn Thr
    1205            1210                1215

Ser Ala Ala Leu Ser Ser Leu Thr Val Asn Gly Thr Lys Val Ser
    1220            1225                1230

Asp Ser Val Leu Ala Ala Gly Ser Tyr Asn Thr Pro Ala Ile Ile
    1235            1240                1245

Ala Asp Val Lys Ala Glu Gly Glu Gly Asn Ala Ser Val Thr Val
    1250            1255                1260

Leu Pro Ala His Asp Asn Val Ile Arg Val Ile Thr Glu Ser Glu
    1265            1270                1275

Asp His Val Thr Arg Lys Thr Phe Thr Ile Asn Leu Gly Thr Glu
    1280            1285                1290

Gln Glu Phe
    1295

<210> SEQ ID NO 12
<211> LENGTH: 1720
<212> TYPE: PRT
<213> ORGANISM: Bifidobacterium bifidum

<400> SEQUENCE: 12

Val Glu Asp Ala Thr Arg Ser Asp Ser Thr Thr Gln Met Ser Ser Thr
1               5                   10                  15

Pro Glu Val Val Tyr Ser Ser Ala Val Asp Ser Lys Gln Asn Arg Thr
                20                  25                  30

Ser Asp Phe Asp Ala Asn Trp Lys Phe Met Leu Ser Asp Ser Val Gln
            35                  40                  45

Ala Gln Asp Pro Ala Phe Asp Asp Ser Ala Trp Gln Gln Val Asp Leu
        50                  55                  60

Pro His Asp Tyr Ser Ile Thr Gln Lys Tyr Ser Gln Ser Asn Glu Ala
65                  70                  75                  80

Glu Ser Ala Tyr Leu Pro Gly Gly Thr Gly Trp Tyr Arg Lys Ser Phe
                85                  90                  95

Thr Ile Asp Arg Asp Leu Ala Gly Lys Arg Ile Ala Ile Asn Phe Asp
                100                 105                 110
```

```
Gly Val Tyr Met Asn Ala Thr Val Trp Phe Asn Gly Val Lys Leu Gly
            115                 120                 125

Thr His Pro Tyr Gly Tyr Ser Pro Phe Ser Phe Asp Leu Thr Gly Asn
        130                 135                 140

Ala Lys Phe Gly Gly Glu Asn Thr Ile Val Val Lys Val Glu Asn Arg
145                 150                 155                 160

Leu Pro Ser Ser Arg Trp Tyr Ser Gly Ser Ile Tyr Arg Asp Val
                165                 170                 175

Thr Leu Thr Val Thr Asp Gly Val His Val Gly Asn Asn Gly Val Ala
            180                 185                 190

Ile Lys Thr Pro Ser Leu Ala Thr Gln Asn Gly Gly Asp Val Thr Met
        195                 200                 205

Asn Leu Thr Thr Lys Val Ala Asn Asp Thr Glu Ala Ala Ala Asn Ile
            210                 215                 220

Thr Leu Lys Gln Thr Val Phe Pro Lys Gly Gly Lys Thr Asp Ala Ala
225                 230                 235                 240

Ile Gly Thr Val Thr Thr Ala Ser Lys Ser Ile Ala Ala Gly Ala Ser
            245                 250                 255

Ala Asp Val Thr Ser Thr Ile Thr Ala Ala Ser Pro Lys Leu Trp Ser
            260                 265                 270

Ile Lys Asn Pro Asn Leu Tyr Thr Val Arg Thr Glu Val Leu Asn Gly
        275                 280                 285

Gly Lys Val Leu Asp Thr Tyr Asp Thr Glu Tyr Gly Phe Arg Trp Thr
            290                 295                 300

Gly Phe Asp Ala Thr Ser Gly Phe Ser Leu Asn Gly Glu Lys Val Lys
305                 310                 315                 320

Leu Lys Gly Val Ser Met His His Asp Gln Gly Ser Leu Gly Ala Val
            325                 330                 335

Ala Asn Arg Arg Ala Ile Glu Arg Gln Val Glu Ile Leu Gln Lys Met
                340                 345                 350

Gly Val Asn Ser Ile Arg Thr Thr His Asn Pro Ala Ala Lys Ala Leu
            355                 360                 365

Ile Asp Val Cys Asn Glu Lys Gly Val Leu Val Glu Glu Val Phe
        370                 375                 380

Asp Met Trp Asn Arg Ser Lys Asn Gly Asn Thr Glu Asp Tyr Gly Lys
385                 390                 395                 400

Trp Phe Gly Gln Ala Ile Ala Gly Asp Asn Ala Val Leu Gly Gly Asp
                405                 410                 415

Lys Asp Glu Thr Trp Ala Lys Phe Asp Leu Thr Ser Thr Ile Asn Arg
            420                 425                 430

Asp Arg Asn Ala Pro Ser Val Ile Met Trp Ser Leu Gly Asn Glu Met
        435                 440                 445

Met Glu Gly Ile Ser Gly Ser Val Ser Gly Phe Pro Ala Thr Ser Ala
    450                 455                 460

Lys Leu Val Ala Trp Thr Lys Ala Ala Asp Ser Thr Arg Pro Met Thr
465                 470                 475                 480

Tyr Gly Asp Asn Lys Ile Lys Ala Asn Trp Asn Glu Ser Asn Thr Met
            485                 490                 495

Gly Asp Asn Leu Thr Ala Asn Gly Val Val Gly Thr Asn Tyr Ser
        500                 505                 510

Asp Gly Ala Asn Tyr Asp Lys Ile Arg Thr Thr His Pro Ser Trp Ala
            515                 520                 525
```

```
Ile Tyr Gly Ser Glu Thr Ala Ser Ala Ile Asn Ser Arg Gly Ile Tyr
    530                 535                 540

Asn Arg Thr Thr Gly Gly Ala Gln Ser Ser Asp Lys Gln Leu Thr Ser
545                 550                 555                 560

Tyr Asp Asn Ser Ala Val Gly Trp Gly Val Ala Ser Ser Ala Trp
                565                 570                 575

Tyr Asp Val Val Gln Arg Asp Phe Val Ala Gly Thr Tyr Val Trp Thr
                580                 585                 590

Gly Phe Asp Tyr Leu Gly Glu Pro Thr Pro Trp Asn Gly Thr Gly Ser
        595                 600                 605

Gly Ala Val Gly Ser Trp Pro Ser Pro Lys Asn Ser Tyr Phe Gly Ile
        610                 615                 620

Val Asp Thr Ala Gly Phe Pro Lys Asp Thr Tyr Tyr Phe Tyr Gln Ser
625                 630                 635                 640

Gln Trp Asn Asp Asp Val His Thr Leu His Ile Leu Pro Ala Trp Asn
                645                 650                 655

Glu Asn Val Val Ala Lys Gly Ser Gly Asn Asn Val Pro Val Val Val
                660                 665                 670

Tyr Thr Asp Ala Ala Lys Val Lys Leu Tyr Phe Thr Pro Lys Gly Ser
        675                 680                 685

Thr Glu Lys Arg Leu Ile Gly Glu Lys Ser Phe Thr Lys Lys Thr Thr
690                 695                 700

Ala Ala Gly Tyr Thr Tyr Gln Val Tyr Glu Gly Ser Asp Lys Asp Ser
705                 710                 715                 720

Thr Ala His Lys Asn Met Tyr Leu Thr Trp Asn Val Pro Trp Ala Glu
                725                 730                 735

Gly Thr Ile Ser Ala Glu Ala Tyr Asp Glu Asn Asn Arg Leu Ile Pro
                740                 745                 750

Glu Gly Ser Thr Glu Gly Asn Ala Ser Val Thr Thr Thr Gly Lys Ala
        755                 760                 765

Ala Lys Leu Lys Ala Asp Ala Asp Arg Lys Thr Ile Thr Ala Asp Gly
770                 775                 780

Lys Asp Leu Ser Tyr Ile Glu Val Asp Val Thr Asp Ala Asn Gly His
785                 790                 795                 800

Ile Val Pro Asp Ala Ala Asn Arg Val Thr Phe Asp Val Lys Gly Ala
                805                 810                 815

Gly Lys Leu Val Gly Val Asp Asn Gly Ser Ser Pro Asp His Asp Ser
                820                 825                 830

Tyr Gln Ala Asp Asn Arg Lys Ala Phe Ser Gly Lys Val Leu Ala Ile
        835                 840                 845

Val Gln Ser Thr Lys Glu Ala Gly Glu Ile Thr Val Thr Ala Lys Ala
850                 855                 860

Asp Gly Leu Gln Ser Ser Thr Val Lys Ile Ala Thr Ala Val Pro
865                 870                 875                 880

Gly Thr Ser Thr Glu Lys Thr Val Arg Ser Phe Tyr Ser Arg Asn
                885                 890                 895

Tyr Tyr Val Lys Thr Gly Asn Lys Pro Ile Leu Pro Ser Asp Val Glu
                900                 905                 910

Val Arg Tyr Ser Asp Gly Thr Ser Asp Arg Gln Asn Val Thr Trp Asp
        915                 920                 925

Ala Val Ser Asp Asp Gln Ile Ala Lys Ala Gly Ser Phe Ser Val Ala
930                 935                 940
```

```
Gly Thr Val Ala Gly Gln Lys Ile Ser Val Arg Val Thr Met Ile Asp
945                 950                 955                 960

Glu Ile Gly Ala Leu Leu Asn Tyr Ser Ala Ser Thr Pro Val Gly Thr
                965                 970                 975

Pro Ala Val Leu Pro Gly Ser Arg Pro Ala Val Leu Pro Asp Gly Thr
            980                 985                 990

Val Thr Ser Ala Asn Phe Ala Val His Trp Thr Lys Pro Ala Asp Thr
        995                 1000                1005

Val Tyr Asn Thr Ala Gly Thr Val Lys Val Pro Gly Thr Ala Thr
    1010                1015                1020

Val Phe Gly Lys Glu Phe Lys Val Thr Ala Thr Ile Arg Val Gln
    1025                1030                1035

Arg Ser Gln Val Thr Ile Gly Ser Ser Val Ser Gly Asn Ala Leu
    1040                1045                1050

Arg Leu Thr Gln Asn Ile Pro Ala Asp Lys Gln Ser Asp Thr Leu
    1055                1060                1065

Asp Ala Ile Lys Asp Gly Ser Thr Thr Val Asp Ala Asn Thr Gly
    1070                1075                1080

Gly Gly Ala Asn Pro Ser Ala Trp Thr Asn Trp Ala Tyr Ser Lys
    1085                1090                1095

Ala Gly His Asn Thr Ala Glu Ile Thr Phe Glu Tyr Ala Thr Glu
    1100                1105                1110

Gln Gln Leu Gly Gln Ile Val Met Tyr Phe Phe Arg Asp Ser Asn
    1115                1120                1125

Ala Val Arg Phe Pro Asp Ala Gly Lys Thr Lys Ile Gln Ile Ser
    1130                1135                1140

Ala Asp Gly Lys Asn Trp Thr Asp Leu Ala Ala Thr Glu Thr Ile
    1145                1150                1155

Ala Ala Gln Glu Ser Ser Asp Arg Val Lys Pro Tyr Thr Tyr Asp
    1160                1165                1170

Phe Ala Pro Val Gly Ala Thr Phe Val Lys Val Thr Val Thr Asn
    1175                1180                1185

Ala Asp Thr Thr Thr Pro Ser Gly Val Val Cys Ala Gly Leu Thr
    1190                1195                1200

Glu Ile Glu Leu Lys Thr Ala Thr Ser Lys Phe Val Thr Asn Thr
    1205                1210                1215

Ser Ala Ala Leu Ser Ser Leu Thr Val Asn Gly Thr Lys Val Ser
    1220                1225                1230

Asp Ser Val Leu Ala Ala Gly Ser Tyr Asn Thr Pro Ala Ile Ile
    1235                1240                1245

Ala Asp Val Lys Ala Glu Gly Glu Gly Asn Ala Ser Val Thr Val
    1250                1255                1260

Leu Pro Ala His Asp Asn Val Ile Arg Val Ile Thr Glu Ser Glu
    1265                1270                1275

Asp His Val Thr Arg Lys Thr Phe Thr Ile Asn Leu Gly Thr Glu
    1280                1285                1290

Gln Glu Phe Pro Ala Asp Ser Asp Glu Arg Asp Tyr Pro Ala Ala
    1295                1300                1305

Asp Met Thr Val Thr Val Gly Ser Glu Gln Thr Ser Gly Thr Ala
    1310                1315                1320

Thr Glu Gly Pro Lys Lys Phe Ala Val Asp Gly Asn Thr Ser Thr
    1325                1330                1335
```

-continued

Tyr Trp His Ser Asn Trp Thr Pro Thr Thr Val Asn Asp Leu Trp
1340                1345                1350

Ile Ala Phe Glu Leu Gln Lys Pro Thr Lys Leu Asp Ala Leu Arg
1355                1360                1365

Tyr Leu Pro Arg Pro Ala Gly Ser Lys Asn Gly Ser Val Thr Glu
1370                1375                1380

Tyr Lys Val Gln Val Ser Asp Asp Gly Thr Asn Trp Thr Asp Ala
1385                1390                1395

Gly Ser Gly Thr Trp Thr Thr Asp Tyr Gly Trp Lys Leu Ala Glu
1400                1405                1410

Phe Asn Gln Pro Val Thr Thr Lys His Val Arg Leu Lys Ala Val
1415                1420                1425

His Thr Tyr Ala Asp Ser Gly Asn Asp Lys Phe Met Ser Ala Ser
1430                1435                1440

Glu Ile Arg Leu Arg Lys Ala Val Asp Thr Thr Asp Ile Ser Gly
1445                1450                1455

Ala Thr Val Thr Val Pro Ala Lys Leu Thr Val Asp Arg Val Asp
1460                1465                1470

Ala Asp His Pro Ala Thr Phe Ala Thr Lys Asp Val Thr Val Thr
1475                1480                1485

Leu Gly Asp Ala Thr Leu Arg Tyr Gly Val Asp Tyr Leu Leu Asp
1490                1495                1500

Tyr Ala Gly Asn Thr Ala Val Gly Lys Ala Thr Val Thr Val Arg
1505                1510                1515

Gly Ile Asp Lys Tyr Ser Gly Thr Val Ala Lys Thr Phe Thr Ile
1520                1525                1530

Glu Leu Lys Asn Ala Pro Ala Pro Glu Pro Thr Leu Thr Ser Val
1535                1540                1545

Ser Val Lys Thr Lys Pro Ser Lys Leu Thr Tyr Val Val Gly Asp
1550                1555                1560

Ala Phe Asp Pro Ala Gly Leu Val Leu Gln His Asp Arg Gln Ala
1565                1570                1575

Asp Arg Pro Pro Gln Pro Leu Val Gly Glu Gln Ala Asp Glu Arg
1580                1585                1590

Gly Leu Thr Cys Gly Thr Arg Cys Asp Arg Val Glu Gln Leu Arg
1595                1600                1605

Lys His Glu Asn Arg Glu Ala His Arg Thr Gly Leu Asp His Leu
1610                1615                1620

Glu Phe Val Gly Ala Ala Asp Gly Ala Val Gly Glu Gln Ala Thr
1625                1630                1635

Phe Lys Val His Val His Ala Asp Gln Gly Asp Gly Arg His Asp
1640                1645                1650

Asp Ala Asp Glu Arg Asp Ile Asp Pro His Val Pro Val Asp His
1655                1660                1665

Ala Val Gly Glu Leu Ala Arg Ala Ala Cys His His Val Ile Gly
1670                1675                1680

Leu Arg Val Asp Thr His Arg Leu Lys Ala Ser Gly Phe Gln Ile
1685                1690                1695

Pro Ala Asp Asp Met Ala Glu Ile Asp Arg Ile Thr Gly Phe His
1700                1705                1710

Arg Phe Glu Arg His Val Gly
1715                1720

```
<210> SEQ ID NO 13
<211> LENGTH: 1396
<212> TYPE: PRT
<213> ORGANISM: Bacillus circulans

<400> SEQUENCE: 13

Met Arg Arg Ile Asn Phe Asn Asp Asn Trp Arg Phe Gln Arg Glu Ile
1               5                   10                  15

Ser Thr Ser Leu Arg Glu Ala Gln Lys Pro Ser Phe Asn Asp His Ser
            20                  25                  30

Trp Arg Gln Leu Ser Leu Pro His Asp Trp Ser Ile Glu Leu Asp Phe
        35                  40                  45

Asn Lys Asp Ser Leu Ala Thr His Glu Gly Gly Tyr Leu Asp Gly Gly
    50                  55                  60

Val Gly Trp Tyr Arg Lys Thr Phe Thr Val Pro Ser Ala Met Glu Gly
65                  70                  75                  80

Lys Arg Ile Ser Leu Asp Phe Asp Gly Val Tyr Met Asn Ser Thr Thr
                85                  90                  95

Tyr Leu Asn Gly Glu Glu Leu Gly Thr Tyr Pro Phe Gly Tyr Asn Ala
            100                 105                 110

Phe Ser Tyr Asp Ile Thr Asp Lys Leu Phe Met Asp Gly Arg Glu Asn
        115                 120                 125

Val Leu Ala Val Lys Val Asp Asn Thr Gln Pro Ser Ser Arg Trp Tyr
130                 135                 140

Ser Gly Ser Gly Ile Tyr Arg Asn Val Tyr Leu Thr Val Thr Asn Pro
145                 150                 155                 160

Val His Val Ala Arg Tyr Gly Thr Phe Val Thr Thr Pro Asp Leu Glu
                165                 170                 175

Ser Ala Tyr Ala Ala Arg Lys Ala Glu Val Asn Ile Lys Thr Lys Ile
            180                 185                 190

Asn Asn Asp Ser Asp Ala Ala Val Gln Val Lys Val Lys Ser Thr Ile
        195                 200                 205

Tyr Asp Thr Asp Gly Lys Glu Val Ala Ser Val Val Ser Gln Glu Lys
    210                 215                 220

Thr Ala Ala Ala Gly Thr Thr Ala His Phe Glu Asp Asn Thr Val Ile
225                 230                 235                 240

Glu Asn Pro Glu Leu Trp Ser Leu Asp Asn Pro Tyr Arg Tyr Lys Leu
                245                 250                 255

Val Thr Asp Val Leu Ile Gly Gly Glu Thr Val Asp Thr Tyr Glu Thr
            260                 265                 270

Arg Phe Gly Ala Arg Phe Phe Lys Phe Asp Ala Asn Glu Gly Phe Ser
        275                 280                 285

Leu Asn Gly Lys Pro Met Lys Leu Tyr Gly Val Ser Met His His Asp
    290                 295                 300

Leu Gly Ala Leu Gly Ala Ala Thr Asn Ala Arg Ala Val Glu Arg Gln
305                 310                 315                 320

Leu Gln Ile Met Lys Asp Met Gly Val Asn Ala Ile Arg Gly Thr His
                325                 330                 335

Asn Pro Val Ser Pro Glu Phe Leu Glu Ala Val Asn Asn Leu Gly Leu
            340                 345                 350

Leu Leu Ile Glu Glu Ala Phe Asp Cys Trp Ser Gln Ser Lys Lys Thr
        355                 360                 365

Tyr Asp Tyr Gly Arg Phe Phe Thr Arg Trp Ala Glu His Asp Val Lys
    370                 375                 380
```

```
Glu Met Val Asp Arg Gly Lys Asn Glu Pro Ser Ile Ile Met Trp Ser
385                 390                 395                 400

Ile Gly Asn Glu Ile Tyr Asp Thr Thr Ser Pro Ser Gly Val Glu Thr
            405                 410                 415

Ala Arg Asn Leu Val Arg Trp Ile Lys Glu Ile Asp Thr Thr Arg Pro
            420                 425                 430

Thr Thr Ile Gly Glu Asp Lys Thr Arg Gly Asp Lys Val Asn Val Thr
            435                 440                 445

Pro Ile Asp Pro Asn Ile Leu Glu Ile Phe His Thr Val Asp Val Val
450                 455                 460

Gly Leu Asn Tyr Ser Glu Asn Asn Tyr Val Gly Tyr His Glu Gln His
465                 470                 475                 480

Pro Asn Trp Lys Leu Tyr Gly Ser Glu Thr Ser Ser Ala Thr Arg Ser
            485                 490                 495

Arg Gly Val Tyr Thr His Pro Tyr Glu Tyr Asn Leu Gly Thr Lys Tyr
            500                 505                 510

Asp Asp Leu Gln Gln Ser Ser Tyr Asp Asn Asp Tyr Val Pro Trp Gly
            515                 520                 525

Arg Thr Ala Glu Asp Ala Trp Lys Ser Asp Arg Asp Leu Lys His Phe
530                 535                 540

Ala Gly Gln Phe Ile Trp Thr Gly Phe Asp Tyr Ile Gly Glu Pro Thr
545                 550                 555                 560

Pro Tyr Tyr Asp Ser Tyr Pro Ala Lys Ser Ser Tyr Phe Gly Ala Val
            565                 570                 575

Asp Thr Ala Gly Phe Pro Lys Asp Ile Phe Tyr Tyr Gln Ser Gln
            580                 585                 590

Trp Lys Lys Glu Pro Met Val His Leu Pro His Trp Asn Trp Thr
            595                 600                 605

Glu Gly Glu Pro Val Arg Val Leu Ala Tyr Thr Asn Ala His Gln Val
610                 615                 620

Glu Leu Phe Leu Asn Gly Lys Ser Leu Gly Val Arg Gly Tyr Glu Asn
625                 630                 635                 640

Lys Lys Thr Ser Trp Gly Ala Pro Tyr Lys Glu Thr Lys Asp Gly Lys
            645                 650                 655

Thr Tyr Leu Glu Trp Ala Val Pro Phe Lys Ala Gly Thr Leu Glu Ala
            660                 665                 670

Val Ala Met Asp Glu Asn Gly Lys Glu Ile Ala Arg Asp Gln Val Thr
            675                 680                 685

Thr Ala Gly Ala Pro Ala Ala Val Lys Leu Thr Ala Asp Arg Lys Val
            690                 695                 700

Ile Lys Ala Asp Gly Thr Asp Leu Ser Phe Ile Thr Ala Glu Ile Val
705                 710                 715                 720

Asp Ser Lys Gly Asn Val Val Pro Asn Ala Asp His Leu Ile Gln Phe
            725                 730                 735

His Leu Ser Gly His Gly Glu Leu Ala Gly Val Asp Asn Gly Asp Ala
            740                 745                 750

Ala Ser Val Glu Arg Tyr Lys Asp Asn Lys Arg Lys Ala Phe Ser Gly
            755                 760                 765

Lys Ala Leu Ala Ile Val Gln Ser Asn Lys Leu Asp Gly Asn Ile Thr
            770                 775                 780

Leu His Ala Ser Ala Glu Gly Leu Ser Ser Gly Asn Val Thr Ile Phe
785                 790                 795                 800
```

```
Thr Thr Ala Ser Ala Asp Gln Asn Ser Ile Thr Ile Ala Gly Ile Asp
            805                 810                 815

Glu Val Asn Val Leu Val Asp Phe Asn Val Val Pro Glu Leu Pro Ser
            820                 825                 830

Gln Ile Lys Val Tyr Tyr Ser Asp Ser Thr Val Glu Met Lys Pro Val
            835                 840                 845

Thr Trp Asp Ala Val Asp Pro Asn Leu Leu Asn Thr Ala Gly Lys Ile
            850                 855                 860

Ile Val Glu Gly Thr Val Gly Thr Asp Lys Ala Lys Ala Leu
865                 870                 875                 880

Leu Ile Val Lys Gly Asn Gly Gln Glu Asn Ser Glu Tyr Arg Ile Asp
            885                 890                 895

Leu Phe Ser Pro Asp Pro Lys Leu Ile Ser Thr Glu Leu Thr Val Glu
            900                 905                 910

Lys Thr Asn Ile Met Glu Asp Asp Phe Ile Asp Ile Lys Val Ile Gly
            915                 920                 925

Gln Leu Glu Asn Lys Glu Val Val Asp Leu Ser Asn Phe Met Pro Ile
            930                 935                 940

Tyr Glu Phe Asp Cys Asp Ile Ile Lys Ile Glu Gly Asn Lys Leu Tyr
945                 950                 955                 960

Ala Leu Glu Glu Gly Leu Val Lys Val Thr Ala Ala Val Thr Tyr Lys
            965                 970                 975

Gly Arg Thr Val Thr Ser Pro Glu Met Met Leu Lys Ile Thr Lys Asn
            980                 985                 990

Pro Val Pro Lys Thr Ile Thr His Ile Asp Ser Ile Thr Val Val Ala
            995                1000                1005

Gly Lys Gly Glu Ala Pro Val Leu Pro Ala Thr Ala Val Ala His
            1010               1015                1020

Phe Asp Arg Gly Met Pro Arg Asp Val Lys Val Lys Trp Glu Ile
     1025               1030                1035

Val Asn Pro Ala Leu Tyr Gln Asn Leu Gly Glu Phe Thr Val Ser
     1040               1045                1050

Gly Asp Val Glu Gly Thr Glu Ile Lys Ala Gln Ala Lys Val Met
     1055               1060                1065

Val Arg Ser Ala Leu Ala Ile Glu Thr Ile Ser Met Ala Val Leu
     1070               1075                1080

Pro Asn Gln Lys Pro Glu Leu Pro Gln Lys Val Thr Val Tyr Tyr
     1085               1090                1095

Ser Asp Gly Thr Glu Glu Gln Ala Asp Val Asp Trp Asp Ala Met
     1100               1105                1110

Pro Ser Ala Glu Leu Lys Ser Glu Gly Val Val Lys Val Lys Gly
     1115               1120                1125

Ser Val Lys Gly Val Asp Leu Lys Ala Thr Ala Gln Ile Arg Val
     1130               1135                1140

Thr Ser Glu Val Gly Gly Val Gln Asn Ile Ser Arg Ala Lys Asn
     1145               1150                1155

Gly Tyr Glu Tyr Pro Lys Ala Glu Ala Ser Phe Thr Asn Thr Gly
     1160               1165                1170

Pro Gly Ser Asn Asp Arg Ile Glu Ala Ile Asn Asp Asp Val Ile
     1175               1180                1185

Ser Tyr Asp Ala Glu Pro His Asn Arg Trp Thr Asn Trp Gln Pro
     1190               1195                1200
```

```
Thr Pro Arg Pro Gly Asp Trp Val Ser Ile Thr Phe Gly Asp Ser
    1205                1210                1215

Lys Pro Arg Lys Tyr Asp Ile Asp Ser Met Glu Ile His Trp Tyr
    1220                1225                1230

Glu Asp Leu Gly Thr Ser Ser Pro Ala Tyr Phe Arg Ile Gln Tyr
    1235                1240                1245

Lys Ser Gly Asp Glu Trp Lys Asp Val Ser Gly Leu Lys Thr Asn
    1250                1255                1260

Pro Ser Asn Thr Val Leu Arg Gln Ala Asn Val Tyr Thr Phe Asp
    1265                1270                1275

Lys Val Arg Thr Ser Ala Ile Arg Val Asp Met Thr Ala Lys Thr
    1280                1285                1290

Gly Lys Ser Leu Ala Ile Thr Glu Ile Lys Val Phe Ser Lys Trp
    1295                1300                1305

Ala Lys Ala His Thr His Pro Met Val Thr Asp Ile Lys Leu Gly
    1310                1315                1320

Asp Leu Ser Ile Leu Asp Asp Phe Ser Lys Gly Asp Asn Asn
    1325                1330                1335

Glu Leu Thr Phe Gln Val Lys Asp Pro Arg Asp Ile Pro Glu Ile
    1340                1345                1350

Lys Val Lys Ala Glu Asp Asn Thr Ser Ile Thr Ile Ile Pro Thr
    1355                1360                1365

Phe Thr Ala Pro Ser Thr Ala Lys Ile Ile Ala Lys Ser Glu Asp
    1370                1375                1380

Gly Met Lys Val Glu Ile Tyr Asn Ile Arg Phe Thr Glu
    1385                1390                1395

<210> SEQ ID NO 14
<211> LENGTH: 1737
<212> TYPE: PRT
<213> ORGANISM: Bacillus species

<400> SEQUENCE: 14

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
                20                  25                  30

Ser Ala Ala Gly Asn Ser Val Ser Tyr Asp Gly Glu Arg Arg Val Asn
            35                  40                  45

Phe Asn Glu Asn Trp Arg Phe Gln Arg Glu Thr Asn Gly Ser Ile Ala
        50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
                100                 105                 110

Lys Thr Phe Thr Ile Pro Glu Ser Met Lys Gly Lys Arg Ile Ser Leu
        115                 120                 125

Asp Phe Asp Gly Val Tyr Met Asn Ser Thr Thr Tyr Leu Asn Gly Glu
    130                 135                 140

Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175
```

```
Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
        195                 200                 205

Tyr Gly Thr Phe Val Thr Thr Pro Asn Leu Glu Lys Ser Ile Lys Glu
    210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Ala Gly
            260                 265                 270

Thr Val Thr Pro Phe Glu Gln Asn Thr Val Ile Lys Gln Pro Lys Leu
        275                 280                 285

Trp Ser Ile Asp Lys Pro Tyr Arg Tyr Asn Leu Val Thr Glu Val Ile
    290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350

Ala Ala Thr Asn Ala Arg Gly Val Glu Arg Gln Met Gln Ile Met Lys
        355                 360                 365

Asp Met Gly Val Asn Ala Ile Arg Val Thr His Asn Pro Ala Ser Pro
    370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
            420                 425                 430

Gly Lys Asn Glu Pro Ala Ile Ile Met Trp Ser Ile Gly Asn Glu Ile
        435                 440                 445

Tyr Asp Thr Thr Asn Ala Ala Gly Val Glu Thr Ala Arg Asn Leu Val
    450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
            500                 505                 510

Glu Asn Asn Tyr Asp Gly Tyr His Lys Gln Asn Pro Ser Trp Lys Leu
        515                 520                 525

Tyr Gly Ser Glu Thr Ser Ser Ala Thr Arg Ser Arg Gly Val Tyr Thr
    530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                565                 570                 575

Ala Trp Lys Tyr Asp Arg Asp Leu Lys His Ile Ala Gly Gln Phe Ile
        580                 585                 590
```

-continued

```
Trp Thr Gly Phe Asp Tyr Ile Gly Glu Pro Thr Pro Tyr Asn Ser
            595                 600                 605
Tyr Pro Ala Lys Ser Ser Tyr Phe Gly Ala Val Asp Thr Ala Gly Phe
610                 615                 620
Pro Lys Asp Ile Phe Tyr Tyr Tyr Gln Ser Gln Trp Lys Lys Glu Pro
625                 630                 635                 640
Met Val His Leu Leu Pro His Trp Asn Trp Lys Glu Gly Glu Lys Val
                    645                 650                 655
Arg Val Leu Ala Tyr Thr Asn Ala Ser Lys Val Glu Leu Val Leu Asn
                660                 665                 670
Gly Glu Ser Leu Gly Glu Lys Asn Tyr Asp Asn Lys Gln Thr Ser Trp
            675                 680                 685
Gly Ala Pro Tyr Lys Glu Thr Lys Asp Gly Lys Thr Tyr Leu Glu Trp
690                 695                 700
Ala Val Pro Phe Lys Pro Gly Lys Leu Glu Ala Val Ala Lys Asp Glu
705                 710                 715                 720
Asn Gly Lys Val Ile Ala Arg Asp Gln Val Val Thr Ala Gly Glu Pro
                    725                 730                 735
Ala Ser Val Arg Leu Thr Ala Asp Arg Lys Val Lys Ala Asp Gly
                740                 745                 750
Thr Asp Leu Ser Phe Ile Thr Ala Asp Ile Val Asp Ser Lys Gly Ile
            755                 760                 765
Val Val Pro Asp Ala Asp His Leu Ile Thr Phe Asn Val Thr Gly Gln
770                 775                 780
Gly Glu Leu Ala Gly Val Asp Asn Gly Asn Ala Ser Ser Val Glu Arg
785                 790                 795                 800
Tyr Lys Asp Asn Lys Arg Lys Ala Phe Ser Gly Lys Ala Leu Ala Ile
                    805                 810                 815
Val Gln Ser Ser Lys Leu Ser Gly Lys Ile Thr Val His Ala Ser Val
                820                 825                 830
Ala Gly Leu Ser Ser Asp Ser Thr Ser Val Phe Thr Val Thr Pro Ala
            835                 840                 845
Asp His Asp Lys Lys Ile Val Ala Gly Ile Asp Asp Val Asn Leu Thr
850                 855                 860
Val Asp Val Asn Glu Ala Pro Lys Leu Pro Ser Glu Ile Lys Val Tyr
865                 870                 875                 880
Tyr Ser Asp Glu Ser Ala Ala Lys Asn Val Thr Trp Asp Glu Val
                    885                 890                 895
Asp Pro Lys Gln Tyr Ser Thr Val Gly Glu Phe Thr Val Glu Gly Ser
                900                 905                 910
Val Glu Gly Thr Ser Leu Lys Ala Lys Ala Phe Val Ile Val Lys Gly
            915                 920                 925
Ile Val Ala Val Lys Pro Tyr Ser Thr Ala Thr Lys Val Gly Val Gln
930                 935                 940
Pro Val Leu Pro Glu Lys Ala Thr Leu Leu Tyr Ser Asp Gly Thr Thr
945                 950                 955                 960
Lys Gly Ala Thr Val Thr Trp Asp Glu Ile Pro Glu Asp Lys Leu Ala
                    965                 970                 975
Lys Glu Gly Arg Phe Thr Val Glu Gly Ser Val Glu Gly Thr Asp Leu
                980                 985                 990
Lys Ala Asn Val Tyr Val Arg Val  Thr Asn Glu Val Lys  Ser Val Asn
            995                      1000                     1005
```

```
Ile Met Leu Gln Glu Gln Gly Ser Ala Tyr Pro Lys Leu Glu Ala
1010                1015                1020

Thr Phe Thr Asn Pro Ala Asp Asn Leu Gln His Leu Asn Asp Gly
1025                1030                1035

Ile Lys Ser Tyr Thr Asn Asn Pro Val Asn Arg Trp Thr Asn Trp
1040                1045                1050

Thr Arg Thr Pro Arg Asp Ala Gly Asp Ser Ile Thr Val Asn Phe
1055                1060                1065

Gly Lys Lys His Val Ile Asn Asn Leu Asp Leu Phe Val Phe Thr
1070                1075                1080

Asp Ser Gly Thr Val Val Pro Glu Lys Ala Glu Val Gln Tyr Trp
1085                1090                1095

Asp Gly Thr Ala Trp Lys Asp Val Glu Asn Leu Thr Gln Pro Ser
1100                1105                1110

Pro Tyr Val Val Glu Lys Asn Glu Leu Thr Phe Asp Ala Val Ala
1115                1120                1125

Thr Glu Lys Leu Lys Phe His Leu Thr Pro Ser Val Lys Gly Lys
1130                1135                1140

Phe Leu Ala Leu Thr Glu Ala Glu Val Tyr Ala Asp Gln Ile Val
1145                1150                1155

Met Gly Glu Thr Ala Lys Leu Gln Ser Ile Thr Val Asn Gly Lys
1160                1165                1170

Ala Leu Glu Gly Phe Asp His Ala Lys Lys Asn Tyr Glu Leu Val
1175                1180                1185

Leu Pro Tyr Gly Ser Glu Leu Pro Lys Ile Glu Ala Ala Ala Ala
1190                1195                1200

Asp Asn Ala Thr Val Thr Ile Leu Pro Ala Phe Ser Tyr Pro Gly
1205                1210                1215

Thr Ala Lys Leu Phe Val Thr Ser Glu Asp Gly Lys Val Thr Thr
1220                1225                1230

Glu Tyr Ser Ile Gly Val Ser Thr Glu Glu Pro Lys Leu Val Ser
1235                1240                1245

Ala Glu Leu Ser Ala Asp Lys Thr Asn Val Met Glu Asp Asp Ile
1250                1255                1260

Ile Asp Leu Lys Val Ile Gly Leu Phe Glu Ser Lys Glu Lys Ile
1265                1270                1275

Asp Val Thr Asp Ser Gln Pro Thr Tyr Glu Phe Asp Gln Gln Ile
1280                1285                1290

Ile Lys Ile Glu Gly Asn Lys Leu Tyr Ala Leu Glu Thr Gly Asn
1295                1300                1305

Val Lys Val Lys Val Thr Val Thr Tyr Lys Gly Val Ser Val Thr
1310                1315                1320

Thr Pro Ala Leu Glu Phe Thr Ile Ala Lys Asn Pro Ala Pro Lys
1325                1330                1335

Tyr Ile Thr Ser Leu Glu Pro Val Thr Val Val Lys Lys Gly
1340                1345                1350

Glu Ala Pro Glu Leu Pro Ala Thr Val Val Ala His Tyr Asn Arg
1355                1360                1365

Gly Ile Pro Arg Asp Val Lys Val Lys Trp Glu Arg Ile Asn Pro
1370                1375                1380

Ser Lys Tyr Gln Gln Leu Gly Glu Phe Thr Val Ser Gly Met Val
1385                1390                1395
```

```
Glu Gly Thr Asp Ile Lys Ala Gln Ala Lys Val Ile Val Lys Gly
    1400                1405                1410

Ala Val Ala Val Glu Asp Ile Arg Met Ala Val Leu Leu Lys Gln
1415                1420                1425

Met Pro Gln Leu Pro Gly Lys Val Thr Val Tyr Tyr Ser Asp Gly
    1430                1435                1440

Ala Glu Glu Gln Arg Ala Val Lys Trp Glu Glu Ile Pro Gln Glu
1445                1450                1455

Glu Leu Glu Asn Val Gly Glu Phe Lys Val Lys Gly Asp Val Asn
    1460                1465                1470

Gly Val Lys Leu Lys Ala Thr Ala Thr Ile Arg Val Thr Asp Glu
1475                1480                1485

Val Gly Gly Glu Gln Asn Ile Ser Arg Ala Lys Asn Gly Tyr Glu
    1490                1495                1500

Tyr Pro Lys Ala Glu Ala Ser Phe Thr Asn Asn Gly Pro Gly Ser
1505                1510                1515

Ser Asp Arg Ile Glu Ala Ile Asn Asp Asp Val Ile Ser Tyr Glu
    1520                1525                1530

Ala Asn Pro His Asn Arg Trp Thr Asn Trp Gln Pro Val Pro Arg
1535                1540                1545

Ala Gly Asp Trp Val Ser Ile Thr Phe Gly Asp Tyr Glu Pro Thr
    1550                1555                1560

Glu Tyr Asp Val Asp Ser Met Glu Ile His Trp Phe Ala Asp His
1565                1570                1575

Gly Thr Ser Tyr Pro Glu Arg Phe Gln Ile Glu Tyr Lys Ser Gly
    1580                1585                1590

Asp Ser Trp Lys Glu Val Thr Ser Leu Lys Ser Asp Pro Ala Ser
1595                1600                1605

Pro Ala Leu Gly Lys Ala Asn Val Tyr Ser Phe Asp Arg Val Lys
    1610                1615                1620

Thr Ser Ala Ile Arg Val Lys Met Thr Ala Gln Ala Gly Lys Ser
1625                1630                1635

Leu Ala Ile Thr Glu Leu Lys Val Phe Ser Lys Trp Pro Lys Ala
    1640                1645                1650

Gly Thr Glu Pro Glu Val Thr Asp Ile Lys Val Gly Gly Lys Ser
1655                1660                1665

Ile Leu Glu Asp Phe Glu Gln Lys Gly Asp His Tyr Glu Val Thr
    1670                1675                1680

Ile Asp Ala Gly Asp Ala Asn Val Met Pro Lys Ile Asn Val Lys
1685                1690                1695

Ala Lys Asp Gln Thr Ser Ile Thr Ile Val Pro Ala Val Thr Ser
    1700                1705                1710

Pro Ser Thr Ala Lys Val Ile Ala Lys Ser Glu Asp Gly Lys Lys
1715                1720                1725

Val Lys Val Tyr Ser Ile His Tyr Lys
    1730                1735

<210> SEQ ID NO 15
<211> LENGTH: 1025
<212> TYPE: PRT
<213> ORGANISM: Kluyveromyces lactis

<400> SEQUENCE: 15

Met Ser Cys Leu Ile Pro Glu Asn Leu Arg Asn Pro Lys Lys Val His
1               5                   10                  15
```

```
Glu Asn Arg Leu Pro Thr Arg Ala Tyr Tyr Asp Gln Asp Ile Phe
            20                  25                  30

Glu Ser Leu Asn Gly Pro Trp Ala Phe Ala Leu Phe Asp Ala Pro Leu
        35                  40                  45

Asp Ala Pro Asp Ala Lys Asn Leu Asp Trp Glu Thr Ala Lys Lys Trp
50                      55                  60

Ser Thr Ile Ser Val Pro Ser His Trp Glu Leu Gln Glu Asp Trp Lys
65                  70                  75                  80

Tyr Gly Lys Pro Ile Tyr Thr Asn Val Gln Tyr Pro Ile Pro Ile Asp
                85                  90                  95

Ile Pro Asn Pro Pro Thr Val Asn Pro Thr Gly Val Tyr Ala Arg Thr
            100                 105                 110

Phe Glu Leu Asp Ser Lys Ser Ile Glu Ser Phe Glu His Arg Leu Arg
        115                 120                 125

Phe Glu Gly Val Asp Asn Cys Tyr Glu Leu Tyr Val Asn Gly Gln Tyr
130                 135                 140

Val Gly Phe Asn Lys Gly Ser Arg Asn Gly Ala Glu Phe Asp Ile Gln
145                 150                 155                 160

Lys Tyr Val Ser Glu Gly Glu Asn Leu Val Val Lys Val Phe Lys
                165                 170                 175

Trp Ser Asp Ser Thr Tyr Ile Glu Asp Gln Asp Gln Trp Trp Leu Ser
            180                 185                 190

Gly Ile Tyr Arg Asp Val Ser Leu Leu Lys Leu Pro Lys Lys Ala His
        195                 200                 205

Ile Glu Asp Val Arg Val Thr Thr Phe Val Asp Ser Gln Tyr Gln
            210                 215                 220

Asp Ala Glu Leu Ser Val Lys Val Asp Val Gln Gly Ser Ser Tyr Asp
225                 230                 235                 240

His Ile Asn Phe Thr Leu Tyr Glu Pro Glu Asp Gly Ser Lys Val Tyr
                245                 250                 255

Asp Ala Ser Ser Leu Leu Asn Glu Glu Asn Gly Asn Thr Thr Phe Ser
            260                 265                 270

Thr Lys Glu Phe Ile Ser Phe Ser Thr Lys Lys Asn Glu Glu Thr Ala
        275                 280                 285

Phe Lys Ile Asn Val Lys Ala Pro Glu His Trp Thr Ala Glu Asn Pro
290                 295                 300

Thr Leu Tyr Lys Tyr Gln Leu Asp Leu Ile Gly Ser Asp Gly Ser Val
305                 310                 315                 320

Ile Gln Ser Ile Lys His His Val Gly Phe Arg Gln Val Glu Leu Lys
                325                 330                 335

Asp Gly Asn Ile Thr Val Asn Gly Lys Asp Ile Leu Phe Arg Gly Val
            340                 345                 350

Asn Arg His Asp His His Pro Arg Phe Gly Arg Ala Val Pro Leu Asp
        355                 360                 365

Phe Val Val Arg Asp Leu Ile Leu Met Lys Lys Phe Asn Ile Asn Ala
370                 375                 380

Val Arg Asn Ser His Tyr Pro Asn His Pro Lys Val Tyr Asp Leu Phe
385                 390                 395                 400

Asp Lys Leu Gly Phe Trp Val Ile Asp Glu Ala Asp Leu Glu Thr His
                405                 410                 415

Gly Val Gln Glu Pro Phe Asn Arg His Thr Asn Leu Glu Ala Glu Tyr
            420                 425                 430
```

-continued

Pro Asp Thr Lys Asn Lys Leu Tyr Asp Val Asn Ala His Tyr Leu Ser
            435                 440                 445

Asp Asn Pro Glu Tyr Glu Val Ala Tyr Leu Asp Arg Ala Ser Gln Leu
    450                 455                 460

Val Leu Arg Asp Val Asn His Pro Ser Ile Ile Ile Trp Ser Leu Gly
465                 470                 475                 480

Asn Glu Ala Cys Tyr Gly Arg Asn His Lys Ala Met Tyr Lys Leu Ile
                485                 490                 495

Lys Gln Leu Asp Pro Thr Arg Leu Val His Tyr Glu Gly Asp Leu Asn
            500                 505                 510

Ala Leu Ser Ala Asp Ile Phe Ser Phe Met Tyr Pro Thr Phe Glu Ile
        515                 520                 525

Met Glu Arg Trp Arg Lys Asn His Thr Asp Glu Asn Gly Lys Phe Glu
    530                 535                 540

Lys Pro Leu Ile Leu Cys Glu Tyr Gly His Ala Met Gly Asn Gly Pro
545                 550                 555                 560

Gly Ser Leu Lys Glu Tyr Gln Glu Leu Phe Tyr Lys Lys Phe Tyr
                565                 570                 575

Gln Gly Gly Phe Ile Trp Glu Trp Ala Asn His Gly Ile Glu Phe Glu
            580                 585                 590

Asp Val Ser Thr Ala Asp Gly Lys Leu His Lys Ala Tyr Ala Tyr Gly
        595                 600                 605

Gly Asp Phe Lys Glu Glu Val His Asp Gly Val Phe Ile Met Asp Gly
    610                 615                 620

Leu Cys Asn Ser Glu His Asn Pro Thr Pro Gly Leu Val Glu Tyr Lys
625                 630                 635                 640

Lys Val Ile Glu Pro Val His Ile Lys Ile Ala His Gly Ser Val Thr
                645                 650                 655

Ile Thr Asn Lys His Asp Phe Ile Thr Thr Asp His Leu Leu Phe Ile
            660                 665                 670

Asp Lys Asp Thr Gly Lys Thr Ile Asp Val Pro Ser Leu Lys Pro Glu
        675                 680                 685

Glu Ser Val Thr Ile Pro Ser Asp Thr Thr Tyr Val Val Ala Val Leu
    690                 695                 700

Lys Asp Asp Ala Gly Val Leu Lys Ala Gly His Glu Ile Ala Trp Gly
705                 710                 715                 720

Gln Ala Glu Leu Pro Leu Lys Val Pro Asp Phe Val Thr Glu Thr Ala
                725                 730                 735

Glu Lys Ala Ala Lys Ile Asn Asp Gly Lys Arg Tyr Val Ser Val Glu
            740                 745                 750

Ser Ser Gly Leu His Phe Ile Leu Asp Lys Leu Leu Gly Lys Ile Glu
        755                 760                 765

Ser Leu Lys Val Lys Gly Lys Glu Ile Ser Ser Lys Phe Glu Gly Ser
    770                 775                 780

Ser Ile Thr Phe Trp Arg Pro Pro Thr Asn Asn Asp Glu Pro Arg Asp
785                 790                 795                 800

Phe Lys Asn Trp Lys Lys Tyr Asn Ile Asp Leu Met Lys Gln Asn Ile
                805                 810                 815

His Gly Val Ser Val Glu Lys Gly Ser Asn Gly Ser Leu Ala Val Val
            820                 825                 830

Thr Val Asn Ser Arg Ile Ser Pro Val Val Phe Tyr Tyr Gly Phe Glu
        835                 840                 845

```
Thr Val Gln Lys Tyr Thr Ile Phe Ala Asn Lys Ile Asn Leu Asn Thr
    850                 855                 860

Ser Met Lys Leu Thr Gly Glu Tyr Gln Pro Pro Asp Phe Pro Arg Val
865                 870                 875                 880

Gly Tyr Glu Phe Trp Leu Gly Asp Ser Tyr Glu Ser Phe Glu Trp Leu
                885                 890                 895

Gly Arg Gly Pro Gly Glu Ser Tyr Pro Asp Lys Lys Glu Ser Gln Arg
            900                 905                 910

Phe Gly Leu Tyr Asp Ser Lys Asp Val Glu Glu Phe Val Tyr Asp Tyr
        915                 920                 925

Pro Gln Glu Asn Gly Asn His Thr Asp Thr His Phe Leu Asn Ile Lys
    930                 935                 940

Phe Glu Gly Ala Gly Lys Leu Ser Ile Phe Gln Lys Glu Lys Pro Phe
945                 950                 955                 960

Asn Phe Lys Ile Ser Asp Glu Tyr Gly Val Asp Glu Ala Ala His Ala
                965                 970                 975

Cys Asp Val Lys Arg Tyr Gly Arg His Tyr Leu Arg Leu Asp His Ala
            980                 985                 990

Ile His Gly Val Gly Ser Glu Ala  Cys Gly Pro Ala Val  Leu Asp Gln
        995                 1000                1005

Tyr Arg Leu Lys Ala Gln Asp  Phe Asn Phe Glu Phe  Asp Leu Ala
    1010                1015                1020

Phe Glu
    1025
```

METHOD OF GLYCATION OF A POLYPEPTIDE

CROSS-REFERENCE TO RELATED APPLICATIONS

This application is a divisional of U.S. application Ser. No. 16/609,276 filed Oct. 29, 2019, now granted as U.S. Pat. No. 11,304,425, which is a 35 U.S.C. 371 national application of international application no. PCT/EP2018/062539 filed May 15, 2018, which claims priority or the benefit under 35 U.S.C. 119 of European application nos. 17171174.0 and 18162193.9 filed May 15, 2017 and Mar. 16, 2018, respectively. The content of each application is fully incorporated herein by reference.

SEQUENCE LISTING

The present invention comprises a sequence listing in computer readable form. The contents of the electronic sequence listing (File name: SQ.txt; size: 175 kilobytes; Date of Creation: Mar. 7, 2022) is herein incorporated by reference in its entirety.

TECHNICAL FIELD

The present invention relates to compositions, particularly liquid compositions, comprising enzymes, methods of making the compositions, and uses of the same for making, e.g., dairy products.

BACKGROUND OF THE INVENTION

Beta-galactosidase, also known as lactase, is an enzyme known to hydrolyse the terminal non-reducing beta-D-galactose residues in beta-D-galactosidases. More particularly, under normal reaction conditions, the enzyme hydrolyses its lactose substrate to the component monosaccharides D-glucose and D-galactose. Under certain conditions, certain beta-galactosidases have the ability to transfer galactose to the hydroxyl group of either glucose or galactose to form galacto-oligosaccharides (GOS) in a process called transgalactosylation.

A lactase from *Bifidobacterium bifidum* has been described having a high transgalactosylating activity, both in the full-length form and especially when truncated from the C-terminal end (see, e.g., Jorgensen et al., 2001, *Appl. Microbiol. Biotechnol.* 57: 647-652 or EP Patent 1 283 876).

WO 2009/071539 describe a differently truncated fragment compared to Jorgensen. WO 2009/071539 discloses C-terminally truncated fragment of the extracellular lactase from *Bifidobacterium bifidum*, which was originally isolated and patented for its ability to make high amounts of galactooligosaccharides from lactose, can be used very successfully for hydrolysis of lactose in milk. When tested in water+100 g/I lactose at 37° C., the enzyme makes galactooligosaccharides with high efficiency as described in the prior art. However, when tested in milk, the ratio of hydrolytic to transgalactosylating activity has changed markedly, resulting in efficient hydrolysis and very low production of galactooligosaccharides.

WO 2013/182686 describes still further differently truncated fragments compared to Jorgensen, described as efficient producers of GOS when incubated with lactose even at low lactose levels such as in a milk-based product. WO 2013/182686 also describes compositions comprising a stabilizer.

WO 2015/132349 describes liquid lactase compositions comprising lactase and further comprising sodium, calcium or potassium-L-lactate or a combination thereof and optionally a sugar.

There remains a need to develop enzymes which are efficient producers of GOS, and industrially important formulations of the same.

SUMMARY OF THE INVENTION

In one embodiment, the invention provides a formulation comprising a polypeptide having beta-galactosidase activity and at least 30 wt % of a reducing sugar, preferably fructose, galactose, glucose, or lactose.

In another embodiment, the invention provides a polypeptide having beta-galactosidase activity having been modified by glycation of at least one lysine and/or arginine residue.

In another embodiment, the invention provides a method of modifying a polypeptide having beta-galactosidase activity comprising contacting the polypeptide with a reducing sugar, preferably fructose, glucose, galactose, or lactose, for a time and temperature sufficient to produce a polypeptide modified by glycation.

In another embodiment, the invention provides a method for producing galacto-oligosaccharides (GOS) comprising contacting a formulation of the invention or a polypeptide of the invention or a polypeptide having beta-galactosidase activity which has been modified by a method of the invention with lactose.

In still another embodiment, the invention provides a method for producing galacto-oligosaccharides comprising contacting a polypeptide having a sequence comprising or consisting of amino acids 1-1304 of SEQ ID NO: 1, with lactose under conditions of high temperature and high initial lactose concentration.

DETAILED DISCLOSURE OF THE INVENTION

Despite the dominant hydrolytic properties of certain beta-galactosidase or lactase enzymes, these enzymes can be forced to have transferring properties at, e.g., high lactose and high temperature conditions. We have surprisingly discovered that when subjected to a pre-incubation, the previously hydrolytic-dominating enzyme can be converted to a transferring enzyme, which is also able to make GOS efficiently at lower temperatures than the unprocessed enzyme. The pre-incubation thus surprisingly results in a more robust GOS-producing enzyme due to its heightened transferring abilities (transgalactosylase activity).

Without wishing to be bound by theory, it is believed that these incubation conditions result in glycation of the beta-galactosidase, which results in increased transferring properties. With covalent attachment of the sugar moiety, the beta-galactosidase is converted from a hydrolysing to a transferring enzyme having transgalactosylase activity.

Beta-Galactosidase

Beta-galactosidases from glycoside hydrolase family 2 (GH2) are exo-acting enzymes, which hydrolyse terminal non-reducing beta-D-galactose residues in beta-D-galactosides, e.g., lactose is hydrolysed to galactose and glucose. They belong to the enzyme class EC 3.2.1.23 with the official name beta-D-galactoside galactohydrolase. A common name used for this enzyme is lactase, as lactose is the common industrial substrate. Besides hydrolysing this enzyme class is also able to transfer galactose to other sugars and thereby make galacto-oligosaccharides (GOS). The different GH2 enzyme have various preferences for hydrolytic or beta-galactosidase activity and transgalactosylase activity and the preference can be expressed in terms of their GOS production ability, such as by the ratio of transgalactosylating activity to beta-galactosidase activity.

In the present context, the term "beta-galactosidase" means any glycoside hydrolase having the ability to hydrolyse the disaccharide lactose into its constituent galactose and glucose monomers. Enzymes assigned to subclass EC 3.2.1.108, also called lactases, are also considered a beta-galactosidase in the context of the present invention. In the context of the invention, the lactose hydrolysing activity of the beta-galactosidase may be referred to as its lactase activity or its beta-galactosidase activity.

In the context of the present invention, the polypeptide having beta-galactosidase activity preferably belongs to the enzyme class EC 3.2.1.23 or EC 3.2.1.108, preferably 3.2.1.23. The polypeptide having beta-galactosidase activity preferably belongs to glycoside hydrolase family 2 (GH2), more preferably to the glycoside hydrolase family GH2_5.

In certain applications, combinations of polypeptides having predominantly transgalactosylating activity and predominantly hydrolysing activity may be contemplated. This may be especially useful when there is a desire to reduce residual lactose after treatment with the polypeptide having beta-galactosidase activity, for example at low lactose levels.

When considering the reaction of the polypeptide in, e.g., milk, carbohydrates are initially present in the form of lactose, a disaccharide composed of galactose and glucose that is found in milk. In the formation of GOS, successive galactose molecules are added to lactose, and then after prolonged incubation a mixture of the various carbohydrates is present (glucose, galactose and ~30 different di- and polysaccharides).

The term "disaccharide" as used herein means two monosaccharide units bound together by a covalent bond known as a glycosidic linkage formed via a dehydration reaction, resulting in the loss of a hydrogen atom from one monosaccharide and a hydroxyl group from the other. In one aspect, the disaccharide is cellobiose, fucose, lactose, lactulose, maltose, rhamnose, or sucrose, most preferably lactose.

As used herein, the term "transgalactosylase" means an enzyme that is able to transfer galactose to the hydroxyl groups of D-galactose (Gal) or D-glucose (Glc) whereby galactooligosaccharides are produced. In one embodiment, transgalactosylase activity is identified by reaction of the enzyme on lactose in which the amount of galactose generated is less than the amount of glucose generated at a given time.

More particularly, the transgalactosylase activity or preference for an enzyme to hydrolyze lactose or to produce GOS can be evaluated as the amount of glucose minus galactose generated at any given time during reaction or by direct quantification of GOS generated during the reaction. This measurement may be performed by one of several ways including the methods shown in the Examples herein.

When evaluating the transgalactosylating activity versus beta-galactosidase activity of an enzyme, the beta-galactosidase activity is measured as concentration of galactose generated at any time point during the reaction.

In the present context, the GOS production of a polypeptide is measured as $$\frac{(Glucose - Galactose)}{Galactose},$$

i.e., the ratio of transgalactosylating activity to beta-galactosidase activity.

Preferably, the ratio of transgalactosylating activity to beta-galactosidase activity is at least 1, at least 2.5, at least 3, at least 4, at least 5, at least 6, at least 7, at least 8, at least 9, at least 10, at least 11, or at least 12 as measured in high lactose conditions.

Polypeptides having beta-galactosidase activity useful according to the present invention may be of animal, of plant or of microbial origin. Preferred polypeptides are obtained from microbial sources, in particular from a filamentous fungus or yeast, or from a bacterium.

The polypeptide may, e.g., be derived from a strain of *Agaricus*, e.g., *A. bisporus*; *Ascovaginospora*; *Aspergillus*, e.g., *A. niger, A. awamori, A. foetidus, A. japonicus, A. oryzae*; *Candida*; *Chaetomium*; *Chaetotomastia*; *Dictyostelium*, e.g., *D. discoideum*; *Kluveromyces*, e.g., *K. fragilis, K. lactis*; *Mucor*, e.g., *M. javanicus, M. mucedo, M. subtilissimus*; *Neurospora*, e.g., *N. crassa*; *Rhizomucor*, e.g., *R. pusillus*; *Rhizopus*, e.g., *R. arrhizus, R. japonicus, R. stolonifer*; *Sclerotinia*, e.g., *S. libertiana*; *Torula*; *Torulopsis*; *Trichophyton*, e.g., *T. rubrum*; *Whetzelinia*, e.g., *W. sclerotiorum*; *Bacillus*, e.g., *B.* sp. *B. coagulans, B. circulans, B. megaterium, B. novalis, B. subtilis, B. pumilus, B. stearothermophilus, B. thuringiensis*; *Bifidobacterium*, e.g., *B. animalis, B. bifidum, B. breve, B. infantis, B. lactis, B. longum*; *Chryseobacterium*; *Citrobacter*, e.g., *C. freundii*; *Clostridium*, e.g., *C. perfringens*; *Diplodia*, e.g., *D. gossypina*; *Enterobacter*, e.g., *E. aerogenes, E. cloacae Edwardsiella, E. tarda*; *Erwinia*, e.g., *E. herbicola*; *Escherichia*, e.g., *E. coli*; *Klebsiella*, e.g., *K. pneumoniae*; *Miriococcum*; *Myrothesium*; *Mucor*; *Neurospora*, e.g., *N. crassa*; *Proteus*, e.g., *P. vulgaris*; *Providencia*, e.g., *P. stuartii*; *Pycnoporus*, e.g., *Pycnoporus cinnabarinus, Pycnoporus sanguineus*; *Ruminococcus*, e.g., *R. torques*; *Salmonella*, e.g., *S. typhimurium*; *Serratia*, e.g., *S. liquefasciens, S. marcescens*; *Shigella*, e.g., *S. flexneri*; *Streptomyces*, e.g., *S. antibioticus, S. castaneoglobisporus, S. violeceoruber*; *Trametes*; *Trichoderma*, e.g., *T. reesei, T. viride*; *Yersinia*, e.g., *Y. enterocolitica*.

In a preferred embodiment, the polypeptide is a beta-galactosidase from a bacterium, e.g., from the family Bifidobacteriaceae, such as from the genus *Bifidobacterium*, such as from a strain of *B. animalis, B. bifidum, B. breve, B. infantis, B. lactis*, or *B. longum*. In a more preferred embodiment, the polypeptide is a beta-galactosidase from *Bifidobacterium bifidum*.

In a preferred embodiment, the polypeptide is a beta-galactosidase from a bacterium, e.g., from the family Bacillaceae, such as from the genus *Bacillus*, such as from a strain of B. sp. *B. coagulans, B. circulans, B. megaterium, B. novalis, B. subtilis, B. pumilus, B. stearothermophilus, B. thuringiensis*; *Bifidobacterium*, e.g., *B. animalis, B. bifidum, B. breve, B. infantis, B. lactis, B. longum*. In a more preferred embodiment, the polypeptide is a beta-galactosidase from *Bacillus circulans* or *Bacillus infantis*.

A preferred polypeptide is a beta-galactosidase having a sequence which is at least 50%, such as at least 60%, at least 70%, at least 80%, at least 90%, at least 95% or at least 98% identical to amino acids 1-1304 of SEQ ID NO: 1 or a fragment thereof having beta-galactosidase activity. Such fragment of SEQ ID NO: 1 may be any fragment of SEQ ID NO: 1 having beta-galactosidase activity.

In a preferred embodiment, a polypeptide having beta-galactosidase activity to be used in a method of the present invention comprises an amino acid sequence which is at least 50% identical to amino acids 28-1931 of SEQ ID NO: 2, or a fragment thereof having beta-galactosidase activity. In a more preferred embodiment, the enzyme comprises an amino acid sequence which is at least 60%, such as at least 70%, at least 80%, at least 90%, at least 95% or at least 98% identical to amino acids 28-1931 of SEQ ID NO: 2.

In another embodiment, a polypeptide having beta-galactosidase activity to be used in a method of the present invention has an amino acid sequence which is at least 50% identical to amino acids 28-1331 of SEQ ID NO: 3, or a fragment thereof having beta-galactosidase activity. Preferably, the polypeptide has an amino acid sequence which is at least 60%, such as at least 70%, at least 80%, at least 90%, at least 95% or at least 98% identical to amino acids 28-1331 of SEQ ID NO: 3.

In another embodiment, a polypeptide having beta-galactosidase activity to be used in a method of the present invention has an amino acid sequence which is at least 50% identical to SEQ ID NO: 4, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 4.

In another embodiment, a polypeptide having beta-galactosidase activity to be used in a method of the present invention has an amino acid sequence which is at least 50% identical to SEQ ID NO: 5, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 5.

In another embodiment, a polypeptide having beta-galactosidase activity to be used in a method of the present invention has an amino acid sequence which is at least 50% identical to SEQ ID NO: 6, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 6.

In another embodiment, a polypeptide having beta-galactosidase activity to be used in a method of the present invention has an amino acid sequence which is at least 50% identical to SEQ ID NO: 7, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 7.

In another embodiment, a polypeptide having beta-galactosidase activity to be used in a method of the present invention has an amino acid sequence which is at least 50% identical to SEQ ID NO: 8, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 8.

In another embodiment, a polypeptide having beta-galactosidase activity to be used in a method of the present invention has an amino acid sequence which is at least 50% identical to SEQ ID NO: 9, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 9.

In another embodiment, a polypeptide having beta-galactosidase activity to be used in a method of the present invention has an amino acid sequence which is at least 50% identical to SEQ ID NO: 10, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 10.

In another embodiment, a polypeptide having beta-galactosidase activity to be used in a method of the present invention has an amino acid sequence which is at least 50% identical to SEQ ID NO: 11, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 11.

In another embodiment, a polypeptide having beta-galactosidase activity to be used in a method of the present invention has an amino acid sequence which is at least 50% identical to SEQ ID NO: 12, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 12.

In another embodiment, a polypeptide having beta-galactosidase activity to be used in a method of the present invention has an amino acid sequence which is at least 50% identical to SEQ ID NO: 13, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 13.

In another embodiment, a polypeptide having beta-galactosidase activity to be used in a method of the present invention has an amino acid sequence which is at least 50% identical to SEQ ID NO: 14, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 14.

In another embodiment, a polypeptide having beta-galactosidase activity to be used in a method of the present invention has an amino acid sequence which is at least 50% identical to SEQ ID NO: 15, or a fragment thereof having beta-galactosidase activity. Preferably, the polypeptide has an amino acid sequence which is at least 60%, such as at least 70%, at least 80%, at least 90%, at least 95% or at least 98% identical to SEQ ID NO: 15.

For purposes of the present invention, the sequence identity between two amino acid sequences is determined as the output of "longest identity" using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 6.6.0 or later. The parameters used are a gap open penalty of 10, a gap extension penalty of 0.5, and the EBLOSUM62 (EMBOSS version of BLOSUM62) substitution matrix. In order for the Needle program to report the longest identity, the –nobrief option must be specified in the command line. The output of Needle labeled "longest identity" is calculated as follows:

(Identical Residues×100)/(Length of Alignment– Total Number of Gaps in Alignment)

A beta-galactosidase may be extracellular. They may have a signal sequence at their N-terminus, which is cleaved off during secretion.

A polypeptide having beta-galactosidase may be derived from any of the sources mentioned herein. The term "derived" means in this context that the polypeptide may have been isolated from an organism where it is present natively, i.e., the identity of the amino acid sequence of the enzyme are identical to a native polypeptide. The term "derived" also means that the polypeptides may have been produced recombinantly in a host organism, the recombinantly produced polypeptide having either an identity identical to a native polypeptide or having a modified amino acid sequence, e.g., having one or more amino acids which are deleted, inserted and/or substituted, i.e., a recombinantly produced polypeptide which is a mutant and/or a fragment of a native amino acid sequence. Within the meaning of a native polypeptide are included natural variants. Furthermore, the term "derived" includes polypeptides produced synthetically by, e.g., peptide synthesis. The term "derived" also encompasses enzymes which have been modified, e.g., by glycosylation, phosphorylation etc., whether in vivo or in vitro. With respect to recombinantly produced polypeptide the term "derived from" refers to the identity of the polypeptide and not the identity of the host organism in which it is produced recombinantly.

The polypeptide having beta-galactosidase may be obtained from a microorganism by use of any suitable technique. For instance, a beta-galactosidase polypeptide preparation may be obtained by fermentation of a suitable microorganism and subsequent isolation of a lactase preparation from the resulting fermented broth or microorganism by methods known in the art. The polypeptide having beta-galactosidase may also be obtained by use of recombinant DNA techniques. Such method normally comprises cultivation of a host cell transformed with a recombinant DNA vector comprising a DNA sequence encoding the lactase in question and the DNA sequence being operationally linked with an appropriate expression signal such that it is capable of expressing the beta-galactosidase in a culture medium under conditions permitting the expression of the polypeptide and recovering the polypeptide from the culture. The DNA sequence may also be incorporated into the genome of the host cell. The DNA sequence may be of genomic, cDNA or synthetic origin or any combinations of these, and may be isolated or synthesized in accordance with methods known in the art.

A polypeptide having beta-galactosidase may be purified. The term "purified" as used herein covers beta-galactosidase enzyme protein essentially free from insoluble components from the production organism. The term "purified" also covers beta-galactosidase enzyme protein essentially free from insoluble components from the native organism from which it is obtained. Preferably, it is also separated from some of the soluble components of the organism and culture medium from which it is derived. More preferably, it is separated by one or more of the unit operations: filtration, precipitation, or chromatography.

Accordingly, the polypeptide having beta-galactosidase activity may be purified, viz. only minor amounts of other proteins being present. The expression "other proteins" relate in particular to other enzymes. The term "purified" as used herein also refers to removal of other components, particularly other proteins and most particularly other enzymes present in the cell of origin of the beta-galactosidase. The polypeptide having beta-galactosidase may be "substantially pure", i.e., free from other components from the organism in which it is produced, i.e., e.g., a host organism for recombinantly produced beta-galactosidase. Preferably, the beta-galactosidase is an at least 40% (w/w) pure enzyme protein preparation, more preferably at least 50%, 60%, 70%, 80% or even at least 90% pure.

The term polypeptide having beta-galactosidase activity includes whatever auxiliary compounds may be necessary for the enzyme's catalytic activity, such as, e.g., an appropriate acceptor or cofactor, which may or may not be naturally present in the reaction system.

The polypeptide may be in any form suited for the use in question, such as, e.g., in the form of a dry powder or granulate, a non-dusting granulate, a liquid, a stabilized liquid, or a protected enzyme.

The polypeptide is added in a suitable amount to achieve the desired degree of lactose hydrolysis under the chosen reaction conditions. The polypeptide may be added at a concentration of between 100 and 15,000 LAU(C) per litre milk-based substrate, preferably between 100-10,000 LAU (C) per litre milk-based substrate. Additional preferred concentrations include, e.g., 100 LAU(C)/L, 250 LAU(C)/L, 500 LAU(C)/L, 750 LAU(C)/L, 1000 LAU(C)/L, 1500 LAU(C)/L, 2000 LAU(C)/L, 5000 LAU(C)/L, 6000 LAU (C)/L, 7000 LAU(C)/L, 8000 LAU(C)/L, 9000 LAU(C)/L, 10,000 LAU(C)/L, 11,000 LAU(C)/L, 12,000 LAU(C)/L, 13,000 LAU(C)/L, 14,000 LAU(C)/L, or 15,000 LAU(C)/L.

The activity in LAU(C) of a specific beta-galactosidase may be determined by direct measurement of glucose released from lactose. The skilled person will know how to determine such activity. Alternatively, the activity may be determined by using the activity assay described in the Methods and Examples of the present application. Here, the activity is obtained by comparing to a standard curve run with a beta-galactosidase of known activity, and the activity of the unknown sample calculated from this.

The activity in LAU(B) of a specific beta-galactosidase may be determined by direct measurement of o-nitrophenyl (ONP) released from o-nitrophenyl β-D-galactopyranoside (ONPG) in a buffer containing 1.46 mg/ml substrate in 0.05 M MES, 1 mM $MgSO_4$ $7H_2O$, 450 mg/L Brij 35 at pH6.5 and 30° C. After 600 seconds incubation, the reaction is stopped by adding 0.2 M $Na_2CO_3$ and the released ONP is measured at 405 nm after 126 seconds incubation. The skilled person will know how to execute this assay and determine such activity. Here, the activity is obtained by comparing to a standard curve run with a lactase of known activity, and the activity of the unknown sample calculated from this. The lactase of known activity may, e.g., be Saphera® obtained from Novozymes A/S, Denmark.

The skilled person will know how to determine the lactase activity at different pH and temperature. The lactase activity at different pH and temperature is preferably determined by using a method as described in the Examples of the present application.

In one aspect, the polypeptide is a fragment having one or more (several) amino acids deleted from the amino or carboxyl terminal of the polypeptide of SEQ ID NO: 1, 2, 3, 4, 5, 6, 7, 8, 9, 10, 11, 12, 13, 14, or 15 wherein the fragment has beta-galactosidase activity. Particularly preferred are fragments which are carboxy-terminal truncations.

A fragment of beta-galactosidase contains at least 500, 550, 600, 650, 700, 750, 800, 850, 900, 950, 1000, 1050, 1100, 1150, 1200, 1250, or 1300 amino acid residues.

In one aspect, the beta-galactosidase is as described in WO 2013/182686.

In one aspect, the beta-galactosidase is as described in WO 2015/132349.

In an aspect, the beta-galactosidase includes a polypeptide of SEQ ID NO: 1, 2, 3, 4, 5, 6, 7, 8, 9, 10, 11, 12, 13, 14, or 15 and one or more fragments having beta-galactosidase activity, such as at least one, two, three, four, or five fragments.

Glycation

In an embodiment, the polypeptide having beta-galactosidase activity has been modified by glycation.

Without wishing to be bound by theory, it has been surprisingly found that glycation of the beta-galactosidase converts the polypeptide from a more hydrolysing to a more transferring enzyme having transgalactosylase activity.

"Glycation" as used herein refers to the covalent attachment of a carbohydrate to a protein. Carbohydrate attachment may be via a side chain of, e.g., arginine, lysine, or N-terminal of the enzyme. Preferably, the carbohydrate attachment is via a side chain of arginine or lysine.

Glycation is sometimes referred to as (non-enzymatic) glycosylation. In the context of the present invention, glycosylation and glycation are used interchangeably and glycosylation can be non-enzymatic.

In an embodiment, the polypeptide having beta-galactosidase activity has been modified by glycation of at least 1, 2, 3, 4, 5, 6, 7, 8, 9, 10, 15, 20, 25, 30, 35, 40, 45, 50, 55, 60 residues of the polypeptide.

In an embodiment, the polypeptide having beta-galactosidase activity has been modified by glycation of at least 1, 2, 3, 4, 5, 6, 7, 8, 9, 10, 15, 20, 25, 30, 35, 40, 45, 50, 55, 60 lysine and/or arginine residues of the polypeptide.

In an embodiment, the polypeptide having beta-galactosidase activity has been modified by glycation of at least 1%, 2%, 3%, 4%, 5%, 10%, 15%, 20%, 25%, 30%, 35%, 40%, 45% or 50% of the lysine and/or arginine residues of the polypeptide. In one embodiment, the polypeptide having beta-galactosidase activity has been modified by glycation of at least 1, 2, 3, 4, 5, 6, 7, 8, 9, 10, 15, 20, 25, 30, 35, 40, 45, 50, 55, 60 lysine and/or arginine residues of the polypeptide.

In a preferred embodiment, the polypeptide having beta-galactosidase activity is modified by glycation of at least 1%, preferably at least 3%, more preferably at least 5%, even more preferably at least 10%, most preferably at least 20%, of the lysine and arginine residues of the polypeptide. For the avoidance of any possible doubt, this means that at least 1%, preferably at least 3%, more preferably at least 5%, even more preferably at least 10%, most preferably at least 20%, of the total number of lysine and arginine residues of the polypeptide is modified by glycation.

In another preferred embodiment, a trypsin digest of the polypeptide having beta-galactosidase activity would result in a percentage of glycated trypsin digested peptides of at least 1%, preferably at least 3%, more preferably at least 5%, at least 10% or at least 20%.

In an embodiment, incubation under suitable conditions as detailed below results in the glycation of some, substantially all, or even all of the surface residues of lysine and/or arginine. Again without wishing to be bound by theory, it is believed that some, substantially all, or even all of the glycated residues are located towards the C-terminal end of the polypeptide having beta-galactosidase activity.

Incubation Resulting in Glycation

In an embodiment, the invention provides a method of modifying a polypeptide having beta-galactosidase activity comprising contacting the polypeptide with a sugar for a time and temperature sufficient to produce a polypeptide modified by glycation.

In an embodiment, the polypeptide is contacted with a solution of 5-90 wt % sugar at pH 5-10 for a time of 3-20 hours at a temperature of 20-80° C. Preferred sugars are reducing sugars as set forth in more detail below, and particularly preferred is glucose.

Suitable conditions include contacting the polypeptide with a solution of 5-90 wt %, sugar, such as 30-90 wt %, and in particular 30-70 wt %, e.g., 5%, 10%, 15%, 20%, 25%, 30%, 35%, 40%, 45%, 50%, 55%, 60%, 65%, 70%, 75%, 80%, 85%, or 90% sugar.

Suitable conditions include contacting the polypeptide at a pH in the range of 5-10, such as pH 5-8, e.g., pH 5, pH 5.5, pH 6, pH 6.5, pH 7, pH 7.5, pH 8, pH 8.5, pH 9, pH 9.5, or pH 10.

Suitable conditions include contacting the polypeptide for a time in the range of 3-20 hours, such as in the range of 6-16 hours, e.g., 3 hours, 3.5 hours, 4 hours, 4.5 hours, 5 hours, 5.5 hours, 6 hours, 6.5 hours, 7 hours, 7.5 hours, 8 hours, 8.5 hours, 9 hours, 9.5 hours, 10 hours, 10.5 hours, 11 hours, 11.5 hours, 12 hours, 12.5 hours, 13 hours, 13.5 hours, 14 hours, 14.5 hours, 15 hours, 15.5 hours, 16 hours, 16.5 hours, 17 hours, 17.5 hours, 18 hours, 18.5 hours, 19 hours, 19.5 hours, or 20 hours.

Suitable conditions include contacting the polypeptide at a temperature in the range of 20-80° C., such as in the range of 20-50° C., alternatively in the range of 40-80° C., in particular, 50-70° C., or alternatively, 20° C., 25° C., 30° C., 35° C., 40° C., 45° C., 50° C., 55° C., 60° C., 65° C., 70° C., 75° C., or 80° C.

In a preferred embodiment, the polypeptide having beta-galactosidase activity is contacted with a reducing sugar at pH 5-8, preferably pH 6-7, for a time of 3-100 hours, preferably 15-80 hours, at a temperature of 50-80° C., preferably 50-70° C.

The skilled person will know how to adjust the time of the contacting with the sugar according to the amount of enzyme added and the temperature. In general, if more enzyme is added, the time of contacting can be reduced. And in general, if the reaction temperature is increased, the time of contacting can be reduced. Depending on the storage conditions of the enzyme after the contacting with the sugar, the glycation process may continue on the shelf. Therefore, if the shelf temperature of the enzyme is relatively high, the time of reaction with the sugar at a specified high temperature may be reduced since the glycation process will continue during transport and storage of the enzyme before it being used by the end consumer, who may be, e.g., a dairy company or a company producing GOS as an ingredient.

In another preferred embodiment, the polypeptide having beta-galactosidase activity is contacted with 30-90 wt %, preferably 40-65 wt %, of a reducing sugar.

Sugar

The sugar in the beta-galactosidase formulation can include monosaccharides, disaccharides, or oligosaccharides. Blends of sugars are also contemplated.

Preferably, the sugar is a reducing sugar. A reducing sugar reacts with an amino acid residue of the beta-galactosidase via the Maillard reaction.

Exemplary reducing sugars include the monosaccharides fructose, galactose, glucose, glyceraldehyde, ribose, xylose. Preferred is fructose, galactose and/or glucose and most particularly fructose and/or glucose.

Other exemplary reducing sugars include disaccharides such as cellobiose, lactose and maltose, preferably lactose and/or maltose. Also exemplary are glucose polymers, e.g., maltodextrin and glycogen.

The presence of a reducing sugar can be detected by many well-known tests including the use of Benedict's reagent and/or Tollen's reagent.

Formulation

The formulation according to an embodiment of the invention may comprises a liquid composition. Liquid compositions are preferred for ease of use.

In an alternative embodiment, the formulation comprises a solid composition, e.g., a powder or a granulate.

In an embodiment, the formulation or composition according to the invention comprises a polypeptide having beta-galactosidase activity and at least 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt % or 90 wt % sugar. Preferably such a beta-galactosidase composition comprises 200-20,000 LAU(C) per g.

In one suitable formulation, the composition comprises enzyme polypeptide having beta-galactosidase activity and at least 30 wt %, 31 wt %, 32 wt %, 33 wt %, 34 wt %, 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, or 80 wt % glucose. Preferably such a beta-galactosidase composition comprises 200-20,000 LAU(C) per g.

One suitable beta-galactosidase composition comprises 200-20,000 LAU(C) per g and at least 35 wt %, 36 wt %, 37 wt %, 38 wt %, 39 wt %, 40 wt %, 41 wt %, 42 wt %, 43 wt %, 44 wt %, 45 wt %, 46 wt %, 47 wt %, 48 wt %, 49 wt %, 50 wt %, 51 wt %, 52 wt %, 53 wt %, 54 wt %, 55 wt %, 56 wt %, 57 wt %, 58 wt %, 59 wt %, 60 wt %, 61 wt %, 62 wt %, 63 wt %, 64 wt % or 65 wt % sugar, preferably in the range of 40-80 wt % sugar. A preferred beta-galactosidase composition comprises 200-20,000 LAU(C) per g and preferably 40 wt %, 60 wt %, or 80 wt % glucose.

In one embodiment, the formulation is a liquid formulation which comprises 200-15,000 LAU(C)/g, preferably 500-10,000 LAU(C)/g.

In one embodiment, the formulation is a solid formulation which comprises 1,000-20,000 LAU(C)/g, preferably 3,000-15,000 LAU(C)/g.

In an embodiment, the formulation further comprises glycerol.

However, in a preferred embodiment, the formulation is free of, or at least substantially free of, polyols or diols, such as glycerol and/or sorbitol. The amount of polyol or diol such as glycerol is preferably less than 40 wt %, less than 30 wt %, less than 25 wt %, less than 20 wt %, less than 15 wt %, less than 10 wt %, most preferably less than 5 wt %. Most preferably the formulation is free of polyol or diol such as glycerol.

In an embodiment, the formulations herein are enzymatically stable. Particularly preferred are enzymatically stable liquid enzyme formulations, and more particularly preferred are enzymatically stable liquid enzyme formulations without using glycerol. Enzymatic stability is a measure of the rate at which the activity of the enzyme decreases over time.

Also preferred are formulations, especially liquid formulations, which are microbially stable. Microbial stability is a measure of the rate at which undesired microorganisms can proliferate and grow in the composition.

In an embodiment, the formulation further comprises sodium chloride or potassium chloride, preferably in the range of 0.01-5 wt %, preferably 0.01-3 wt %, more preferably 0.01-2 wt %.

In an embodiment, the formulation further comprises a preservative. Food grade preservatives are preferred, of which benzoate, sorbate, methyl paraben, and propyl paraben are exemplary.

In an alternative but preferred embodiment, the formulation is free of preservatives such as benzoate, sorbate, methyl paraben and/or propyl paraben.

Uses

Production of galacto-oligosaccharides is contemplated under both in situ conditions from lactose already present in the milk, as well as under conditions of high initial lactose concentration (greater than 40-50% lactose (w/w)).

In an embodiment, methods for producing galacto-oligosaccharides comprising contacting a polypeptide having beta-galactosidase activity with lactose under conditions of high temperature and high initial lactose concentration. In particular, the temperature may be, e.g., 40-80° C., such as 50° C., 60° C., 65° C., 70° C., 75° C., or 80° C. Moreover, the initial lactose concentration may be above 40% (w/w), such as 40-50% (w/w), 45% (w/w), 50% (w/w), 55% (w/w), 40-60% (w/w) or even above 60% (w/w), such as 61% (w/w), 62% (w/w), 63% (w/w), 64% (w/w), 65% (w/w), 66% (w/w), 67% (w/w), 68% (w/w), 69% (w/w), 70% (w/w), 71% (w/w), 72% (w/w), 73% (w/w), 74% (w/w), 75% (w/w), or 80% (w/w) lactose.

In an aspect is provided a method for producing a dairy product comprising treating a milk-based substrate comprising lactose with a polypeptide having beta-galactosidase activity as described herein. Typically, under in situ conditions for applications of a polypeptide having beta-galactosidase activity in milk, initial lactose concentration is about 3-10% (w/w) lactose e.g., 3, 4, 5, 6, 7, 8, 9, or 10% (w/w), most typically about 5% (w/w).

The term "milk", in the context of the present invention, is to be understood as the lacteal secretion obtained by milking any mammal, such as cows, sheep, goats, buffaloes or camels.

"Milk-based substrate", in the context of the present invention, may be any raw and/or processed milk material. Useful milk-based substrates include, but are not limited to solutions/suspensions of any milk or milk like products comprising lactose, such as whole or low fat milk, skim milk, buttermilk, reconstituted milk powder, condensed milk, solutions of dried milk, UHT milk, whey, whey permeate, acid whey, or cream.

Preferably, the milk-based substrate is milk or an aqueous solution of skim milk powder. Milk powder typically has a starting lactose concentration of 36-52% (w/w/).

The milk-based substrate may be more concentrated than raw milk.

In one embodiment, the milk-based substrate has a ratio of protein to lactose of at least 0.2, preferably at least 0.3, at least 0.4, at least 0.5, at least 0.6 or, most preferably, at least 0.7.

The milk-based substrate may be homogenized and pasteurized according to methods known in the art.

"Homogenizing" as used herein means intensive mixing to obtain a soluble suspension or emulsion. It may be performed so as to break up the milk fat into smaller sizes so that it no longer separates from the milk. This may be accomplished by forcing the milk at high pressure through small orifices.

"Pasteurizing" as used herein means reducing or eliminating the presence of live organisms, such as microorganisms, in the milk-based substrate. Preferably, pasteurization is attained by maintaining a specified temperature for a specified period of time. The specified temperature is usually attained by heating. The temperature and duration may be selected in order to kill or inactivate certain bacteria, such as harmful bacteria, and/or to inactivate enzymes in the milk. A rapid cooling step may follow.' A "dairy product" in the context of the present invention may be any food product wherein one of the major constituents is milk-based. Preferable, the major constituent is milk-based. More preferably, the major constituent is a milk-based substrate which has been treated with polypeptide having beta-galactosidase activity according to a method of the invention. In the context of the present invention "one of the major constituents" means a constituent having a dry matter which constitutes more than 20%, preferably more than 30% or more than 40% of the total dry matter of the dairy product, whereas "the major constituent" means a constituent having a dry matter which constitutes more than 50%, preferably more than 60% or more than 70% of the total dry matter of the dairy product.

A dairy product according to the invention may be, e.g., skim milk, low fat milk, whole milk, cream, UHT milk, milk having an extended shelf life, a fermented milk product, cheese, yoghurt, butter, dairy spread, butter milk, acidified milk drink, sour cream, whey based drink, ice cream, condensed milk, dulce de leche or a flavoured milk drink. A dairy product may be manufactured by any method known in the art.

A dairy product may additionally comprise non-milk components, e.g., vegetable components such as, e.g., vegetable oil, vegetable protein, and/or vegetable carbohydrates. Dairy products may also comprise further additives such as, e.g., enzymes, flavouring agents, microbial cultures such as probiotic cultures, salts, sweeteners, sugars, acids, fruit, fruit juices, or any other component known in the art as a component of, or additive to, a dairy product.

In one embodiment of the invention, one or more milk components and/or milk fractions ac-count for at least 50% (weight/weight), such as at least 70%, e.g., at least 80%, preferably at least 90%, of the dairy product.

In one embodiment of the invention, one or more milk-based substrates having been treated with lactase polypeptide having beta-galactosidase activity according to a method of the invention account for at least 50% (weight/weight), such as at least 70%, e.g., at least 80%, preferably at least 90%, of the dairy product.

In one embodiment of the invention, the dairy product is a dairy product which is not enriched by addition of pre-produced galactooligosaccharides.

In one embodiment of the invention, the enzyme-treated milk-based substrate is not dried before being used as an ingredient in the dairy product.

In one embodiment of the invention, the dairy product is ice cream. In the present context, ice cream may be any kind of ice cream such as full fat ice cream, low fat ice cream, or ice cream based on yoghurt or other fermented milk products. Ice cream may be manufactured by any method known in the art.

In one embodiment of the invention, the dairy product is milk or condensed milk. Condensed milk typically has a lactose concentration of 10-20% (w/w), such as 10-16% (w/w), and in some embodiments, 18-18.5% (w/w).

In one preferred embodiment of the invention, the dairy product is UHT milk. UHT milk in the context of the present invention is milk which has been subjected to a sterilization procedure which is intended to kill all microorganisms, including the bacterial spores. UHT (ultra high temperature) treatment may be, e.g., heat treatment for 30 seconds at 130° C., or heat treatment for one second at 145° C.

In one preferred embodiment of the invention, the dairy product is ESL milk. ESL milk in the context of the present invention is milk which has an extended shelf life due to microfiltration and/or heat treatment and which is able to stay fresh for at least 15 days, preferably for at least 20 days, on the store shelf at 2-5° C.

In another preferred embodiment of the invention, the dairy product is a fermented dairy product, e.g., yoghurt.

A "fermented dairy product" in the context of the present invention is to be understood as any dairy product wherein any type of fermentation forms part of the production process. Examples of fermented dairy products are products like yoghurt, buttermilk, creme fraiche, quark and fromage frais. A fermented dairy product may be produced by any method known in the art.

"Fermentation" in the method of the present invention means the conversion of carbohydrates into alcohols or acids through the action of a microorganism. Preferably, fermentation in the method of the present invention comprises conversion of lactose to lactic acid.

In the context of the present invention, "microorganism" may include any bacterium or fungus being able to ferment the milk substrate.

The microorganisms used for most fermented milk products are selected from the group of bacteria generally referred to as lactic acid bacteria. As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of anaerobic bacteria, bifidobacteria, i.e., *Bifidobacterium* spp., which are frequently used as food cultures alone or in combination with lactic acid bacteria, are generally included in the group of lactic acid bacteria.

Lactic acid bacteria are normally supplied to the dairy industry either as frozen or freeze-dried cultures for bulk starter propagation or as so-called "Direct Vat Set" (DVS) cultures, intended for direct inoculation into a fermentation vessel or vat for the production of a fermented dairy product. Such cultures are in general referred to as "starter cultures" or "starters".

Commonly used starter culture strains of lactic acid bacteria are generally divided into mesophilic organisms having optimum growth temperatures at about 30° C. and thermophilic organisms having optimum growth temperatures in the range of about 40 to about 45° C. Typical organisms belonging to the mesophilic group include *Lactococcus lactis*, *Lactococcus lactis* subsp. *cremoris*, *Leuconostoc mesenteroides* subsp. *cremoris*, *Pseudoleuconostoc mesenteroides* subsp. *cremoris*, *Pediococcus*

*pentosaceus, Lactococcus lactis* subsp. *lactis* biovar. diacetylactis, *Lactobacillus casei* subsp. *casei* and *Lactobacillus paracasei* subsp. *paracasei*. Thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*.

Also the anaerobic bacteria belonging to the genus *Bifidobacterium* including *Bifidobacterium bifidum, Bifidobacterium animalis* and *Bifidobacterium longum* are commonly used as dairy starter cultures and are generally included in the group of lactic acid bacteria. Additionally, species of *Propionibacteria* are used as dairy starter cultures, in particular in the manufacture of cheese. Additionally, organisms belonging to the *Brevibacterium* genus are commonly used as food starter cultures.

Another group of microbial starter cultures are fungal cultures, including yeast cultures and cultures of filamentous fungi, which are particularly used in the manufacture of certain types of cheese and beverage. Examples of fungi include *Penicillium roqueforti, Penicillium candidum, Geotrichum candidum, Torula kefir, Saccharomyces kefir* and *Saccharomyces cerevisiae*.

In one embodiment of the present invention, the microorganism used for fermentation of the milk-based substrate is *Lactobacillus casei* or a mixture of *Streptococcus thermophilus* and *Lactobacillus delbrueckii* subsp. *bulgaricus*.

Fermentation processes to be used in a method of the present invention are well known and the person of skill in the art will know how to select suitable process conditions, such as temperature, oxygen, amount and characteristics of microorganism/s, additives such as, e.g., carbohydrates, flavours, minerals, enzymes, and process time. Obviously, fermentation conditions are selected so as to support the achievement of the present invention.

As a result of fermentation, pH of the milk-based substrate will be lowered. The pH of a fermented dairy product of the invention may be, e.g., in the range 3.5-6, such as in the range 3.5-5, preferably in the range 3.8-4.8.

In a preferred embodiment, the fermented dairy product is yoghurt.

In one embodiment, is provided a method of using a polypeptide having beta-galactosidase activity as described herein, or a cell expressing such polypeptide, for producing oligosaccharides. Oligosaccharides include, without limitation, fructo-oligosaccharides, galacto-oligosaccharides, isomalto-oligosaccharides, lactosucrose, malto-oligosaccharides, mannan-oligosaccharides, and xylo-oligosaccharides. Particularly preferred are galacto-oligosaccharides (GOS).

In an embodiment, oligosaccharides are produced by contacting polypeptide as described herein with a medium that comprises a disaccharide substrate including, e.g., cellobiose, lactose, lactulose, maltose, rhamnose, sucrose, and trehalose, and incubating under conditions whereby oligosaccharides are produced. The medium comprising a polypeptide as described herein may be part of a product selected from the group consisting of cheese, yoghurt, and other fermented milk products as also described more particularly above, as well as dietary supplements and probiotic comestible products. Alternatively, the oligosaccharides can be recovered and subsequently added to the product of interest before or after its preparation.

Similarly, in an embodiment, oligosaccharides may be produced by contacting a cell expressing enzyme polypeptide as described herein in a medium that comprises a disaccharide substrate including, e.g., cellobiose, lactose, lactulose, maltose, rhamnose, sucrose, and trehalose, and incubating under conditions whereby oligosaccharides are produced. The cells may be part of a product selected from the group consisting of cheese, yoghurt, and other fermented milk products as also described more particularly above, as well as dietary supplements and probiotic comestible products. Alternatively, the oligosaccharides can be recovered and subsequently added to the product of interest before or after its preparation.

In one aspect, the use of a cell for producing a product selected from the group consisting of yoghurt, cheese, fermented milk product, dietary supplement and probiotic comestible product, is provided.

In one aspect, the polypeptides described herein may be used to prepare cheese products and in methods for making the cheese products. Cheese products may be, e.g., selected from the group consisting of cream cheese, cottage cheese, and process cheese. By adding polypeptides the cheeses may contain significantly increased levels of galactooligosaccharides and reduced levels of lactose. In one aspect, the lactose levels in the final cheese product may be reduced by at least about 25%, preferably at least about 50%, and more preferably at least about 75%. The polypeptides may be used to reduce lactose in cheese products to less than about 1 gram per serving, an amount that can be tolerated by most lactose-intolerant individuals.

The cheese products provided herein are nutritionally-enhanced cheese products having increased soluble fiber content, reduced caloric content, excellent organoleptic properties, improved texture, and flavour. Further, the polypeptides described herein may reduce the glycemic index of the cheese products because GOS are more slowly absorbed than lactose or its hydrolysis products. Finally, the polypeptides may reduce the cost of production of cheese products, particularly cream cheese products, because GOS surprisingly provide improved texture to the cream cheese product, thus permitting reduced use of stabilizers, or by allowing for increased moisture content without syneresis.

In a further aspect, the use of a transgalactosylating polypeptide as disclosed herein or a cell as disclosed herein, for producing galacto-oligosaccharides, is provided. In one aspect, the use of a transgalactosylating polypeptide as disclosed herein or a cell as disclosed herein, for producing galacto-oligosaccharides to be part of a product selected from the group consisting of yoghurt, cheese, fermented dairy products, dietary supplements and probiotic comestible products, is provided. In one aspect, the product is yoghurt, cheese, or fermented dairy products. In one aspect, the use of a transgalactosylating polypeptide as disclosed herein or a cell as disclosed herein, for producing galacto-oligosaccharides to enhance the growth of *Bifidobacterium*, is provided. In one aspect, the use of a transgalactosylating polypeptide as disclosed herein or a cell as disclosed herein, for producing galacto-oligosaccharides to enhance the growth of *Bifidobacterium* in a mixed culture fermentation, is provided.

In one aspect, a process for producing a transgalactosylating polypeptide as disclosed herein, comprising culturing a cell as disclosed herein in a suitable culture medium under conditions permitting expression of said polypeptide, and recovering the resulting polypeptide from the culture, is provided. A process for producing galacto-oligosaccharides, comprising contacting of a polypeptide as disclosed herein or a cell as disclosed herein with a milk-based solution comprising lactose, is provided.

The treatment of milk products with a polypeptide that converts lactose into monosaccharides or GOS has several advantages. The products may be consumed by people with lactose intolerance that would otherwise exhibit symptoms such as flatulence and diarrhea. Dairy products treated with lactase will also have a higher sweetness than similar untreated products due to the higher perceived sweetness of glucose and galactose compared to lactose. This effect is particularly interesting for applications such as yoghurt and ice-cream where high sweetness of the end product is desired and this allows for a net reduction of carbohydrates in the consumed product. In ice-cream production, a phenomenon termed sandiness is often seen, where the lactose molecules crystallizes due to the relative low solubility of the lactose. When lactose is converted into monosaccharides or GOS the mouth feeling of the ice-cream is much improved over the non-treated products. The presence of a sandy feeling due to lactose crystallization can be eliminated and the raw material costs can be decreased by replacement of skimmed milk powder by when powder. The main effects of the enzymatic treatment are increased sweetness.

Another interesting use of the polypeptides having beta-galactosidase activity is in infant, follow-on or toddler formula. Infant formula is a manufactured food designed and marketed for feeding to babies and infants under 12 months of age, usually prepared for bottle-feeding or cup-feeding from a powder (mixed with water) or a liquid (with or without additional water). The most commonly used infant formulae contain purified cow's milk whey and casein as a protein source, a blend of vegetable oils as a fat source, lactose as a carbohydrate source, a vitamin-mineral mix, and other ingredients.

In many countries, the addition or carry-over of glycerol to infant, follow-on or toddler formula is prohibited by law, therefore in applications for infant, follow-on or toddler formula, formulations of polypeptides having beta-galactosidase activity must be free of glycerol.

In one embodiment, the polypeptides having transgalactosylating activity may be used together with other enzymes such as proteases, including chymosin or rennin, lipases such as phospholipases, amylases, and transferases.

PREFERRED EMBODIMENTS

1. A formulation comprising a polypeptide having beta-galactosidase activity and at least 30 wt % of a reducing sugar, preferably fructose, galactose, glucose, or lactose.
2. The formulation of embodiment 1, wherein the polypeptide having beta-galactosidase activity has been modified by glycation of at least one lysine and/or arginine residue.
3. The formulation of embodiment 1 or 2, wherein the polypeptide having beta-galactosidase activity has been modified by glycation of at least 1%, preferably at least 3%, more preferably at least 5%, even more preferably at least 10%, most preferably at least 20%, of the lysine and arginine residues of the polypeptide.
4. The formulation of any of the preceding embodiments, which is an enzyme formulation.
5. The formulation of any of the preceding embodiments having an activity of 200-20,000 LAU(C)/g, preferably 500-15,000 LAU(C)/g.
6. The formulation of any of the preceding embodiments which is a liquid formulation, preferably having an activity of 200-15,000 LAU(C)/g, more preferably 500-10,000 LAU(C)/g.
7. The formulation of any of the preceding embodiments which is a solid formulation, preferably having an activity of 1,000-20,000 LAU(C)/g, more preferably 3,000-15,000 LAU(C)/g.
8. The formulation of any of the preceding embodiments, comprising 40-65 wt % sugar.
9. The formulation of any of the preceding embodiments, wherein the sugar is glucose.
10. The formulation of any of the preceding embodiments, which is substantially free of glycerol.
11. The formulation of any of the preceding embodiments, which further comprises sodium chloride or potassium chloride, preferably in the range of 0.01-5 wt %, preferably 0.01-3 wt %, more preferably 0.01-2 wt %.
12. The formulation of any of the preceding embodiments, wherein the polypeptide having beta-galactosidase activity has an amino acid sequence which is at least 50%, such as at least 60%, at least 70%, at least 80%, at least 90%, at least 95% or at least 98% identical to amino acids 1-1304 of SEQ ID NO: 1 or a fragment thereof having beta-galactosidase activity; at least 50% identical, such as at least 60%, at least 70%, at least 80%, at least 90%, at least 95% or at least 98% identical to amino acids 28-1931 of SEQ ID NO: 2, or a fragment thereof having beta-galactosidase activity; at least 50% identical, such as at least 60%, such as at least 70%, at least 80%, at least 90%, at least 95% or at least 98% identical to amino acids 28-1331 of SEQ ID NO: 3, or a fragment thereof having beta-galactosidase activity; at least 50% identical, such as at least 60%, such as at least 70%, at least 80%, at least 90%, at least 95% or at least 98% identical to SEQ ID NO: 4, or a fragment thereof having beta-galactosidase activity; at least 50% identical, such as at least 60%, such as at least 70%, at least 80%, at least 90%, at least 95% or at least 98% identical to SEQ ID NO: 5, or a fragment thereof having beta-galactosidase activity; at least 50% identical, such as at least 60%, such as at least 70%, at least 80%, at least 90%, at least 95% or at least 98% identical to SEQ ID NO: 6, or a fragment thereof having beta-galactosidase activity; at least 50% identical, such as at least 60%, such as at least 70%, at least 80%, at least 90%, at least 95% or at least 98% identical to SEQ ID NO: 7, or a fragment thereof having beta-galactosidase activity; at least 50% identical, such as at least 60%, such as at least 70%, at least 80%, at least 90%, at least 95% or at least 98% identical to SEQ ID NO: 8, or a fragment thereof having beta-galactosidase activity; at least 50% identical, such as at least 60%, such as at least 70%, at least 80%, at least 90%, at least 95% or at least 98% identical to SEQ ID NO: 9, or a fragment thereof having beta-galactosidase activity; at least 50% identical, such as at least 60%, such as at least 70%, at least 80%, at least 90%, at least 95% or at least 98% identical to SEQ ID NO: 10, or a fragment thereof having beta-galactosidase activity; at least 50% identical, such as at least 60%, such as at least 70%, at least 80%, at least 90%, at least 95% or at least 98% identical to SEQ ID NO: 11, or a fragment thereof having beta-galactosidase activity; at least 50% identical, such as at least 60%, such as at least 70%, at least 80%, at least 90%, at least 95% or at least 98% identical to SEQ ID NO: 12, or a fragment thereof having beta-galactosidase activity; at least 50% identical, such as at least 60%, such as at least 70%, at least 80%, at least 90%, at least 95% or at least 98% identical to SEQ ID NO: 13, or a fragment thereof having beta-galactosidase activity; at least 50% identical, such as at least 60%, such as at least 70%, at least 80%, at least 90%, at least 95% or at least 98% identical to SEQ ID NO: 14, or a fragment thereof having beta-galactosidase activity; or at least 50% identical, such as at least 60%, such as at least 70%, at least 80%, at least 90%, at least 95% or at least 98% identical to SEQ ID NO: 15, or a fragment thereof having beta-galactosidase activity.

13. The formulation of any of the preceding embodiments, wherein the polypeptide having beta-galactosidase activity has an amino acid sequence which is at least 50%, such as at least 60%, at least 70%, at least 80%, at least 90%, at least 95% or at least 98% identical to amino acids 1-1304 of SEQ ID NO: 1 or a fragment thereof having beta-galactosidase activity; at least 50% identical, such as at least 60%, at least 70%, at least 80%, at least 90%, at least 95% or at least 98% identical to amino acids 28-1931 of SEQ ID NO: 2 to amino acids 28-1931 of SEQ ID NO: 2, or a fragment thereof having beta-galactosidase activity; at least 50% identical, such as at least 60%, such as at least 70%, at least 80%, at least 90%, at least 95% or at least 98% identical to amino acids 28-1331 of SEQ ID NO: 3, or a fragment thereof having beta-galactosidase activity; at least 50% identical, such as at least 60%, such as at least 70%, at least 80%, at least 90%, at least 95% or at least 98% identical to SEQ ID NO: 4, or a fragment thereof having beta-galactosidase activity; at least 50% identical, such as at least 60%, such as at least 70%, at least 80%, at least 90%, at least 95% or at least 98% identical to SEQ ID NO: 5, or a fragment thereof having beta-galactosidase activity; at least 50% identical, such as at least 60%, such as at least 70%, at least 80%, at least 90%, at least 95% or at least 98% identical to SEQ ID NO: 13, or a fragment thereof having beta-galactosidase activity; or at least 50% identical, such as at least 60%, such as at least 70%, at least 80%, at least 90%, at least 95% or at least 98% identical to SEQ ID NO: 14, or a fragment thereof having beta-galactosidase activity.

14. The formulation of any of the preceding embodiments, wherein the polypeptide having beta-galactosidase activity has an amino acid sequence which is at least 50%, such as at least 60%, at least 70%, at least 80%, at least 90%, at least 95%, at least 98%, or 100% identical to amino acids 1-1304 of SEQ ID NO: 1 and has a length of 900-1350 amino acids, preferably 1300-1305 amino acids, more preferably 1302 or 1304 amino acids.

15. A polypeptide having beta-galactosidase activity having been modified by glycation of at least one lysine and/or arginine residue.

16. The polypeptide of embodiment 15, which has been modified by glycation of at least 1%, preferably at least 3%, more preferably at least 5%, even more preferably at least 10%, most preferably at least 20%, of the lysine and arginine residues of the polypeptide.

17. The polypeptide of embodiment 15 or 16, which has an amino acid sequence which is at least 50%, such as at least 60%, at least 70%, at least 80%, at least 90%, at least 95% or at least 98% identical to amino acids 1-1304 of SEQ ID NO: 1 or a fragment thereof having beta-galactosidase activity; at least 50% identical, such as at least 60%, at least 70%, at least 80%, at least 90%, at least 95% or at least 98% identical to amino acids 28-1931 of SEQ ID NO: 2, or a fragment thereof having beta-galactosidase activity; at least 50% identical, such as at least 60%, such as at least 70%, at least 80%, at least 90%, at least 95% or at least 98% identical to amino acids 28-1331 of SEQ ID NO: 3, or a fragment thereof having beta-galactosidase activity; at least 50% identical, such as at least 60%, such as at least 70%, at least 80%, at least 90%, at least 95% or at least 98% identical to SEQ ID NO: 4, or a fragment thereof having beta-galactosidase activity; at least 50% identical, such as at least 60%, such as at least 70%, at least 80%, at least 90%, at least 95% or at least 98% identical to SEQ ID NO: 5, or a fragment thereof having beta-galactosidase activity; at least 50% identical, such as at least 60%, such as at least 70%, at least 80%, at least 90%, at least 95% or at least 98% identical to SEQ ID NO: 6, or a fragment thereof having beta-galactosidase activity; at least 50% identical, such as at least 60%, such as at least 70%, at least 80%, at least 90%, at least 95% or at least 98% identical to SEQ ID NO: 7, or a fragment thereof having beta-galactosidase activity; at least 50% identical, such as at least 60%, such as at least 70%, at least 80%, at least 90%, at least 95% or at least 98% identical to SEQ ID NO: 8, or a fragment thereof having beta-galactosidase activity; at least 50% identical, such as at least 60%, such as at least 70%, at least 80%, at least 90%, at least 95% or at least 98% identical to SEQ ID NO: 9, or a fragment thereof having beta-galactosidase activity; at least 50% identical, such as at least 60%, such as at least 70%, at least 80%, at least 90%, at least 95% or at least 98% identical to SEQ ID NO: 10, or a fragment thereof having beta-galactosidase activity; at least 50% identical, such as at least 60%, such as at least 70%, at least 80%, at least 90%, at least 95% or at least 98% identical to SEQ ID NO: 11, or a fragment thereof having beta-galactosidase activity; at least 50% identical, such as at least 60%, such as at least 70%, at least 80%, at least 90%, at least 95% or at least 98% identical to SEQ ID NO: 12, or a fragment thereof having beta-galactosidase activity; at least 50% identical, such as at least 60%, such as at least 70%, at least 80%, at least 90%, at least 95% or at least 98% identical to SEQ ID NO: 13, or a fragment thereof having beta-galactosidase activity; at least 50% identical, such as at least 60%, such as at least 70%, at least 80%, at least 90%, at least 95% or at least 98% identical to SEQ ID NO: 14, or a fragment thereof having beta-galactosidase activity; or at least 50% identical, such as at least 60%, such as at least 70%, at least 80%, at least 90%, at least 95% or at least 98% identical to SEQ ID NO: 15, or a fragment thereof having beta-galactosidase activity.

18. The polypeptide of any of embodiments 15-17, which has an amino acid sequence which is at least 50%, such as at least 60%, at least 70%, at least 80%, at least 90%, at least 95% or at least 98% identical to amino acids 1-1304 of SEQ ID NO: 1 or a fragment thereof having beta-galactosidase activity; at least 50% identical, such as at least 60%, at least 70%, at least 80%, at least 90%, at least 95% or at least 98% identical to amino acids 28-1931 of SEQ ID NO: 2 to amino acids 28-1931 of SEQ ID NO: 2, or a fragment thereof having beta-galactosidase activity; at least 50% identical, such as at least 60%, such as at least 70%, at least 80%, at least 90%, at least 95% or at least 98% identical to amino acids 28-1331 of SEQ ID NO: 3, or a fragment thereof having beta-galactosidase activity; at least 50% identical, such as at least 60%, such as at least 70%, at least 80%, at least 90%, at least 95% or at least 98% identical to SEQ ID NO: 4, or a fragment thereof having beta-galactosidase activity; at least 50% identical, such as at least 60%, such as at least 70%, at least 80%, at least 90%, at least 95% or at least 98% identical to SEQ ID NO: 5, or a fragment thereof having beta-galactosidase activity; at least 50% identical, such as at least 60%, such as at least 70%, at least 80%, at least 90%, at least 95% or at least 98% identical to SEQ ID NO: 13, or a fragment thereof having beta-galactosidase activity; or at least 50% identical, such as at least 60%, such as at least 70%, at least 80%, at least 90%, at least 95% or at least 98% identical to SEQ ID NO: 14, or a fragment thereof having beta-galactosidase activity.

19. The polypeptide of any of embodiments 15-18, which has an amino acid sequence which is at least 50%, such as at least 60%, at least 70%, at least 80%, at least 90%, at least 95%, at least 98%, or 100% identical to amino acids 1-1304 of SEQ ID NO: 1 and has a length of 900-1350 amino acids, preferably 1300-1305 amino acids, more preferably 1302 or 1304 amino acids.

20. A method of modifying a polypeptide having beta-galactosidase activity comprising contacting the polypeptide with a reducing sugar, preferably fructose, glucose, galactose, or lactose for a time and temperature sufficient to produce a polypeptide modified by glycation.

21. The method of embodiment 20, which is a method of modifying by glycation a polypeptide having beta-galactosidase activity.

22. The method of embodiment 20 or 21, wherein the polypeptide having beta-galactosidase activity modified by glycation has improved transgalactosylating activity as compared to the polypeptide having beta-galactosidase activity which has not been modified by glycation.

23. The method of any of embodiments 20-22, wherein the polypeptide having beta-galactosidase activity is modified by glycation of at least 1%, preferably at least 3%, more preferably at least 5%, even more preferably at least 10%, most preferably at least 20%, of the lysine and arginine residues of the polypeptide.

24. The method of any of embodiments 20-23, comprising contacting the polypeptide having beta-galactosidase activity with 30-90 wt % of a reducing sugar, preferably fructose, glucose, or galactose, at pH 5-8 for a time of 3-100 hours at a temperature of 20-80° C.

25. The method of any of embodiments 20-24, comprising contacting the polypeptide having beta-galactosidase activity at pH 5-8, preferably pH 6-7, for a time of 3-100 hours, preferably 15-80 hours, at a temperature of 50-80° C., preferably 50-70° C.

26. The method of any of embodiments 20-25, comprising contacting the polypeptide having beta-galactosidase activity with 30-90 wt %, preferably 40 wt %, 60 wt %, or 80 wt % of a reducing sugar, preferably glucose.

27. The method of any of embodiments 20-25, comprising contacting the polypeptide having beta-galactosidase activity with 30-90 wt %, preferably 40-65 wt %, of a reducing sugar.

28. The method of any of embodiments 20-27, wherein the reducing sugar is fructose, glucose or galactose, preferably glucose.

29. The method of any of embodiments 20-28, wherein the polypeptide having beta-galactosidase activity has an amino acid sequence which is at least 50%, such as at least 60%, at least 70%, at least 80%, at least 90%, at least 95% or at least 98% identical to amino acids 1-1304 of SEQ ID NO: 1 or a fragment thereof having beta-galactosidase activity; at least 50% identical, such as at least 60%, at least 70%, at least 80%, at least 90%, at least 95% or at least 98% identical to amino acids 28-1931 of SEQ ID NO: 2, or a fragment thereof having beta-galactosidase activity; at least 50% identical, such as at least 60%, such as at least 70%, at least 80%, at least 90%, at least 95% or at least 98% identical to amino acids 28-1331 of SEQ ID NO: 3, or a fragment thereof having beta-galactosidase activity; at least 50% identical, such as at least 60%, such as at least 70%, at least 80%, at least 90%, at least 95% or at least 98% identical to SEQ ID NO: 4, or a fragment thereof having beta-galactosidase activity; at least 50% identical, such as at least 60%, such as at least 70%, at least 80%, at least 90%, at least 95% or at least 98% identical to SEQ ID NO: 5, or a fragment thereof having beta-galactosidase activity; at least 50% identical, such as at least 60%, such as at least 70%, at least 80%, at least 90%, at least 95% or at least 98% identical to SEQ ID NO: 6, or a fragment thereof having beta-galactosidase activity; at least 50% identical, such as at least 60%, such as at least 70%, at least 80%, at least 90%, at least 95% or at least 98% identical to SEQ ID NO: 7, or a fragment thereof having beta-galactosidase activity; at least 50% identical, such as at least 60%, such as at least 70%, at least 80%, at least 90%, at least 95% or at least 98% identical to SEQ ID NO: 8, or a fragment thereof having beta-galactosidase activity; at least 50% identical, such as at least 60%, such as at least 70%, at least 80%, at least 90%, at least 95% or at least 98% identical to SEQ ID NO: 9, or a fragment thereof having beta-galactosidase activity; at least 50% identical, such as at least 60%, such as at least 70%, at least 80%, at least 90%, at least 95% or at least 98% identical to SEQ ID NO: 10, or a fragment thereof having beta-galactosidase activity; at least 50% identical, such as at least 60%, such as at least 70%, at least 80%, at least 90%, at least 95% or at least 98% identical to SEQ ID NO: 11, or a fragment thereof having beta-galactosidase activity; at least 50% identical, such as at least 60%, such as at least 70%, at least 80%, at least 90%, at least 95% or at least 98% identical to SEQ ID NO: 12, or a fragment thereof having beta-galactosidase activity; at least 50% identical, such as at least 60%, such as at least 70%, at least 80%, at least 90%, at least 95% or at least 98% identical to SEQ ID NO: 13, or a fragment thereof having beta-galactosidase activity; at least 50% identical, such as at least 60%, such as at least 70%, at least 80%, at least 90%, at least 95% or at least 98% identical to SEQ ID NO: 14, or a fragment thereof having beta-galactosidase activity; or at least 50% identical, such as at least 60%, such as at least 70%, at least 80%, at least 90%, at least 95% or at least 98% identical to SEQ ID NO: 15, or a fragment thereof having beta-galactosidase activity.

30. The method of any of embodiments 20-29, wherein the polypeptide having beta-galactosidase activity has an amino acid sequence which is at least 50%, such as at least 60%, at least 70%, at least 80%, at least 90%, at least 95% or at least 98% identical to amino acids 1-1304 of SEQ ID NO: 1 or a fragment thereof having beta-galactosidase activity; at least 50% identical, such as at least 60%, at least 70%, at least 80%, at least 90%, at least 95% or at least 98% identical to amino acids 28-1931 of SEQ ID NO: 2 to amino acids 28-1931 of SEQ ID NO: 2, or a fragment thereof having beta-galactosidase activity; at least 50% identical, such as at least 60%, such as at least 70%, at least 80%, at least 90%, at least 95% or at least 98% identical to amino acids 28-1331 of SEQ ID NO: 3, or a fragment thereof having beta-galactosidase activity; at least 50% identical, such as at least 60%, such as at least 70%, at least 80%, at least 90%, at least 95% or at least 98% identical to SEQ ID NO: 4, or a fragment thereof having beta-galactosidase activity; at least 50% identical, such as at least 60%, such as at least 70%, at least 80%, at least 90%, at least 95% or at least 98% identical to SEQ ID NO: 5, or a fragment thereof having beta-galactosidase activity; at least 50% identical, such as at least 60%, such as at least 70%, at least 80%, at least 90%, at least 95% or at least 98% identical to SEQ ID NO: 13, or a fragment thereof having beta-galactosidase activity; or at least 50% identical, such as at least 60%, such as at least 70%, at least 80%, at least 90%, at least 95% or at least 98% identical to SEQ ID NO: 14, or a fragment thereof having beta-galactosidase activity.

31. The method of any of embodiments 20-30, wherein the polypeptide having beta-galactosidase activity has an amino acid sequence which is at least 50%, such as at least 60%, at least 70%, at least 80%, at least 90%, at least 95%, at least 98%, or 100% identical to amino acids 1-1304 of SEQ ID NO: 1 and has a length of 900-1350 amino acids, preferably 1300-1305 amino acids, more preferably 1302 or 1304 amino acids.

32. A method for producing galacto-oligosaccharides (GOS) comprising contacting the formulation of any of embodiments 1-14 or the polypeptide of any of embodiments 15-19 or a polypeptide having beta-galactosidase activity which has been modified by the method of any of claims 20-31 with lactose.

33. A method for producing galacto-oligosaccharides (GOS) comprising contacting a polypeptide having a sequence comprising or consisting of amino acids 1-1304 of SEQ ID NO: 1, with lactose under conditions of high temperature and high initial lactose concentration.

34. The method of embodiment 33, wherein the temperature is 40-80° C., such as 50° C., 60° C., 65° C., 70° C., 75° C., or 80° C. and wherein the initial lactose concentration is above 40% (w/w), such as 40-50% (w/w), 45% (w/w), 50% (w/w), 55% (w/w), 40-60% (w/w) or even above 60% (w/w), such as 61% (w/w), 62% (w/w), 63% (w/w), 64% (w/w), 65% (w/w), 66% (w/w), 67% (w/w), 68% (w/w), 69% (w/w), 70% (w/w), 71% (w/w), 72% (w/w), 73% (w/w), 74% (w/w), 75% (w/w), or 80% (w/w) lactose.

EXAMPLES

Materials and Methods
Activity Assay (LA U(C))
Principle:

Lactase hydrolyzes lactose to form α-D-glucose. The α-D-glucose is phosphorylated by ATP, in a reaction catalyzed by hexokinase. The glucose-6-phosphate formed is oxidized to 6-phosphogluconate by glucose-6-phosphate dehydrogenase. Concomitant with this reaction an equimolar amount of NAD+ is reduced to NADH with a resulting increase in absorbance at 340 nm.

Reagents:
15% (w/v) Brij L23: Weigh out 508.0±0.4 g of Brij® L23 (Sigma B4184) into a beaker. Add approx. 300 mL ultrapure water and stir. Transfer the Brij® L23 quantitatively to a 1 L volumetric flask. Fill to the mark with ultrapure water. Stir until homogenous. Storability: 2 months in refrigerator.

Colour reagent: (Glucose reagent kit (GHK) (0.1 M Tris, 2.1 mM ATP, 2.1 mM NAD, 4 mM Mg2+, <0.1% NaN3, 4 mM Mg2+, >7.5 kU/L hexokinase, >7.5 kU/L G-6-P-DH, pH 7.8)): Open a vial of Glucose (HK) Reagent A, Thermo Fisher Scientific (Art. no.: 981304 or 981779) and a vial of Glucose (HK) Reagent B, Thermo Fisher Scientific (Art. no.: 981304 or 981779). Pour 1 vial of reagent B into 1 vial of reagent A. Put on the cap. Mix well by slowly and gently turning up and down the vial 10-15 times. Use the whole mixture in reagent A vial, or pour needed amount into an appropriate container. Storability: 1 month in refrigerator.

Dissolution buffer/dilution buffer (0.01 M Citric acid monohydrate, 0.0225% (w/v) Brij® L23, 1 mM MgSO$_4$, 7H$_2$O, pH 4.5): Weigh out 21.0±0.1 g of Citric acid monohydrate (Cas. No. 5949-29-1) and transfer quantitative to a 10 L volumetric flask. Weigh out 2.46±0.01 g of MgSO$_4$, 7H$_2$O (Cas. no. 10034-99-8) and transfer quantitative to the volumetric flask. Add approximately 9 L of demineralized water and stir until completely dissolved. Add 15 mL of 15% (w/v) Brij L23 to the volumetric flask and stir. Add approximately 35 mL of 4 M NaOH (Cas. No. 1310-73-2) and stir. Adjust pH to 4.50±0.05 using, e.g., 4 M NaOH or, e.g., HCl as appropriate. Fill to the mark with demineralized water and stir. Storability: 13 days at room temperature.

Substrate (31.6% w/w lactose monohydrate, 0.01 M citric monohydrate, 0.0225 (w/v) Brij L23, 1 mM MgSO$_4$, 7H$_2$O): Weigh out 7.9±0.2 g of Lactose monohydrate (Cas. No. 10039-26-6) directly into a beaker. Dissolve to a total volume of 25.0±0.1 g of dissolution buffer. Heat up and stir until fully dissolved with no boiling of the substrate. Storability: 6 hours at room temperature.

Standard: Enzyme standard with identified LAU(C)/g (available from Novozymes A/S, Denmark) is used as standard, diluted in dissolution buffer in the range from 0.197-0.7880 LAU (C)/m L.

Procedure:
1. 50 uL of substrate is incubated for 540 seconds at 50° C. Blank (50 uL of dissolution buffer) is subtracted out.
2. 25 uL sample in dissolution buffer is added.
3. The reaction is incubated for 1800 seconds followed by addition of 160 uL colour reagent.
4. After 300 seconds, the absorbance is measured at 340 nm.

Calculation of Enzyme Activity:
The enzyme activity of the diluted sample is read from the standard curve. Calculation of activity of a sample in LAU (C)/g is as stated in the formula:

$$\text{Activity Unit}/g = \frac{S \cdot V \cdot F}{W}$$

S=Reading from the standard curve in LAU(C)/mL
V=Volume of the measuring flask used in mL
F=Dilution factor for second dilution
W=Weight of sample in g Application in Yoghurt Commercial homogenized milk with 1.5% fat is pasteurized at 90° C. for 20 min. 200 ml of the milk is transferred into baby bottles and tempered to 43° C. The milk is inoculated with a frozen probiotic yoghurt culture, e.g., Chr. Hansen, Denmark, (F-DVS ABY-3) using an inoculation level of 0.02%. At the same time, enzyme is added to the milk. The milk samples are fermented at 43° C. until pH reached 4.55 within approximately five hours. The yoghurts are then stirred, cooled to 25° C. and placed at 8° C. for storage. Samples are collected 2 hours after addition of culture and enzyme, at end pH (pH 4.55) and after 20-24 hours (Day 1) of storage at 8° C. The biological activity is stopped by addition of sulphuric acid. Proteins are precipitated adding perchloric acid and MQW containing standards are then added. Lactose hydrolysis is measured using a Dionex ICS-3000 system equipped with a Carbopac20 connected with an electrochemical detector (ED). Peaks are identified and quantified by comparing with known standards of lactose, glucose and galactose. Content of DP2 saccharides, particularly lactose, and GOS in the form of DP3+ are identified and quantified. Vivinal GOS (Friesland Campina) is a useful standard for GOS quantification.

Application in Yoghurt

Commercial homogenized milk with 1.5% fat is pasteurized at 90° C. for 20 min. 200 ml of the milk is transferred into baby bottles and tempered to 43° C. The milk is inoculated with a frozen probiotic yoghurt culture, e.g., Chr. Hansen, Denmark, (F-DVS ABY-3) using an inoculation level if 0.02%. At the same time enzyme is added to the milk. The milk samples are fermented at 43° C. until pH reached 4.55 within approximately five hours. The yoghurts are then stirred, cooled to 25° C. and placed at 8° C. for storage. Samples are collected 2 hours after addition of culture and enzyme, at end pH (pH 4.55) and after 1, 2, 3 and 7 days of storage at 8° C. The biological activity is stopped by addition of sulphuric acid. Proteins are precipitated adding perchloric acid and MQW containing standards are then added. Lactose hydrolysis is measured using a Dionex ICS-3000 system equipped with a Carbopac20 connected with an electrochemical detector (ED). Peaks are identified and quantified by comparing with known standards of lactose, glucose and galactose. Content of DP2 saccharides, particularly lactose, and GOS in the form of DP3+ are identified and quantified. Vivinal GOS (Friesland Campina) is a useful standard for GOS quantification.

Application in 1.5% Milk

Commercial homogenized milk with 1.5% fat is transferred to tubes (10 ml) and heated in water baths to 40° C., 50° C. and 55° C., respectively. Enzyme is then added to the milk samples. Samples are collected 2 hours and 4 hours after addition of the enzyme. The biological activity is stopped by addition of sulphuric acid. Proteins are precipitated adding perchloric acid and MQW containing standards is then added. Lactose hydrolysis is measured using a Dionex ICS-3000 system equipped with a Carbopac20 connected with an electrochemical detector (ED). Peaks are identified and quantified by comparing with known standards of lactose, glucose and galactose. Content of DP2 saccharides, particularly lactose, and GOS in the form of DP3+ are identified and quantified. Vivinal GOS (Friesland Campina) is a useful standard for GOS quantification.

Application in Skimmed Milk Solution 100 ml 9% skimmed milk solution having approximately 5% lactose is made by mixing 9 g skimmed milk powder (Kerry) in 91 ml ionic water. 10 ml of the solution is transferred to a test tube containing a magnetic stirring bar and placed in a water bath at 37° C. After 15 min enzyme is added. Milk samples are taken at regular intervals up till 4 hrs. and the enzyme inactivated by heating to 99° C. for 10 min in a thermomixer. Samples are diluted appropriately and filtered through a 0.20 um filter. Lactose hydrolysis is measured using a Dionex BioLC equipped with a Dionex PA1 column and a Pulsed Amperiometrisk Detektor (PAD). Peaks are identified and quantified by comparing with known standards of lactose, glucose and galactose. Content of DP2 saccharides, particularly lactose, and GOS in the form of DP3+ are identified and quantified. Vivinal GOS (Friesland Campina) is a useful standard for GOS quantification.

Application in 1.5% Milk—High Temperature

Commercial homogenized milk with 1.5% fat is transferred to tubes (10 ml) and tempered to 63° C. Enzyme is added to the milk samples. At 63° C. samples are collected 15 minutes, 30 minutes, 2 hours and 4 hours after addition of the enzyme. The enzymatic activity in the samples is stopped by addition of sulphuric acid and proteins precipitated by addition of perchloric acid before HPLC analysis. Lactose hydrolysis is measured using a Dionex ICS-3000 system equipped with a Carbopac20 connected with an electrochemical detector (ED). Peaks are identified and quantified by comparing with known standards of lactose, glucose and galactose. Content of DP2 saccharides, particularly lactose, and GOS in the form of DP3+ are identified and quantified. Vivinal GOS (Friesland Campina) is a useful standard for GOS quantification.

Application in Whey Permeate Solution 100 ml 15 or 30% (w/w) whey permeate containing primarily lactose and ions is made by mixing 15 or 30 g spray-dried whey permeate powder (Variolac, Arla) in 85 or 70 ml ionic water respectively. The solution is poured in a flask containing a magnetic stirring bar and placed in a water bath at 37° C. After 15 min, enzyme is added. Milk samples are taken at regular intervals up till 5.5 hrs. and the enzyme inactivated by heating to 99° C. for 10 min in a thermomixer. Samples are diluted appropriately and filtered through a 0.20 um filter. Lactose hydrolysis is measured using a Dionex BioLC equipped with a Dionex PA1 column and a Pulsed Amperiometrisk Detektor (PAD). Peaks are identified and quantified by comparing with known standards of lactose, glucose and galactose. Content of DP2 saccharides, particularly lactose, and GOS in the form of DP3+ are identified and quantified. Vivinal GOS (Friesland Campina) is a useful standard for GOS quantification.

Example 1

Production of Polypeptide

Bifidobacterium bifidum β-galactosidase (BBB) having the sequence shown as SEQ ID NO: 1 is expressed in Bacillus licheniformis Example 2

Glycation

BBB-un_1: Untreated Bifidobacterium bifidum β-galactosidase (BBB-un_1) is expressed in Bacillus licheniformis according to Example 1 and concentrated using ultra filtration (cut-off 10 kDa) and finally formulated with glycerol 50% (w/w). Activity of this sample is 7210 LAU(C)/g.

To a 100 ml Distec vessel, 100 grams of 66% (w/w) sugar (glucose (Glc), galactose (Gal) or lactose (Lac)) solution with 20 mM succinic acid buffer pH 6.5 is added and preheated to 60° C. for 15 min. Then 10 ml BBB-un_1 without glycerol is added and incubated at 60° C. with mixing for 16 hr. The solution is cooled to room temperature and dialyzed (cut-off 12 kDa) against 5 mM succinic acid buffer pH 6.5 for 16 hr at 5° C. and then concentrated to ~5 ml using Amicon cell cut-off 10 kDa and finally added the same volume of glycerol to give a conc. of 50% glycerol (v/v). The three samples generated from this procedure are termed BBB-Glc, BBB-Gal and BBB-Lac referring to the sugar used for the incubation.

Filter-aided sample preparation (FASP) MS data from tryptic digests was made and glycated peptides were identified as Lys and Arg+1 Hexose, causing 1 missed cleavage site. The % of glycated trypsin digested peptides were estimated to be 0.66%, 31%, 36% and 27% for untreated, lactose treated, glucose treated and galactose treated respectively. Thus, mass spectrometery of peptides made from trypsin digest confirms glycation on lysine and arginine residues of BBB-Glc, BBB-Gal and BBB-Lac but these glycations are not present in BBB-un_1.

GOS Production at 25° C.

To evaluate GOS produced at 25° C., 50 ul 1280 LAU (C)/g enzyme (BBB-un_1, BBB-Glc, BBB-Gal or BBB-Lac) is mixed with 950 ul preheated 66.5% lactose*H$_2$O (w/w), 20 mM succinate pH 6.5 in an Eppendorf tube which gives a final concentration of 60% lactose. This mixture is then incubated at 25° C. with 1000 rpm for 22 hr and applied on ice. Inactivation of the enzyme is then performed by diluting the 1 ml GOS product with 49 ml 0.04 M NaOH, 1 mM EDTA and incubated for 5 min at room temp. Then an additional 40× dilution with milli Q water (i.e., 2000× dilution in total) is made and applied to a PA1 column (High-Performance Anion-Exchange Chromatography) with Pulsed Amperometric Detection (HPAEC-PAD).

GOS Production at 65° C.

In order to evaluate GOS produced at 65° C., 50 ul 192 LAU(C)/g enzyme (BBB-un_1, BBB-Glc, BBB-Gal or BBB-Lac) is mixed with 950 ul preheated 66.5% lactose*H20 (w/w), 20 mM succinate pH 6.5 in an Eppendorf tube which gives a final concentration of 60% lactose. This mixture is then incubated at 65° C. with 1000 rpm for 22 hr and applied on ice. Inactivation of the enzyme is then performed by diluting the 1 ml GOS product with 49 ml 0.04 M NaOH, 1 mM EDTA and incubated for 5 min at room temp. Then an additional 40× dilution with milli Q water (i.e., 2000× dilution in total) is made and applied to a PA1 column (High-Performance Anion-Exchange Chromatography) with Pulsed Amperometric Detection (HPAEC-PAD).

TABLE 1

|  | (Glc-Gal)/Gal 25° C. | (Glc-Gal)/Gal 65° C. |
| --- | --- | --- |
| BBB-un_1 | 0.79 | 10 |
| BBB-Lac | 6.9 | 12 |
| BBB-Glc | 7.8 | 13 |
| BBB-Gal | 6.0 | 12 |

As seen in Table 1, untreated *Bifidobacterium bifidum* beta-galactosidase (BBB-un_1) has low transgalactosylating activity at 25° C. with a (Glc-Gal)/Gal ratio of 0.79 compared with the glycated BBB forms (BBB-Glc, BBB-Gal and BBB-Lac) which have 7-10 fold higher (Glc-Gal)/Gal ratio when incubated at the same process conditions. At 65° C., the difference is less pronounced between untreated and glycated BBB and only a 1.2-1.3 fold increase in (Glc-Gal)/Gal ratio is seen. However, it is surprising that all enzyme BBB-un_1, BBB-Glc, BBB-Gal and BBB-Lac have a pronounced increase in (Glc-Gal)/Gal ratio at elevated temperature, 65° C. compared to 25° C., especially for BBB-un which has a 13-fold increase in (Glc-Gal)/Gal ratio.

Example 3

Sample:
BBB-un_2: Untreated *Bifidobacterium bifidum* β-galactosidase (BBB-un_2) is expressed in *Bacillus licheniformis* according to Example 1 and concentrated using ultrafiltration (cut-off 10 kDa) and finally formulated with glucose 40% (w/w), 60% (w/w) or 80% (w/w), with an enzyme concentration of 7575 LAU(C)/g, 9200 LAU(C)/g and 4600 LAU(C)/g, respectively.
Glycation of Enzyme Samples:
Enzyme solution formulated with glucose are incubated for 16 h and 40 h at three different temperatures 50° C., 55° C. and 60° C., see Table 2.
GOS Production at 25° C.

To evaluate GOS produced at 25° C., 50 μl enzyme sample as shown in Table 2 is mixed with 950 μl preheated 66.5% lactose*H20 (w/w), 20 mM succinate pH 6.5 in an Eppendorf tube which gives a final concentration of 60% lactose. This mixture is then incubated at 25° C. with 1000 rpm for 22 hr and applied on ice. Inactivation of the enzyme is then performed by diluting the 1 ml GOS product with 49 ml 0.04 M NaOH, 1 mM EDTA and incubated for 5 min at room temp. Then an additional 40× dilution with milli Q water (i.e., 2000× dilution in total) is made and applied to a PA1 column (which is High-Performance Anion-Exchange Chromatography, HPAEC) and carbohydrates were detected with Pulsed Amperometric Detection (PAD).

Results & Discussion

TABLE 2

| LAU(C)/g | Temperature ° C. | Time h | Glucose conc. % | (Glc-Gal)/Gal Ratio |
| --- | --- | --- | --- | --- |
| 7575 | No heat treatment |  | 40 | 0.5 |
| 7575 | 50 | 16 | 40 | 0.9 |
| 7575 | 55 | 16 | 40 | 0.9 |
| 7575 | 60 | 16 | 40 | 1.4 |
| 7575 | 50 | 40 | 40 | 1.6 |
| 7575 | 55 | 40 | 40 | 2.1 |
| 7575 | 60 | 40 | 40 | 2.5 |
| 9200 | No heat treatment |  | 60 | 0.5 |
| 9200 | 50 | 16 | 60 | 0.9 |
| 9200 | 55 | 16 | 60 | 1.4 |
| 9200 | 60 | 16 | 60 | 2.0 |
| 9200 | 50 | 40 | 60 | 2.2 |
| 9200 | 55 | 40 | 60 | 2.9 |
| 9200 | 60 | 40 | 60 | 3.3 |
| 4600 | 50 | 16 | 80 | 1.9 |
| 4600 | 55 | 16 | 80 | 4.3 |
| 4600 | 60 | 16 | 80 | 5.0 |
| 4600 | 50 | 40 | 80 | 5.3 |
| 4600 | 55 | 40 | 80 | 6.1 |
| 4600 | 60 | 40 | 80 | 6.1 |

Table 2 shows that there is an increase in the (Glc-Gal)/Gal ratio when the temperature is increased from 50 to 60° C. and the (Glc-Gal)/Gal ratios are higher than control where no heat treatment has been made. Prolonged incubation times also increases the (Glc-Gal)/Gal ratio, i.e., higher values are obtained after 40 h compared to 16 h. The effect of the temperature and time is the same for enzymes formulated with 40%, 60% and 80% glucose.

Example 4

Glycation of Enzyme Samples
Untreated *Bifidobacterium bifidum* β-galactosidase (BBB-un) is expressed in *Bacillus licheniformis* according to Example 1 and concentrated using ultrafiltration (cut-off 10 kDa) and formulated with glucose at levels as indicated in the table by incubating for 44 h at 55° C. then stored at 4° C.
GOS Production in Milk at 5° C.
One ml semi-skim milk is applied in 2 ml Eppendorf tube and heated to 90° C. for 5 min and cooled in ice-bath for at least 30 min. Then 10 μl diluted enzyme sample is added and incubated for 24 h at 5° C. The reaction is stopped by adding 5 μl HAc and heated to 90° C. for 5 min and centrifuged at 20,000 g for 5 min. Then 50 μl supernatant is added to 500 μl Milli Q water+10 μl Carrez I solution in a 5 ml Eppendorf tube and mixed followed by adding 10 μl Carrez II solution and mixed. Then 4.43 ml milli Q water is added and centrifuged at 20,000 g for 5 min at room temperature. Then 1 ml of supernatant is added to 4 ml water and filtered through a 0.20 μm filter into a HPLC vial and applied to a PA1 HPAEC column and carbohydrates are detected with PAD.
GOS Production in Milk at 42° C.
One ml semi-skim milk is applied in 2 ml Eppendorf tube and heated to 90° C. for 5 min and cooled in ice-bath for at least 30 min. Then 10 μl diluted enzyme sample is added and incubated for 6 h at 42° C. The reaction is stopped by adding 5 μl HAc and heated to 90° C. for 5 min and centrifuged at 20,000 g for 5 min. Then 50 μl supernatant is added to 500 μl Milli Q water+10 μl Carrez I solution in a 5 ml Eppendorf tube and mixed followed by adding 10 μl Carrez II solution and mixed. Then 4.43 ml milli Q water is added and centrifuged at 20,000 g for 5 min at room temperature. Then 1 ml of supernatant is added to 4 ml water and filtered through a 0.20 μm filter into a HPLC vial and applied to a PA1 HPAEC column and carbohydrates are detected with PAD.

GOS Production in 35% Reconstituted Skim Milk Powder at 42° C.

One ml 35% (w/w) reconstituted skim milk powder is applied in 2 ml eppendorf tube and heated to 90° C. for 5 min and cooled in ice-bath for at least 30 min. Then 10 μl diluted enzyme sample is added and incubated for 6 h at 42° C. The reaction is stopped by adding 5 μl HAc and heated to 90° C. for 5 min and centrifuged at 20,000 g for 5 min. Then 50 μl supernatant is added to 500 μl Milli Q water+10 μl Carrez I solution in a 5 ml Eppendorf tube and mixed followed by adding 10 μl Carrez II solution and mixed. Then 4.43 ml milli Q water is added and centrifuged at 20,000 g for 5 min at room temperature. Then 0.35 ml of supernatant is added to 4.65 ml water and filtered through a 0.20 μm filter into a HPLC vial and applied to a PA1 column (which is High-Performance Anion-Exchange Chromatography, HPAEC) and carbohydrates are detected with Pulsed Amperometric Detection (PAD).

Results & Discussion

TABLE 3

Data from GOS production in milk at 5° C.

| Enzyme amount LAU(C)/mL | Temperature ° C. | Time h | Glucose conc. % | (Glc-Gal)/Gal ratio | mean dev. |
|---|---|---|---|---|---|
| 640 | 55 | 44 | 40 | 0.34 | 0.01 |
| 640 | 55 | 44 | 60 | 1.06 | 0.03 |
| 640 | No heat treatment | | 40 | 0.07 | 0.002 |

TABLE 4

Data from GOS production in milk at 42° C.

| Enzyme amount LAU(C)/mL | Temperature ° C. | Time h | Glucose conc. % | (Glc-Gal)/Gal ratio | mean dev. |
|---|---|---|---|---|---|
| 290 | 55 | 44 | 40 | 0.31 | 0.02 |
| 290 | 55 | 44 | 60 | 0.51 | 0.02 |
| 290 | No heat treatment | | 40 | 0.05 | 0.004 |

TABLE 5

Data from GOS production in 35% (w/w) reconstituted skim milk powder at 42° C.

| Enzyme amount LAU(C)/mL | Temperature ° C. | Time h | Glucose conc. % | (Glc-Gal)/Gal ratio | mean dev. |
|---|---|---|---|---|---|
| 840 | 55 | 44 | 40 | 0.68 | 0.005 |
| 840 | 55 | 44 | 60 | 1.8 | 0.2 |
| 840 | No heat treatment | | 40 | 0.07 | 0.003 |

Tables 3, 4 and 5 show that (Glc-Gal)/Gal ratio is increased for both 40% and 60% glucose formulations when incubated at 55° C. for 44 h compared to 40% glucose control (No heat treatment). These results show that GOS can be generated in-situ (in milk) at 5° C. which is the common storage temperature of milk but also at 42° C. which is useful for yoghurt application as 42° C. is a common fermentation temperature. An even higher (Glc-Gal)/Gal ratio can be achieved in 35% (w/w) reconstituted skim milk powder (table 5), i.e., increasing the dry matter content and lactose concentration therefore increasing transferase efficiency.

Example 5

Glycosylation of Enzyme Samples

Untreated *Bifidobacterium bifidum* β-galactosidase (BBB) having the sequence shown as SEQ ID NO: 1 is expressed in *Bacillus licheniformis* and concentrated using ultrafiltration (cut-off 10 kDa) to 23000 LAU(B)/g and formulated with either 60% (w/w) glucose (3 gram glucose+2 gram BBB-un) or 60% (w/w) glycerol (3 gram glycerol+2 gram BBB-un) and incubated for 66 h at 50° C. or unformulated diluted with water with same dilution, i.e., 3 gram water+2 gram BBB-un and incubated for 30 min at 50° C.

GOS Production at 25° C.

To evaluate GOS produced at 25° C., 50 ul 770 LAU(B)/g enzyme is mixed with 950 ul preheated 66.5% lactose*H20 (w/w), 20 mM succinate pH 6.5 in an Eppendorf tube which gives a final concentration of 60% lactose. This mixture is then incubated at 25° C. with 1000 rpm for 22 hr and applied on ice. Inactivation of the enzyme is then performed by diluting the 1 ml GOS product with 9 ml 0.04 M NaOH and incubated for 5 min at room temp. Then an additional 200× dilution with milli Q water (i.e., 2000× dilution in total) is made and applied to a PA1 column (High-Performance Anion-Exchange Chromatography) with Pulsed Amperometric Detection (HPAEC-PAD).

TABLE 6

| Formulation | Enzyme amount LAU(B)/g | Temperature ° C. | Time h | (Glc-Gal)/Gal ratio | mean dev. |
|---|---|---|---|---|---|
| BBB treated in 60% glucose | 770 | 50 | 66 | 5.5 | 0.1 |
| BBB treated in 60% glycerol | 770 | 50 | 66 | 0.70 | 0.05 |
| BBB treated in water | 770 | 50 | 0.5 | 0.68 | 0.01 |

The incubation in 60% glucose is made at 50° C. for 66 h to ensure glycation of the *Bifidobacterium bifidum* β-galactosidase (BBB). Incubation in 60% glycerol (which is not a reducing sugar) is included as a control. The sample without formulating agent (BBB treated in water) is included as another control. Due to instability of the enzyme when no stabilizer is added (e.g., glucose or glycerol), the enzyme would not be stable for 66 h at 50° C. and therefore the "BBB treated in water" sample was incubated only for 0.5 h at 50° C.

Table 6 shows that only high (Glc-Gal)/Gal ratio (5.5) is obtained by incubating *Bifidobacterium bifidum* β-galactosidase (BBB) with glucose and not with controls formulated in glycerol or without formulation agents (water). Thus, these results show that it is not heating of the enzyme sample as such that transforms the enzyme to get a high (Glc-Gal)/Gal ratio. It is the incubation with glucose at conditions that enable glycation of the enzyme that ensures the transformation from low to high (Glc-Gal)/Gal ratio.

Example 6

Sample:

BBB-1: *Bifidobacterium bifidum* β-galactosidase having the sequence shown as SEQ ID NO: 1 has been expressed in *Bacillus licheniformis* and column purified and then finally formulated with 60% glucose (BBB-1-G) and incubated for 66 h at 50° C. as shown in Table 6 and then stored at −20° C. Control sample (BBB-1-C) were not formulated with glucose and just stored at −20° C.

*Kluyveromyces lactis* β-galactosidase (Lactozym® Pure) has been expressed in *Kluyveromyces lactis* and concentrated using UF (cut-off 10 kDa) and finally formulated with 60% glucose with same enzyme protein conc. ([ep]) as BBB-1-G and incubated for 66 h at 50° C. as shown in Table 6 and then stored at −20° C. Control sample was not formulated with glucose and just stored at −20° C. and has the same enzyme protein conc. ([ep]) as BBB-1-C.

*Bacillus circulans* β-galactosidase having the sequence shown as amino acids 28-1737 of SEQ ID NO: 14 has been expressed in *Bacillus subtilis* and column purified and then finally formulated with 60% glucose with same enzyme protein conc. ([ep]) as BBB-1-G and incubated for 66 h at 50° C. as shown in Table 6 and then stored at −20° C. Control sample was not formulated with glucose and just stored at −20° C. and has the same enzyme protein conc. ([ep]) as BBB-1-C.

BBB-2: *Bifidobacterium bifidum* β-galactosidase having the sequence shown as SEQ ID NO: 1 has been expressed in *Bacillus licheniformis* and concentrated using UF (cut-off 10 kDa) and finally formulated with 50% glycerol and incubated for 4 weeks (672 h) at 40° C. as shown in Table 6 and then stored at −20° C. Control sample was not incubated at 40° C. but just stored at −20° C. during the 4 weeks.

BBB-3: *Bifidobacterium bifidum* β-galactosidase having the sequence shown as SEQ ID NO: 1 has been expressed in *Bacillus licheniformis* and concentrated using UF (cut-off 10 kDa) and finally formulated with 40% glucose and incubated for 4 weeks (672 h) at 40° C. as shown in Table 6 and then stored at −20° C. Control sample was not incubated at 40° C. but just stored at −20° C. during the 4 weeks.

GOS Production in Regular Milk

5° C. for 24 h (Results are Shown in Table 6).

Two ml semi-skim milk (Arta, purchased in a local Danish supermarket, 4.7 g lactose and 3.5 g protein per 100 g) was transferred into a 5 ml Eppendorf tube (double determinations for each dose including control). Then 20 μl of enzyme dilution was added (see Table 6) and mixed followed by an incubation at 5° C. for 24 h. After incubation, 10 μl concentrated acetic acid was added to each sample and the solutions were heated to 90° C. for 5 min. After inactivation, the samples were centrifuged at 14,000 rpm for 5 min at room temperature. One ml supernatant was transferred to another tube and kept frozen until analysed by HPLC.

Determination of Ratio of (Glc-Gal)/Gal

High-Performance Anion-Exchange Chromatography with Pulsed Amperometric Detection (HPAEC-PAD) using a PA1 column for quantitative determination of galactose (Gal) and glucose (Glc) is performed as follows.

50 μl sample is mixed together with 500 μl Milli Q water+10 μl Carrez I solution in a 5 ml Eppendorf tube, and then mixed with 10 μl Carrez II solution. Then 4.43 ml milli Q water is added and centrifugated at 14,000 rpm for 5 min at room temperature. One ml supernatant is mixed with 4 ml Milli-Q water and filtered through a 0.2 μm filter into a HPLC vial and applied on a PA1 column. Quantitative determination of Glc and Gal was made using a known standard of Glc and Gal, respectively.

TABLE 6

| | Enzyme amount LAU (B)/g | Temperature ° C. | Time h | (Glc-Gal)/Gal ratio | mean dev. |
|---|---|---|---|---|---|
| BBB-1-G (60% glucose) | 260 | 50 | 66 | 3.39 | 0.03 |
| *K. lactis* (60% glucose) | "same [ep] as BBB-1-G" | 50 | 66 | 0.40 | 0.02 |
| *B. circulans* (60% glucose) | "same [ep] as BBB-1-G" | 50 | 66 | 4.09 | 0.07 |
| BBB-1-C—control | 640 | No heat treatment | | −0.04 | 0.005 |
| *K. lactis*—control | "same [ep] as BBB-1-C" | No heat treatment | | 0.00 | 0.02 |
| *B. circulans*—control | "same [ep] as BBB-1-C" | No heat treatment | | 0.00 | 0.001 |
| BBB-2 (50% glycerol) | 640 | 40 | 672 | −0.02 | 0.02 |
| BBB-3 (40% glucose) | 640 | 40 | 672 | 0.75 | 0.14 |
| BBB-2 (50% glycerol)—control | 640 | −20 | 672 | −0.02 | 0.02 |
| BBB-3 (40% glucose)—control | 640 | −20 | 672 | −0.01 | 0.01 |

A pronounced increase in (Glc-Gal)/Gal ratio is seen when *Bifidobacterium bifidum* β-galactosidase and *Bacillus circulans* β-galactosidase (both GH2_5) is incubated with 60% glucose at 50° C. for 66 h with a (Glc-Gal)/Gal ratio of 3.39 and 4.09, respectively. Whereas a smaller increase in (Glc-Gal)/Gal ratio is seen for *Kluyveromyces lactis* β-galactosidase (GH2_6). This suggests that for subfamily 5 of the glycosyl hydrolase family 2 (GH2_5), glycation has a more pronounced affect to shift the enzyme molecule from having a hydrolytic to a transferase activity, than for subfamily 6 of GH2 (GH2_6).

All control samples BBB-1-C, *K. lactis* and *B. circulans* have a (Glc-Gal)/Gal ratio close to zero. When compared to the small but positive values for the controls of Example 5, this is as expected as there is only ~5% lactose in milk whereas the controls in Table 5 were incubated at 60% lactose (a high lactose conc. favours transferase activity).

Glycation in lower glucose conc. and lower temperatures could also be achieved at prolonged incubation times as seen in Table 6, where BBB-3 incubated in 40% glucose at 40° C. for 672 h resulted in a (Glc-Gal)/Gal ratio of 0.75 compared to control which has a value of zero. An additional control was made incubating *Bifidobacterium bifidum* β-galactosidase in 40% glycerol at 40° C. for 672 h which has no detectable effect on the (Glc-Gal)/Gal ratio as a value of zero was obtained just as for the control. This additional experiment confirms that glycation and not heat-treatment as such is responsible for transforming the enzyme from a hydrolytic enzyme to a more transferring enzyme.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method of modifying by glycation a polypeptide having beta-galactosidase activity, comprising:
    contacting the polypeptide with 30-90 wt % of a reducing sugar under conditions sufficient to produce a polypeptide modified by glycation,
    wherein the reducing sugar is fructose, galactose, glucose, glyceraldehyde, ribose, xylose, cellobiose, maltose, or lactose, wherein the conditions comprise contacting the polypeptide in a solution at pH 5-8, for a time of 3-100 hours, at a temperature of 50-80° C., and wherein the polypeptide has at least 3% of lysine and arginine residues of the polypeptide modified by glycation.

2. The method of claim 1, wherein the polypeptide has improved transgalactosylating activity as compared to a polypeptide having beta-galactosidase activity which has not been modified by glycation.

3. The method of claim 1, wherein the polypeptide has at least 5% of lysine and arginine residues of the polypeptide modified by glycation.

4. The method of claim 1, wherein the polypeptide is contacted with 40-65 wt. % of a reducing sugar.

5. The method of claim 1, wherein the polypeptide is from subfamily 5 of glycosyl hydrolase family 2 (GH2_5).

6. The method of claim 1, wherein the polypeptide is from subfamily 6 of glycosyl hydrolase family 2 (GH2_6).

7. The method of claim 1, wherein the polypeptide is a *Bacillus* polypeptide.

8. The method of claim 1, wherein the polypeptide is a *Bacillus circulans* polypeptide.

9. The method of claim 1, wherein the polypeptide is a *Bifidobacterium* polypeptide.

10. The method of claim 1, wherein the polypeptide is a *Bifidobacterium bifidum* polypeptide.

11. The method of claim 1, wherein the polypeptide is a *Kluyvermyces* polypeptide.

12. The method of claim 1, wherein the polypeptide is a *Kluyvermyces lactis* polypeptide.

* * * * *